US011198681B2

(12) United States Patent
Devraj et al.

(10) Patent No.: US 11,198,681 B2
(45) Date of Patent: Dec. 14, 2021

(54) HETEROARYL INHIBITORS OF PAD4

(71) Applicant: Padlock Therapeutics, Inc., Princeton, NJ (US)

(72) Inventors: Rajesh Devraj, Chesterfield, MO (US); Gnanasambandam Kumaravel, Lexington, MA (US); Holly Atton, Abingdon (GB); Edward Beaumont, Abingdon (GB); Elise Gadouleau, Abingdon (GB); Laura Gleave, Abingdon (GB); Philip Stephen Kerry, Abingdon (GB); Cristina Lecci, Abingdon (GB); Mirco Meniconi, Abingdon (GB); Nat Monck, Abingdon (GB); Jordan Palfrey, Abingdon (GB); Kostas Papadopoulos, Abingdon (GB); Heather Tye, Abingdon (GB); Philip A. Woods, Abingdon (GB)

(73) Assignee: Padlock Therapeutics, Inc., Princeton, NJ (US)

( * ) Notice: Subject to any disclaimer, the term of this patent is extended or adjusted under 35 U.S.C. 154(b) by 342 days.

(21) Appl. No.: 16/078,376

(22) PCT Filed: Feb. 22, 2017

(86) PCT No.: PCT/US2017/018790
§ 371 (c)(1),
(2) Date: Aug. 21, 2018

(87) PCT Pub. No.: WO2017/147102
PCT Pub. Date: Aug. 31, 2017

(65) Prior Publication Data
US 2021/0188810 A1 Jun. 24, 2021

Related U.S. Application Data

(60) Provisional application No. 62/298,726, filed on Feb. 23, 2016.

(51) Int. Cl.
*C07D 471/04* (2006.01)
*A61K 31/437* (2006.01)
*C07D 401/14* (2006.01)
*A61K 31/4184* (2006.01)
*A61K 31/454* (2006.01)
*A61K 31/4545* (2006.01)
*C07D 403/14* (2006.01)
*C07D 405/14* (2006.01)
*C07D 417/14* (2006.01)

(52) U.S. Cl.
CPC ........ *C07D 401/14* (2013.01); *A61K 31/4184* (2013.01); *A61K 31/437* (2013.01); *A61K 31/454* (2013.01); *A61K 31/4545* (2013.01); *C07D 403/14* (2013.01); *C07D 405/14* (2013.01); *C07D 417/14* (2013.01); *C07D 471/04* (2013.01)

(58) Field of Classification Search
CPC .. C07D 471/04; C07D 401/14; C07D 403/14; A61K 31/437; A61K 31/454; A61K 31/4184; A61P 35/00; A61P 37/00
USPC ...... 546/113, 199; 548/304.7; 514/300, 322, 514/394
See application file for complete search history.

(56) References Cited

U.S. PATENT DOCUMENTS 9,963,448 B2 * 5/2018 Devraj .................... A61P 17/04

FOREIGN PATENT DOCUMENTS

| WO | WO2014015905 A1 | 1/2014 |
| WO | WO2016185279 A1 | 11/2016 |
| WO | WO2017100594 A1 | 6/2017 |
| WO | WO2017100601 A1 | 6/2017 |
| WO | WO2018022897 A1 | 2/2018 |
| WO | WO2018049296 A1 | 3/2018 |

OTHER PUBLICATIONS

Lewis, Huw D et al., "Inhibition of PAD4 activity is sufficient to disrupt mouse and human NET formation", Nature Chemical Biology, vol. 11 pp. 189-191 2015.
Berge et al., "Pharmaceutical Salts", Journal of Pharmaceutical Sciences, vol. 66(1), pp. 1-19 (1977).
Brinkmann et al., "Neutrophil extracellular traps kill bacteria", Science vol. 303(5663) pp. 1532-1535 ( 2004).
Chang, et al., "Increased PADI4 expression in blood and tissues of patients with malignant tumors", BMC Cancer, vol. 9(40), pp. 1-11 (2009).
Chumanevich, et al., "Suppression of colitis in mice by Cl-amidine: a novel peptidylarginine deiminase inhibitor", American J of Physiology, Gastrointestinal and Liver Physiology, vol. 300(6), pp. G929-G938 (2011).
Clark, et al., "Platelet TLR4 activates neutrophil extracellular traps to ensnare bacteria in septic blood", Nature Medicine, vol. 13(4), pp. 463-469 (2007).
Dworski et al., "Eosinophil and neutrophil extracellular DNA traps in human allergic asthmatic airways", The Journal of Allergy and Clinical Immunology, vol. 127(5), pp. 1260-1266 (2011).
Fuchs, et al., "Extracellular DNA traps promote thrombosis", PNAS, vol. 107(36), pp. 15880-15885 (2010).
Hakkim et al., "Impairment of neutrophil extracellular trap degradation is associated with lupus nephritis", PNAS, vol. 107(21), pp. 9813-9818 (2010).
ISR issued by USPTO for Application No. PCT/US2016/065857 mailed Apr. 17, 2017 (10 pages).
Jones et al., "Protein arginine deiminase 4 (PAD4): current understanding and future therapeutic potential", Current Opinion in Drug Discovery & Development, vol. 12(5), pp. 616-627 (2009).
Kessenbrock et al., "Netting neutrophils in autoimmune small-vessel vasculitis", Nature Medicine, vol. 15(6), pp. 623-625 (2009).
Kochi et al., "PADI4 polymorphism predisposes male smokers to rheumatoid arthritis", Annals of the Rheumatic Diseases, vol. 70(3), pp. 512-515 (2011).

(Continued)

*Primary Examiner* — Charanjit Aulakh
(74) *Attorney, Agent, or Firm* — Hong Liu

(57) ABSTRACT

The present invention provides compounds useful as inhibitors of PAD4, compositions thereof, and methods of treating PAD4-related disorders.

15 Claims, No Drawings

(56) References Cited

OTHER PUBLICATIONS

Lange et al., "Protein deiminases: New players in the developmentally regulated loss of neutral regenerative ability", Developmental Biology, vol. 355(2), 205-214 (2011).

Li et al., "PAD4 is essential for antibacterial innate immunity mediated by neutrophil extracellular traps", JEM, vol. 207(9), pp. 1853-1862 (2010).

Li et al., "Regulation of p53 Target Gene Expression by Peptidylarginine Deiminase 4", Molecular and Cellular Biology, vol. 28(15), pp. 4745-4758 (2008).

Lin et al., "Mast Cells and Neutrophils Release IL-17 through Extracellular Trip Formation in Psoriasis", The Journal of Immunology, vol. 187(1), pp. 490-500 (2011).

Neeli et al., "Histone Deimination as a Response to Inflammatory Stimuli in Neutrophils", The Journal of Immunology, vol. 108(3), pp. 1895-1902 (2008).

PubChem, "Substance Record for SID 1730220505," retrieved from http://pubchem.ncbi.nim.nih.gov/substance/173022050#section=Top accessed on Mar. 24, 2018 (5 pages).

Slack et al., "Protein Arginine Deiminase 4: a target for an epigenetic cancer therapy", Cellular and Molecular Life Sciences, vol. 68(4), pp. 709-720 (2011).

Villanueva et al., "Netting Neutrophils Induce Endothelial Damage, Infiltrate Tissues, and Expose Immunostimulatory Molecules in Systemic Lupus Erythematosus", The Journal of Immunology, vol. 187(1), pp. 538-552 (2011).

Vitkov et al., "Neutrophil Fate in Gingival Crevicular Fluid", Ultrastructrual Pathology, vol. 34(1), pp. 1-6 (2010).

Wegner et al., "Autoimmunity to specific citrullinated proteins gives the first clues to the etiology of rheumatoid arthritis", Immunological Reviews, vol. 233(1), pp. 34-54 (2010).

Willis et al., "N-a-Benzoyl-N5-(2-Chloro-1-Iminoethyl)-L-Ornithine Amide, a Protein Arginine Deiminase Inhibitor, Reduces the Severity of Murine Collagen-Induced Arthritis", The J. of Immunology, vol. 186(7), pp. 4396-4404 (2011).

\* cited by examiner

HETEROARYL INHIBITORS OF PAD4

CROSS REFERENCE TO RELATED APPLICATIONS

This application is a 371 application of PCT/US2017/018790, filed Feb. 22, 2017, which is entitled to priority pursuant to 35 U.S.C. § 119(e) to U.S. provisional patent application No. 62/298,726, filed Feb. 23, 2016, which is incorporated herein in its entirety.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an autoimmune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, Ann. Rheum. Dis., 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrulllination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med, 15(6), (2009), 623-625), systemic lupus erythematosus (Hakkim A. et al, Proc. Natl. Acad Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis, asthma (Dworski R. et al, J. Allergy Clin. Immunol., 127(5), (2011), 1260-6), deep vein thrombosis (Fuchs T. et al, Proc. Natl. Acad Sci. USA, 107(36), (2010), 15880-5), periodontitis (Vitkov L. et al, Ultrastructural Pathol., 34(1), (2010), 25-30), sepsis (Clark S. R. et al, Nat. Med, 13(4), (2007), 463-9), appendicitis (Brinkmann V. et al, Science, 303, (2004), 1532-5), and stroke. In addition, there is evidence that NETs may contribute to pathology in diseases affecting the skin, eg in cutaneous lupus erythematosis (Villanueva E. et al, J. Immunol., 187(1), (2011), 538-52) and psoriasis (Lin A. M. et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack. J. L. et al, Cell. Mol. Life Sci., 68(4), (2011), 709-720). Over-expression of PAD4 has been demonstrated in numerous cancers (Chang X et al, BMC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of formula I are useful as inhibitors of PAD4:

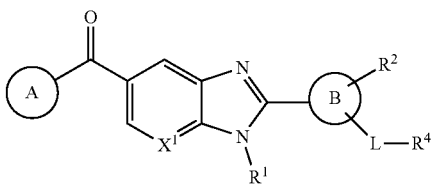

or a pharmaceutically acceptable salt thereof, wherein each of Ring A, Ring B, $R^1$, $R^2$, $R^3$, $X^1$, L, and $R^4$ is as defined and described herein.

It has also been found that compounds of formula I' are useful as inhibitors of PAD4:

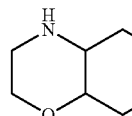

or a pharmaceutically acceptable salt thereof, wherein each of Ring A, Ring B, $R^1$, $R^2$, $R^3$, $X^1$, L, $R^4$ and n is as defined and described herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosis, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of formula I

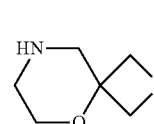

or a pharmaceutically acceptable salt thereof, wherein:
Ring A is

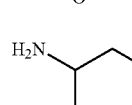

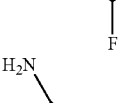

wherein Ring A is optionally substituted with 1-4 groups selected from fluorine, —CN, —OR, or $C_{1-6}$ aliphatic optionally substituted with 1-3 fluorine atoms;

Ring B is a 5-6 membered heteroaryl ring having 1-3 heteroatoms independently selected from nitrogen, oxygen, or sulfur;

$R^1$ is hydrogen, -Cy, or $C_6$ aliphatic optionally substituted with -Cy and optionally further substituted with 1-4 groups selected from fluorine, —CN, or —OR;

each -Cy is independently 4-7 membered saturated monocyclic ring having 0-2 heteroatoms independently selected from nitrogen, oxygen, or sulphur, wherein -Cy is optionally substituted with 1-4 groups selected from fluorine, —CN, or —OR;

$R^2$ is hydrogen, —CN, —OR, -Cy, or $C_{1/0}$ aliphatic optionally substituted with -Cy and optionally further substituted with 1-5 groups selected from fluorine, —CN, or —OR;

$X^1$ is N or $C(R^3)$ $R^3$ is —R or —OR;

each R is independently hydrogen or $C_{1-6}$ aliphatic optionally substituted with 1-3 fluorine atoms;

L is selected from a covalent bond or a $C_{1-6}$ membered straight or branched, saturated or unsaturated hydrocarbon chain wherein one methylene unit of L is optionally replaced by —C(O)N(R)—, wherein R is R or —CH$_2$phenyl; and $R^4$ is halogen, R, phenyl, or a 5-6-membered heteroaryl ring having 1-3 heteroatoms independently selected from nitrogen, oxygen, or sulphur, wherein $R^4$ is optionally substituted with 1-4 groups independently selected from halogen, —CN, —OR, or $C_{1-6}$ aliphatic optionally substituted with 1-3 fluorine atoms In some embodiments, such compounds include those of the formulae described herein, or a pharmaceutically acceptable salt thereof, wherein each variable is as defined herein and described in embodiments. Such compounds have the structure of formula I':

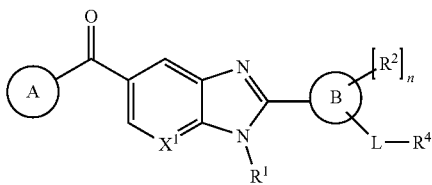

or a pharmaceutically acceptable salt thereof, wherein:
Ring A is

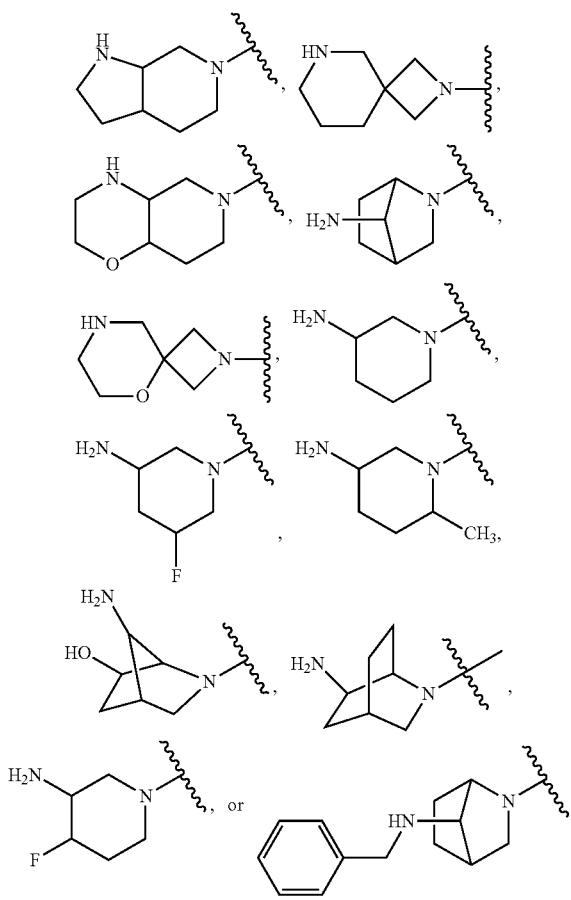

wherein Ring A is optionally substituted with 1-4 groups selected from fluorine, —CN, —OR, or $C_{1-6}$ aliphatic optionally substituted with 1-3 fluorine atoms;

Ring B is a 5-6 membered heteroaryl ring having 1-3 heteroatoms independently selected from nitrogen, oxygen, or sulfur;

$R^1$ is hydrogen, -Cy, or $C_{1-6}$ aliphatic optionally substituted with -Cy and optionally further substituted with 1-4 groups selected from fluorine, —CN, or —OR;

each -Cy is independently a 6-membered aryl ring containing 0-2 nitrogen atoms, or a 4-7 membered saturated monocyclic ring having 0-2 heteroatoms independently selected from nitrogen, oxygen, or sulphur, wherein -Cy is optionally substituted with 1-4 groups selected from fluorine, —CN, or —OR;

$R^2$ is hydrogen, —CN, —OR, -Cy, or $C_{1-10}$ aliphatic optionally substituted with -Cy and optionally further substituted with 1-5 groups selected from fluorine, —CN, or —OR; or: two $R^2$ groups on the same carbon atom are optionally taken together to form =O;

n is 1, 2, or 3;

$X^1$ is N or CR3)

$R^3$ is —R, halogen, or —OR;

each R is independently hydrogen or $C_{1-6}$ aliphatic optionally substituted with 1-3 fluorine atoms;

L is selected from a covalent bond or a $C_{1-6}$ membered straight or branched, saturated or unsaturated hydrocarbon chain wherein one methylene unit of L is optionally replaced by —S(O)$_2$— or —C(O)N(R$^y$)—, wherein R is R or —CH$_2$phenyl; and $R^4$ is halogen, R, phenyl, or a 5-6-membered heteroaryl ring having 1-3 heteroatoms independently selected from nitrogen, oxygen, or sulphur, wherein $R^4$ is optionally substituted with 1-4 groups independently selected from halogen, —CN, —OR, —C(O)OH, or $C_1$. 6 aliphatic optionally substituted with 1-3 fluorine atoms.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or $^{14}$C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

3. Description of Exemplary Compounds

According to one aspect, the present invention provides a compound of formula I:

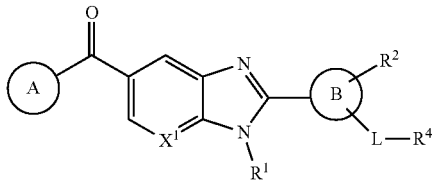

or a pharmaceutically acceptable salt thereof, wherein:
Ring A is

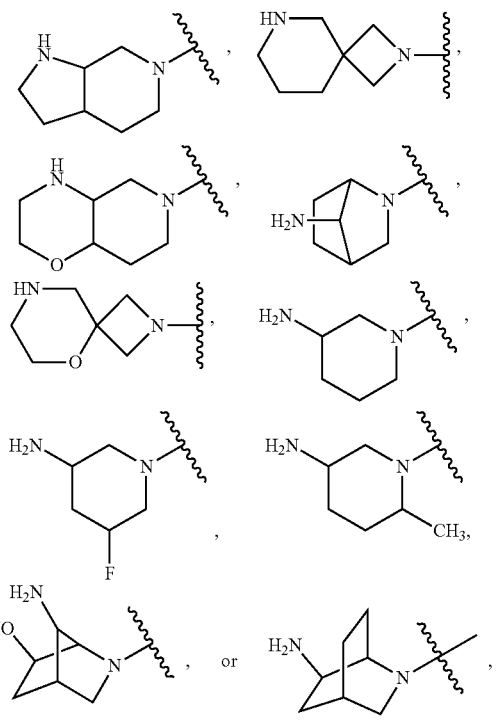

wherein Ring A is optionally substituted with 1-4 groups selected from fluorine, —CN, —OR, or $C_{1-6}$ aliphatic optionally substituted with 1-3 fluorine atoms;

Ring B is a 5-6 membered heteroaryl ring having 1-3 heteroatoms independently selected from nitrogen, oxygen, or sulfur;

$R^1$ is hydrogen, -Cy, or $C_{1-6}$ aliphatic optionally substituted with -Cy and optionally further substituted with 1-4 groups selected from fluorine, —CN, or —OR;

each -Cy is independently 4-7 membered saturated monocyclic ring having 0-2 heteroatoms independently selected from nitrogen, oxygen, or sulphur, wherein -Cy is optionally substituted with 1-4 groups selected from fluorine, —CN, or —OR;

$R^2$ is hydrogen, —CN, —OR, -Cy, or $C_{1-10}$ aliphatic optionally substituted with -Cy and optionally further substituted with 1-5 groups selected from fluorine, —CN, or —OR;

$X^1$ is N or $C(R^3)$ $R^3$ is —R or —OR;

each R is independently hydrogen or $C_{1-6}$ aliphatic optionally substituted with 1-3 fluorine atoms;

L is selected from a covalent bond or a $C_{1-6}$ membered straight or branched, saturated or unsaturated hydrocarbon chain wherein one methylene unit of L is optionally replaced by —C(O)N(R)—, wherein R is R or —CH$_2$phenyl; and R$^4$ is halogen, R, phenyl, or a 5-6-membered heteroaryl ring having 1-3 heteroatoms independently selected from nitrogen, oxygen, or sulphur, wherein R$^4$ is optionally substituted with 1-4 groups independently selected from halogen, —CN, —OR, C$_{1-6}$ aliphatic optionally substituted with 1-3 fluorine atoms.

According to another aspect, the present invention provides a compound of formula I':

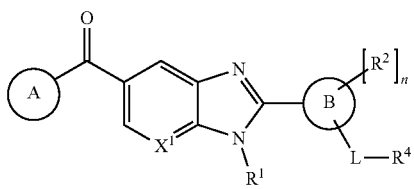

or a pharmaceutically acceptable salt thereof, wherein:
Ring A is

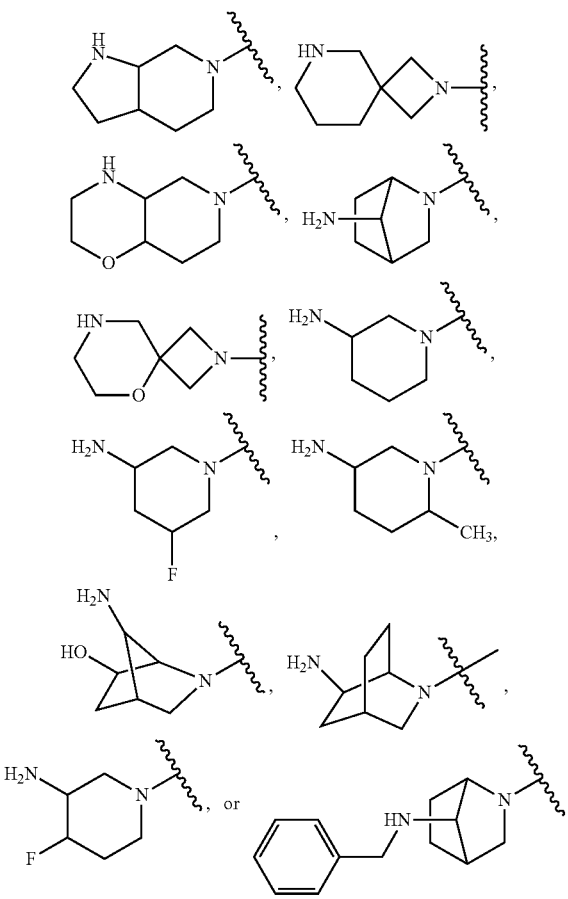

wherein Ring A is optionally substituted with 1-4 groups selected from fluorine, —CN, —OR, or C$_{1-6}$ aliphatic optionally substituted with 1-3 fluorine atoms;

Ring B is a 5-6 membered heteroaryl ring having 1-3 heteroatoms independently selected from nitrogen, oxygen, or sulfur;

R$^1$ is hydrogen, -Cy, or C$_{1-6}$ aliphatic optionally substituted with -Cy and optionally further substituted with 1-4 groups selected from fluorine, —CN, or —OR;

each -Cy is independently a 6-membered aryl ring containing 0-2 nitrogen atoms, or a 4-7 membered saturated monocyclic ring having 0-2 heteroatoms independently selected from nitrogen, oxygen, or sulphur, wherein -Cy is optionally substituted with 1-4 groups selected from fluorine, —CN, or —OR;

R$^2$ is hydrogen, —CN, —OR, -Cy, or C$_{1/0}$ aliphatic optionally substituted with -Cy and optionally further substituted with 1-5 groups selected from fluorine, —CN, or —OR; or:

two R$^2$ groups on the same carbon atom are optionally taken together to form =O;

n is 1, 2, or 3;

X$^1$ is N or C(R$^3$)

R$^3$ is —R, halogen, or —OR;

each R is independently hydrogen or C$_{1-6}$ aliphatic optionally substituted with 1-3 fluorine atoms;

L is selected from a covalent bond or a C$_{1-6}$ membered straight or branched, saturated or unsaturated hydrocarbon chain wherein one methylene unit of L is optionally replaced by —S(O)$_2$— or —C(O)N(R$^3$')—, wherein R is R or —CH$_2$phenyl; and R$^4$ is halogen, R, phenyl, or a 5-6-membered heteroaryl ring having 1-3 heteroatoms independently selected from nitrogen, oxygen, or sulphur, wherein R$^4$ is optionally substituted with 1-4 groups independently selected from halogen, —CN, —OR, —C(O)OH, or C$_{1-6}$ aliphatic optionally substituted with 1-3 fluorine atoms.

As defined above, X$^1$ is N or C(R$^3$). In some embodiments, X$^1$ is N. In some embodiments, X$^1$ is C(R$^3$). In certain embodiments, the present invention provides a compound of formula I-a or I-b:

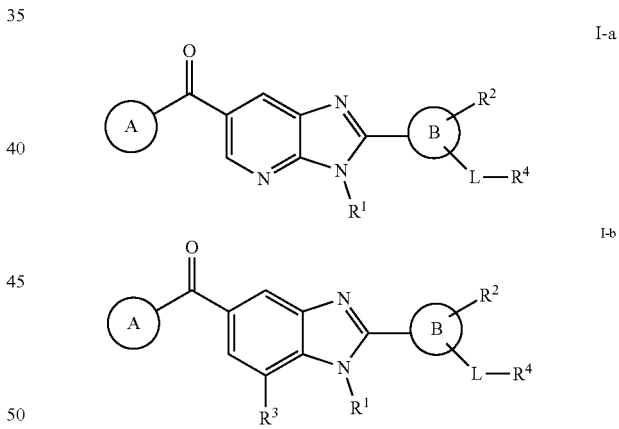

or a pharmaceutically acceptable salt thereof, wherein each of Ring A, Ring B, R$^1$, R$^2$, R$^3$, L, and R$^4$ is as defined and described herein.

In certain embodiments, the present invention provides a compound of formula I'-a or I'-b:

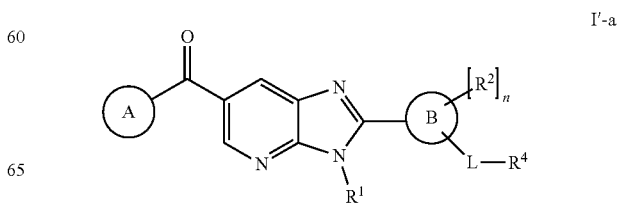

-continued

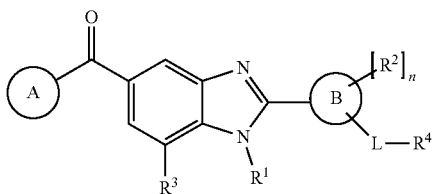

I'-b or a pharmaceutically acceptable salt thereof, wherein each of Ring A, Ring B, $R^1$, $R^2$, $R^3$, L, $R^4$ and n is as defined and described herein.

As defined above and described herein, $R^1$ is hydrogen, -Cy, or $C_{1-6}$ aliphatic optionally substituted with -Cy and optionally further substituted with 1-4 groups selected from fluorine, —CN, or —OR; each -Cy is independently 4-7 membered saturated monocyclic ring having 0-2 heteroatoms independently selected from nitrogen, oxygen, or sulphur, wherein -Cy is optionally substituted with 1-4 groups selected from fluorine, —CN, or —OR.

In some embodiments, $R^1$ is hydrogen. In some embodiments, $R^1$ is -Cy. In some embodiments, R is $C_{1-6}$ aliphatic optionally substituted with 1-4 groups selected from fluorine, —CN, or —OR. In some embodiments, R is $C_{1-3}$ aliphatic. In some embodiments, $R^1$ is methyl. In some embodiments, $R^1$ is ethyl. In some embodiments, $R^1$ is propyl. In some embodiments, $R^1$ is —CH$_2$-cyclobutyl optionally substituted with methyl and —OH. In some embodiments, each-Cy is independently a 4-7 membered saturated monocyclic ring having 0-2 heteroatoms independently selected from nitrogen, oxygen or sulphur. In some embodiments, -Cy is optionally substituted with 1-4 groups selected from fluorine, —CN, or —OR. In some embodiments, -Cy is phenyl. In some embodiments, -Cy is pyridyl.

In some embodiments, -Cy is a 6-membered aryl ring containing 0-2 nitrogen atoms.

In some embodiments, $R^1$ is phenyl. In some embodiments, R is

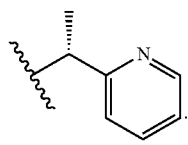 [SMILES: *[C@H](C)c1ccccn1]

In some embodiments, $R^1$ is

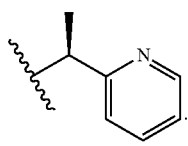 [SMILES: *[C@@H](C)c1ccccn1]

In some embodiments, $R^1$ is

As defined above and described herein, $R^2$ is hydrogen, —CN, —OR, -Cy, or $C_{1/0}$ aliphatic optionally substituted with -Cy and optionally further substituted with 1-5 groups selected from fluorine, —CN, or —OR. In some embodiments, $R^2$ is hydrogen. In some embodiments, $R^2$ is $C_{1-10}$ aliphatic optionally substituted with 1-5 groups selected from fluorine, —CN, or —OR. In some embodiments, $R^2$ is $C_{1-10}$ aliphatic optionally substituted with -Cy and optionally further substituted with 1-5 groups selected from fluorine, —CN, or —OR. In some embodiments, $R^2$ is -Cy. In some embodiments, $R^2$ is methyl. In some embodiments, $R^2$ is ethyl. In some embodiments, $R^2$ is propyl. In some embodiments, $R^2$ is butyl. In some embodiments, $R^2$ is pentyl. In some embodiments, $R^2$ is hexyl. In some embodiments, $R^2$ is cyclopropyl. In some embodiments, $R^2$ is cyclobutyl. In some embodiments, $R^2$ is cyclopentyl. In some embodiments, $R^2$ is cyclohexyl. In some embodiments, $R^2$ is cyclopropylmethyl. In some embodiments, $R^2$ is cyclobutylmethyl. In some embodiments, $R^2$ is cyclopentylmethyl. In some embodiments, $R^2$ is cyclohexylmethyl. In some embodiments, $R^2$ is cyclopropylethyl. In some embodiments, $R^2$ is cyclobutylethyl. In some embodiments, $R^2$ is cyclopentylethyl. In some embodiments, $R^2$ is cyclohexylethyl. In some embodiments, $R^2$ is —CH$_2$-cyclopropyl or —CH$_2$-cyclobutyl. In some embodiments, $R^1$ is —CH$_2$-cyclobutyl optionally substituted with methyl and —OH. In some embodiments, $R^1$ is selected from those depicted in Table 1, below.

In some embodiments, $R^2$ is $C_{1-10}$ aliphatic, substituted with 1-5 fluorine atoms. In some embodiments, $R^2$ is $C_{1-10}$ aliphatic, substituted with 1-5 fluorine atoms. In some embodiments, $R^2$ is $C_{1-10}$ aliphatic, substituted with 1 fluorine atom. In some embodiments, $R^2$ is $C_{1-10}$ aliphatic, substituted with 2 fluorine atoms. In some embodiments, $R^2$ is $C_{1-10}$ aliphatic, substituted with 3 fluorine atoms. In some embodiments, $R^2$ is $C_{1-10}$ aliphatic, substituted with 4 fluorine atoms. In some embodiments, $R^2$ is $C_{1-10}$ aliphatic, substituted with 5 fluorine atoms. In some embodiments, $R^2$ is methyl, substituted with 1-3 fluorine atoms. In some embodiments, $R^2$ is trifluoromethyl. In some embodiments, $R^2$ is ethyl, substituted with 1-5 fluorine atoms. In some embodiments, $R^2$ is 2,2,2-trifluoroethyl. In some embodiments, $R^2$ is propyl, substituted with 1-5 fluorine atoms. In some embodiments, $R^2$ is 3,3,3-trifluoropropyl. In some embodiments, $R^2$ is butyl, substituted with 1-5 fluorine atoms. In some embodiments, $R^2$ is 4,4,4-trifluorobutyl. In some embodiments, $R^2$ is pentyl, substituted with 1-5 fluorine atoms. In some embodiments, $R^2$ is 5,5,5-trifluoropentyl. In some embodiments, $R^2$ is hexyl, substituted with 1-5 fluorine atoms. In some embodiments, $R^2$ is 6,6,6-trifluorohexyl. In some embodiments, $R^2$ is selected from those depicted in Table 1, below.

In some embodiments, $R^2$ is phenyl. In some embodiments, $R^2$ is n-propyl. In some embodiments, $R^2$ is isopropyl. In some embodiments, $R^2$ is pyridyl. In some embodiments, $R^2$ is fluoro. In some embodiments, $R^2$ is bromo. In some embodiments, $R^2$ is benzyl. In some embodiments, $R^2$ is -Ome. In some embodiments, $R^2$ is —OH. In some embodiments, $R^2$ is —CN. In some embodiments, two $R^2$ groups are taken together to form =O.

In some embodiments, $R^2$ is

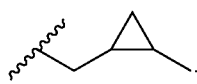

In some embodiments, R² is

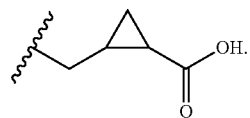

In some embodiments, R² is

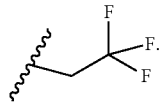 [SMILES: *CC(F)(F)F]

In some embodiments, R² is

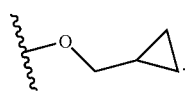 [SMILES: *OCC1CC1]

In some embodiments, R² is

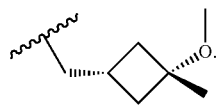 [SMILES: *C[C@H]1C[C@@](C)(OC)C1]

In some embodiments, R² is

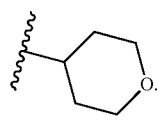

In some embodiments, R² is

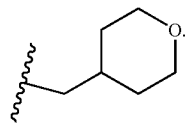 [SMILES: *CC1CCOCC1]

In some embodiments, R² is

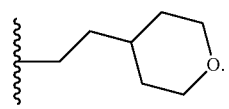 [SMILES: *CCC1CCOCC1]

In some embodiments, R² is

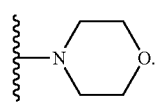

In some embodiments, R² is

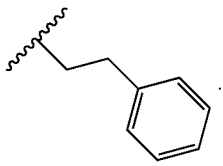 [SMILES: *CCc1ccccc1]

In some embodiments, R² is

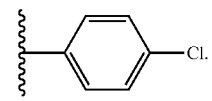

In some embodiments, R² is

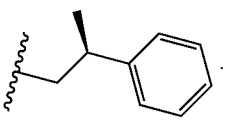 [SMILES: *C[C@@H](C)c1ccccc1]

In some embodiments, R²

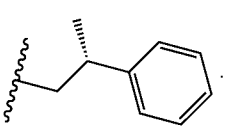

In some embodiments, R² is

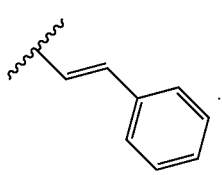 [SMILES: */C=C/c1ccccc1]

In some embodiments, R² is

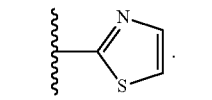

In some embodiments, R² is

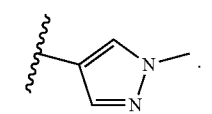 [SMILES: *c1cnn(C)c1]

In some embodiments, R² is

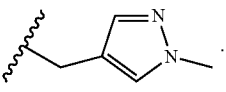

In some embodiments, R² is

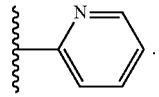

In some embodiments, R² is

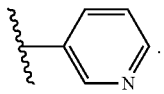 [SMILES: *c1cccnc1]

In some embodiments, R² is

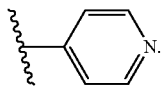

In some embodiments, R² is

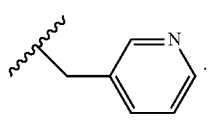 [SMILES: *Cc1cccnc1]

In some embodiments, R² is

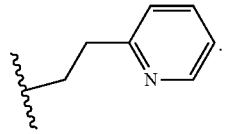

As defined above and described herein, R³ is —R or —OR. In some embodiments, R³ is hydrogen. In some embodiments, R³ is $C_{1-6}$ aliphatic optionally substituted with 1-3 fluorine atoms. In some embodiments, R³ is —OCH₃. In some embodiments, R³ is selected from those depicted in Table 1, below.

In some embodiments, R³ is halogen. In some embodiments, R³ is fluoro.

As defined above, Ring A is

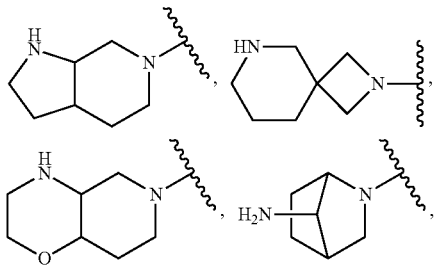

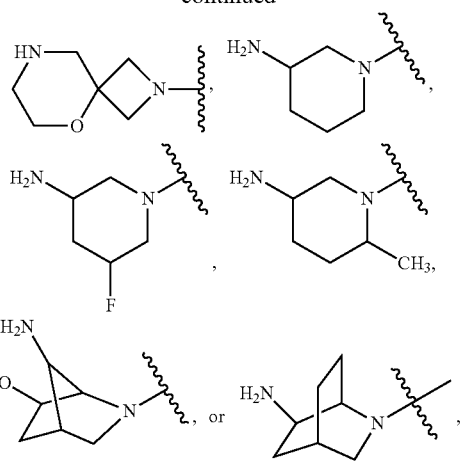

wherein Ring A is optionally substituted with 1-4 groups selected from fluorine, —CN, —OR, or $C_{1-6}$ aliphatic optionally substituted with 1-3 fluorine atoms.

In some embodiments, Ring A is selected from or In

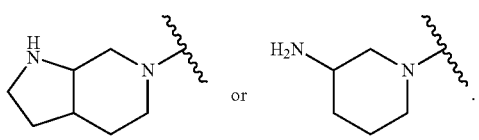 [SMILES: *N1CCC2CCNC2C1 ; *N1CCCC(N)C1]

In some embodiments, Ring A is

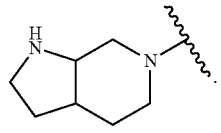 [SMILES: *N1CCC2CCNC2C1]

In some embodiments, Ring A is

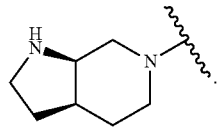 [SMILES: *N1CC[C@H]2CCN[C@H]2C1]

In some embodiments, Ring A is

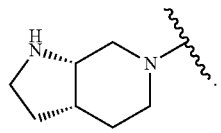 [SMILES: *N1CC[C@@H]2CCN[C@@H]2C1]

In some embodiments, Ring A is

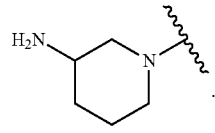 [SMILES: *N1CCCC(N)C1]

In some embodiments, Ring A is

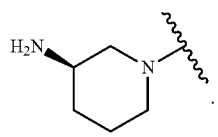

In some embodiments, Ring A is

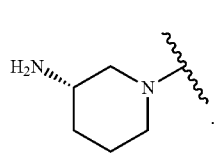

In some embodiments, Ring A is

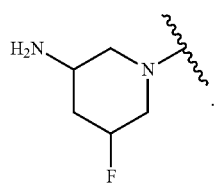

In some embodiments, Ring A is

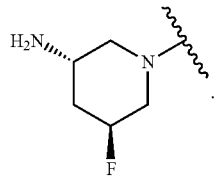

In some embodiments, Ring A is

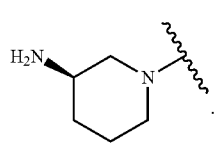

In some embodiments, Ring A is

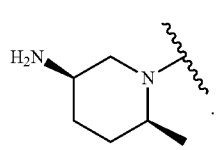

In some embodiments, Ring A is

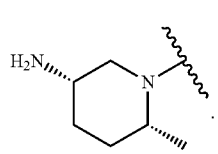

In some embodiments, Ring A is

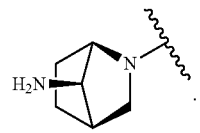

In some embodiments, Ring A is

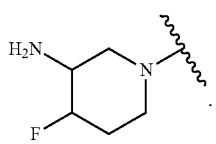 [SMILES: *N1CCC(F)C(N)C1]

In some embodiments, Ring A is

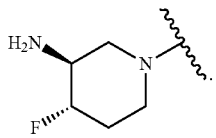

In some embodiments, Ring A is

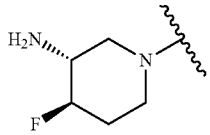

In some embodiments, Ring A is

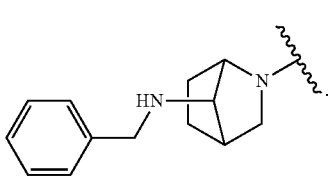 [SMILES: *N1CC2CCC1C2NCc1ccccc1]

In some embodiments, Ring A is

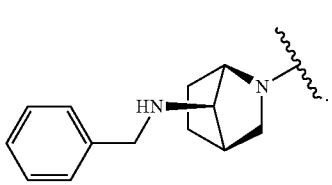 [SMILES: *N1C[C@H]2CC[C@@H]1[C@@H]2NCc1ccccc1]

In some embodiments, Ring A is selected from those depicted in Table 1, below.

In some embodiments, Ring B is a 5-membered heteroaryl ring having 1-3 heteroatoms independently selected from nitrogen, oxygen, or sulfur. In other embodiments, Ring B is a 6-membered heteroaryl ring having 1-2 nitrogens.

In some embodiments, Ring B is imidazolyl, pyrazolyl, pyrrolyl, pyridyl, or thiazolyl. In some embodiments, Ring B is imidazolyl, pyrazolyl, pyrrolyl, or thiazolyl. In some embodiments, Ring B is pyridyl. In some embodiments, Ring B is selected from those depicted in Table 1, below.

In some embodiments, Ring B is pyrrolyl. In some embodiments, Ring B is

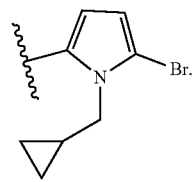 [SMILES: *c1ccc(Br)n1CC1CC1]

In some embodiments, Ring B is

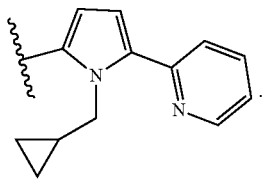 [SMILES: *c1ccc(-c2ccccn2)n1CC1CC1]

In some embodiments, Ring B is

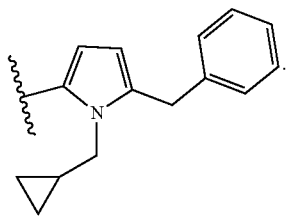 [SMILES: *c1ccc(Cc2ccccc2)n1CC1CC1]

In some embodiments, Ring B is

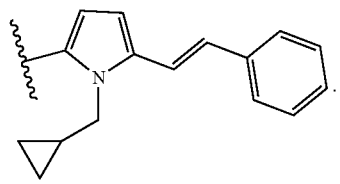 [SMILES: *c1ccc(/C=C/c2ccccc2)n1CC1CC1]

In some embodiments, Ring B

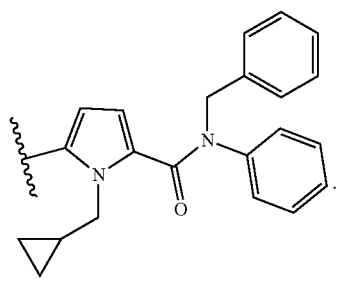 [SMILES: *c1ccc(C(=O)N(Cc2ccccc2)c2ccccc2)n1CC1CC1]

In some embodiments, Ring B is imidazolyl. In some embodiments, Ring B is

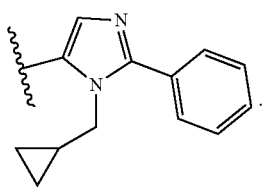 [SMILES: *c1cnc(-c2ccccc2)n1CC1CC1]

In some embodiments, Ring B is phenylenyl. In some embodiments, Ring B is pyridonenyl. In some embodiments, Ring B is pyridinyl. In some embodiments, Ring B is pyrrolenyl. In some embodiments, Ring B is pyazolenyl. In some embodiments, Ring B is thiazolenyl.

In some embodiments, Ring B with its $R^2$ and -L-$R^4$ substituents is

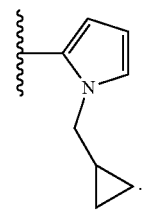 [SMILES: *c1cccn1CC1CC1]

In some embodiments, Ring B with its $R^2$ and -L-$R^4$ substituents is

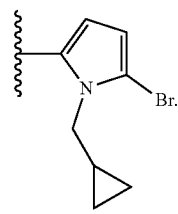 [SMILES: *c1ccc(Br)n1CC1CC1]

In some embodiments, Ring B with its $R^2$ and -L-$R^4$ substituents is

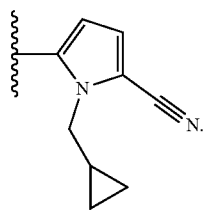 [SMILES: *c1ccc(C#N)n1CC1CC1]

In some embodiments, Ring B with its $R^2$ and -L-$R^4$ substituents is

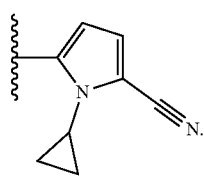 [SMILES: *c1ccc(C#N)n1C1CC1]

In some embodiments, Ring B with its $R^2$ and -L-$R^4$ substituents is

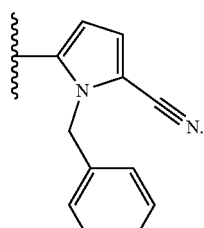

In some embodiments, Ring B with its $R^2$ and -L-$R^4$ substituents is

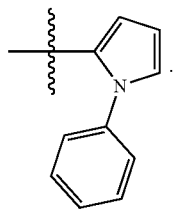 [SMILES: *c1cccn1-c1ccccc1]

In some embodiments, Ring B with its $R^2$ and -L-$R^4$ substituents is

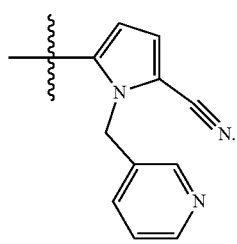 [SMILES: *c1ccc(C#N)n1Cc1cccnc1]

In some embodiments, Ring B with its $R^2$ and -L-$R^4$ substituents is

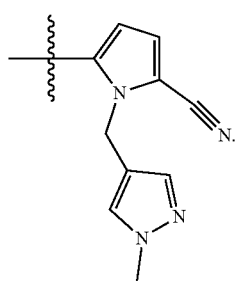 [SMILES: *c1ccc(C#N)n1Cc1cnn(C)c1]

In some embodiments, Ring B with its $R^2$ and -L-$R^4$ substituents is

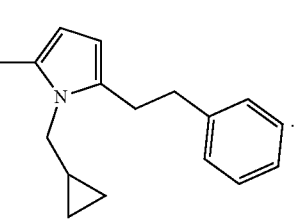

In some embodiments, Ring B with its $R^2$ and -L-$R^4$ substituents is

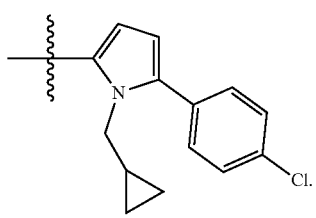 [SMILES: *c1ccc(-c2ccc(Cl)cc2)n1CC1CC1]

In some embodiments, Ring B with its $R^2$ and -L-$R^4$ substituents is

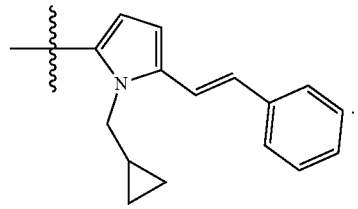 [SMILES: *c1ccc(/C=C/c2ccccc2)n1CC1CC1]

In some embodiments, Ring B with its $R^2$ and -L-$R^4$ substituents is

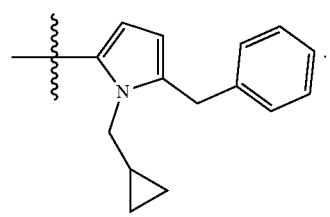 [SMILES: *c1ccc(Cc2ccccc2)n1CC1CC1]

In some embodiments, Ring B with its $R^2$ and -L-$R^4$ substituents is

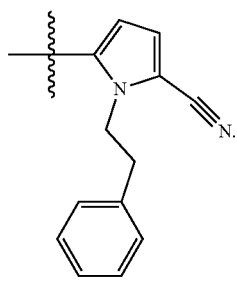 [SMILES: *c1ccc(C#N)n1CCc1ccccc1]

In some embodiments, Ring B with its $R^2$ and -L-$R^4$ substituents is

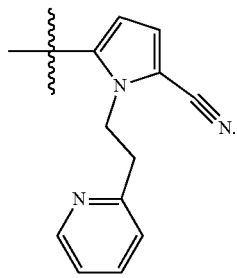 [SMILES: *c1ccc(C#N)n1CCc1ccccn1]

In some embodiments, Ring B with its $R^2$ and -L-$R^4$ substituents is

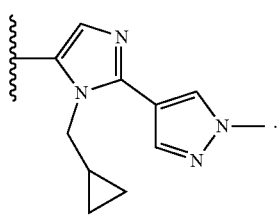 [SMILES: *c1cnc(-c2cnn(C)c2)n1CC1CC1]

In some embodiments, Ring B with its $R^2$ and -L-$R^4$ substituents is

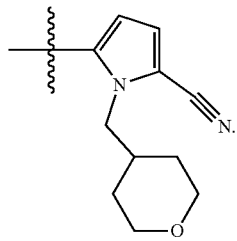 [SMILES: *c1ccc(C#N)n1CC1CCOCC1]

In some embodiments, Ring B with its $R^2$ and -L-$R^4$ substituents is

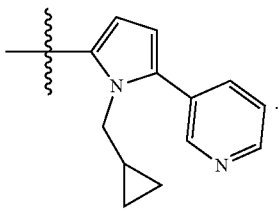 [SMILES: *c1ccc(-c2cccnc2)n1CC1CC1]

In some embodiments, Ring B with its $R^2$ and -L-$R^4$ substituents is

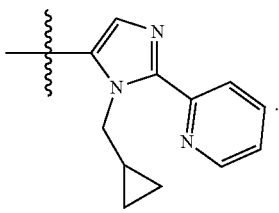 [SMILES: *c1cnc(-c2ccccn2)n1CC1CC1]

In some embodiments, Ring B with its $R^2$ and -L-$R^4$ substituents is

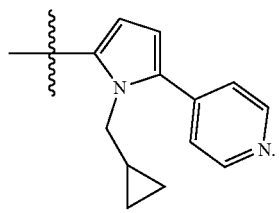 [SMILES: *c1ccc(-c2ccncc2)n1CC1CC1]

In some embodiments, Ring B with its $R^2$ and -L-$R^4$ substituents is

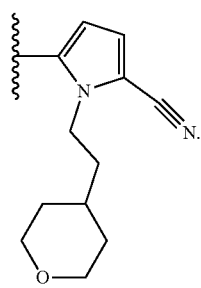 [SMILES: *c1ccc(C#N)n1CCC1CCOCC1]

In some embodiments, Ring B with its $R^2$ and -L-$R^4$ substituents is

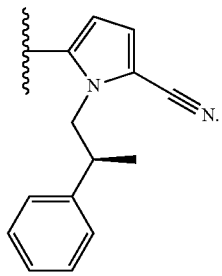 [SMILES: *c1ccc(C#N)n1C[C@@H](C)c1ccccc1]

In some embodiments, Ring B with its $R^2$ and -L-$R^4$ substituents is

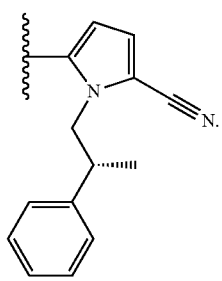 [SMILES: *c1ccc(C#N)n1C[C@H](C)c1ccccc1]

In some embodiments, Ring B with its $R^2$ and -L-$R^4$ substituents is

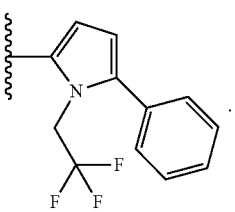 [SMILES: *c1ccc(-c2ccccc2)n1CC(F)(F)F ; "."]

In some embodiments, Ring B with its $R^2$ and -L-$R^4$ substituents is

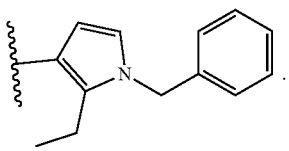 [SMILES: *c1ccn(Cc2ccccc2)c1CC ; "."]

In some embodiments, Ring B with its $R^2$ and -L-$R^4$ substituents is

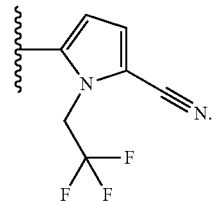 [SMILES: *c1ccc(C#N)n1CC(F)(F)F]

In some embodiments, Ring B with its $R^2$ and -L-$R^4$ substituents is

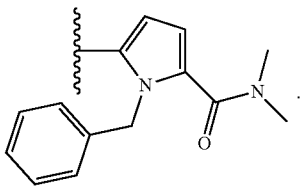 [SMILES: *c1ccc(C(=O)N(C)C)n1Cc1ccccc1 ; "."]

In some embodiments, Ring B with its $R^2$ and -L-$R^4$ substituents is

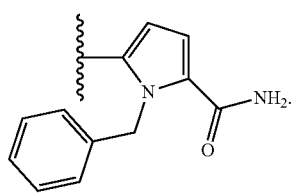 [SMILES: *c1ccc(C(N)=O)n1Cc1ccccc1]

In some embodiments, Ring B with its $R^2$ and -L-$R^4$ substituents is

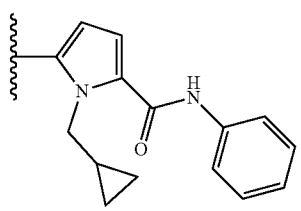

In some embodiments, Ring B with its $R^2$ and -L-$R^4$ substituents is

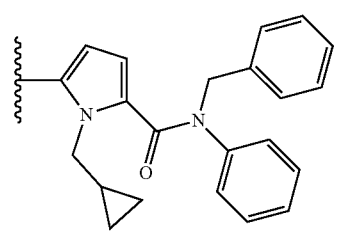

In some embodiments, Ring B with its $R^2$ and -L-$R^4$ substituents is

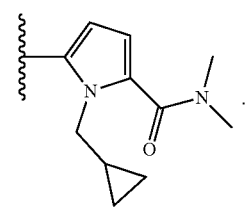 [SMILES: *c1ccc(C(=O)N(C)C)n1CC1CC1 ; "."]

In some embodiments, Ring B with its $R^2$ and -L-$R^4$ substituents is

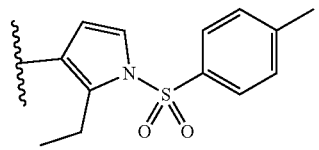

In some embodiments, Ring B with its $R^2$ and -L-$R^4$ substituents is

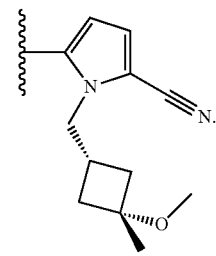 [SMILES: *c1ccc(C#N)n1C[C@H]1C[C@@](C)(OC)C1]

In some embodiments, Ring B with its $R^2$ and -L-$R^4$ substituents is

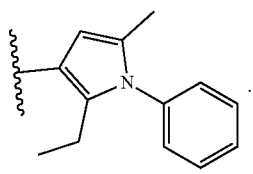 [SMILES: *c1cc(C)n(-c2ccccc2)c1CC ; "."]

In some embodiments, Ring B with its $R^2$ and -L-$R^4$ substituents is

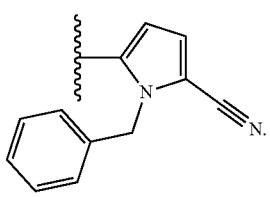 [SMILES: *c1ccc(C#N)n1Cc1ccccc1]

In some embodiments, Ring B with its $R^2$ and -L-$R^4$ substituents is

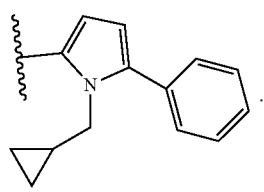 [SMILES: *c1ccc(-c2ccccc2)n1CC1CC1 ; "."]

In some embodiments, Ring B with its $R^2$ and -L-$R^4$ substituents is

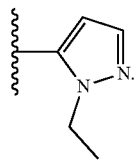

In some embodiments, Ring B with its $R^2$ and -L-$R^4$ substituents is

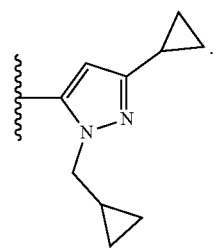 [SMILES: *c1cc(C2CC2)nn1CC1CC1]

In some embodiments, Ring B with its $R^2$ and -L-$R^4$ substituents is

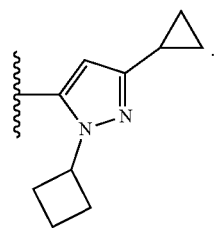 [SMILES: *c1cc(C2CC2)nn1C1CCC1]

In some embodiments, Ring B with its $R^2$ and -L-$R^4$ substituents is

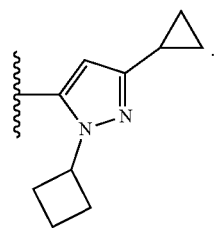 [SMILES: *c1cc(C2CC2)nn1C1CCC1]

In some embodiments, Ring B with its $R^2$ and -L-$R^4$ substituents is

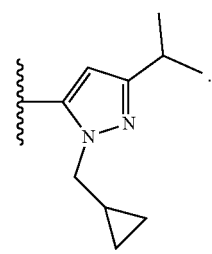 [SMILES: *c1cc(C(C)C)nn1CC1CC1]

In some embodiments, Ring B with its $R^2$ and -L-$R^4$ substituents is

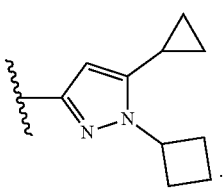 [SMILES: *c1cc(C2CC2)n(C2CCC2)n1]

In some embodiments, Ring B with its $R^2$ and -L-$R^4$ substituents is

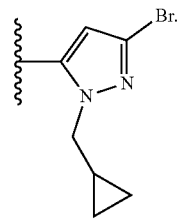 [SMILES: *c1cc(Br)nn1CC1CC1]

In some embodiments, Ring B with its $R^2$ and -L-$R^4$ substituents is

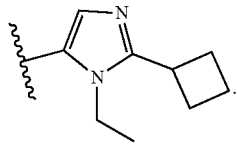 [SMILES: *c1cnc(C2CCC2)n1CC]

In some embodiments, Ring B with its $R^2$ and -L-$R^4$ substituents is

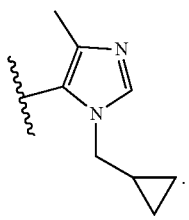 [SMILES: *c1c(C)ncn1CC1CC1]

In some embodiments, Ring B with its $R^2$ and -L-$R^4$ substituents is

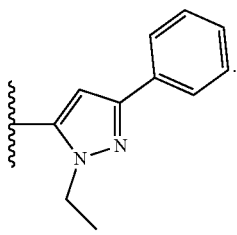 [SMILES: *c1cc(-c2ccccc2)nn1CC]

In some embodiments, Ring B with its $R^2$ and -L-$R^4$ substituents is

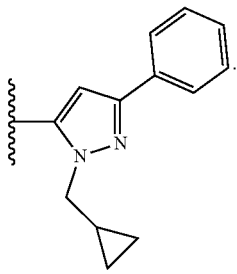 [SMILES: *c1cc(-c2ccccc2)nn1CC1CC1]

In some embodiments, Ring B with its $R^2$ and -L-$R^4$ substituents is

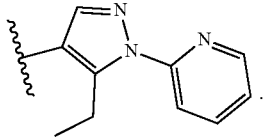 [SMILES: *c1cnn(-c2ccccn2)c1CC]

In some embodiments, Ring B with its $R^2$ and -L-$R^4$ substituents is

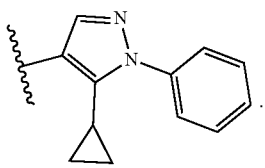 [SMILES: *c1cnn(-c2ccccc2)c1C1CC1]

In some embodiments, Ring B with its $R^2$ and -L-$R^4$ substituents is

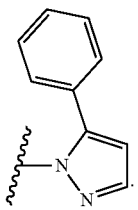 [SMILES: *n1nccc1-c1ccccc1]

In some embodiments, Ring B with its $R^2$ and -L-$R^4$ substituents is

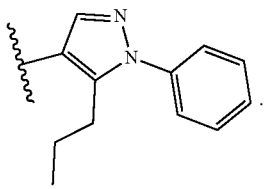 [SMILES: *c1cnn(-c2ccccc2)c1CCC]

In some embodiments, Ring B with its $R^2$ and -L-$R^4$ substituents is

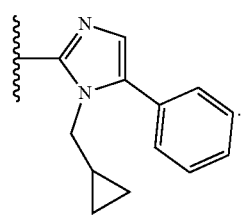 [SMILES: *c1ncc(-c2ccccc2)n1CC1CC1]

In some embodiments, Ring B with its $R^2$ and -L-$R^4$ substituents is

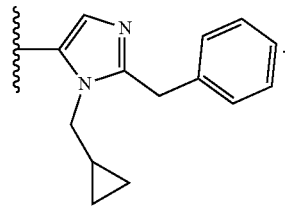 [SMILES: *c1cnc(Cc2ccccc2)n1CC1CC1]

In some embodiments, Ring B with its $R^2$ and -L-$R^4$ substituents is

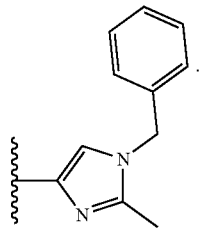 [SMILES: *c1cn(Cc2ccccc2)c(C)n1]

In some embodiments, Ring B with its $R^2$ and -L-$R^4$ substituents is

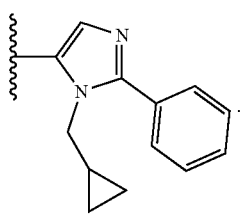 [SMILES: *c1cnc(-c2ccccc2)n1CC1CC1]

In some embodiments, Ring B with its $R^2$ and -L-$R^4$ substituents is

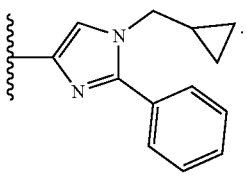 [SMILES: *c1cn(CC2CC2)c(-c2ccccc2)n1]

In some embodiments, Ring B with its $R^2$ and -L-$R^4$ substituents is

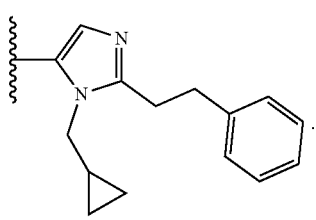 [SMILES: *c1cnc(CCc2ccccc2)n1CC1CC1]

In some embodiments, Ring B with its R² and -L-R⁴ substituents is

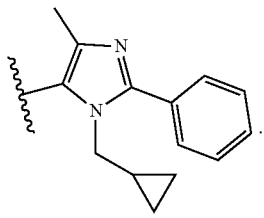 [SMILES: *c1c(C)nc(-c2ccccc2)n1CC1CC1]

In some embodiments, Ring B with its R² and -L-R⁴ substituents is

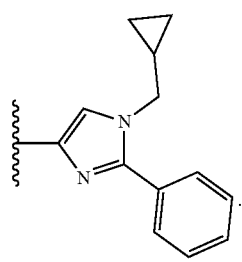 [SMILES: *c1cn(CC2CC2)c(-c2ccccc2)n1]

In some embodiments, Ring B with its R² and -L-R⁴ substituents is

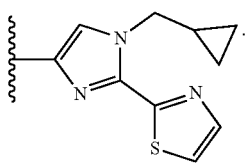 [SMILES: *c1cn(CC2CC2)c(-c2nccs2)n1]

In some embodiments, Ring B with its R² and -L-R⁴ substituents is

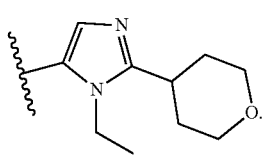 [SMILES: *c1cnc(C2CCOCC2)n1CC]

In some embodiments, Ring B with its R² and -L-R⁴ substituents is

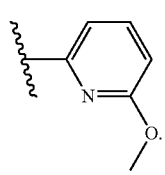 [SMILES: *c1cccc(OC)n1]

In some embodiments, Ring B with its R² and -L-R⁴ substituents is

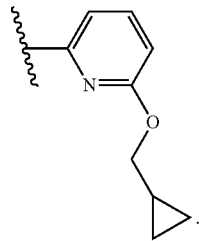 [SMILES: *c1cccc(OCC2CC2)n1]

In some embodiments, Ring B with its R² and -L-R⁴ substituents is

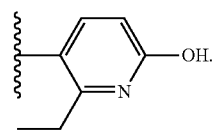

In some embodiments, Ring B with its R² and -L-R⁴ substituents is

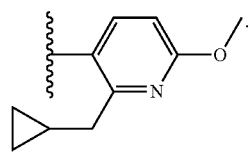 [SMILES: *c1ccc(OC)nc1CC1CC1]

In some embodiments, Ring B with its R² and -L-R⁴ substituents is

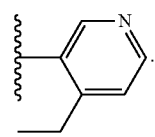

In some embodiments, Ring B with its R² and -L-R⁴ substituents is

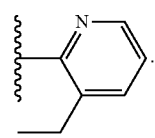

In some embodiments, Ring B with its R² and -L-R⁴ substituents is

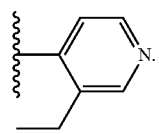

In some embodiments, Ring B with its $R^2$ and -L-$R^4$ substituents is

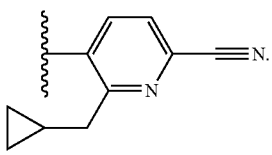 [SMILES: *c1ccc(C#N)nc1CC1CC1]

In some embodiments, Ring B with its $R^2$ and -L-$R^4$ substituents is

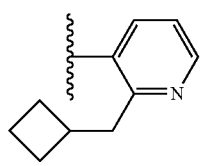

In some embodiments, Ring B with its $R^2$ and -L-$R^4$ substituents is

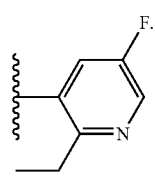 [SMILES: *c1cc(F)cnc1CC]

In some embodiments, Ring B with its $R^2$ and -L-$R^4$ substituents is

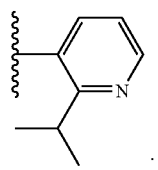 [SMILES: *c1cccnc1C(C)C]

In some embodiments, Ring B with its $R^2$ and -L-$R^4$ substituents is

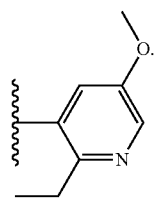 [SMILES: *c1cc(OC)cnc1CC]

In some embodiments, Ring B with its $R^2$ and -L-$R^4$ substituents is

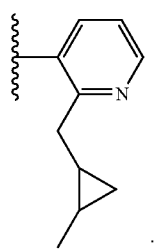 [SMILES: *c1cccnc1CC1CC1C]

In some embodiments, Ring B with its $R^2$ and -L-$R^4$ substituents is

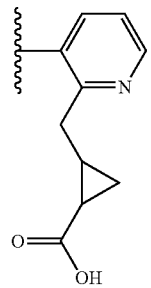

In some embodiments, Ring B with its $R^2$ and -L-$R^4$ substituents is

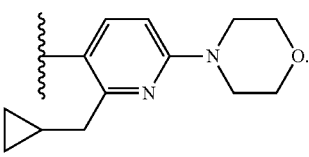 [SMILES: *c1ccc(N2CCOCC2)nc1CC1CC1]

In some embodiments, Ring B with its $R^2$ and -L-$R^4$ substituents is

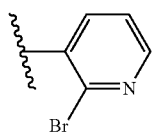

In some embodiments, Ring B with its $R^2$ and -L-$R^4$ substituents is

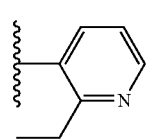

In some embodiments, Ring B with its $R^2$ and -L-$R^4$ substituents is

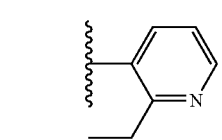

In some embodiments, Ring B with its $R^2$ and -L-$R^4$ substituents is

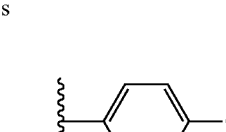

In some embodiments, Ring B with its $R^2$ and -L-$R^4$ substituents is

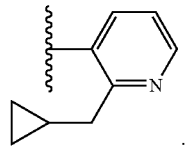 [SMILES: *c1cccnc1CC1CC1]

In some embodiments, Ring B with its $R^2$ and -L-$R^4$ substituents is

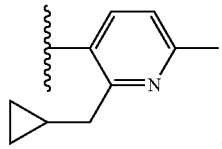

In some embodiments, Ring B with its $R^2$ and -L-$R^4$ substituents is

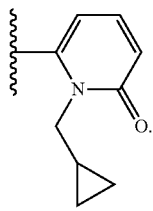 [SMILES: *c1cccc(=O)n1CC1CC1]

In some embodiments, Ring B with its $R^2$ and -L-$R^4$ substituents is

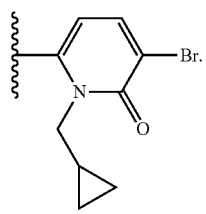 [SMILES: *c1ccc(Br)c(=O)n1CC1CC1]

In some embodiments, Ring B with its $R^2$ and -L-$R^4$ substituents is

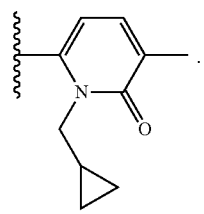 [SMILES: *c1ccc(C)c(=O)n1CC1CC1]

In some embodiments, Ring B with its $R^2$ and -L-$R^4$ substituents is

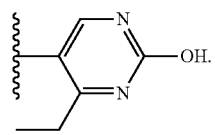

In some embodiments, Ring B with its $R^2$ and -L-$R^4$ substituents is

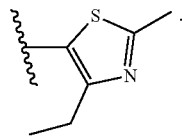 [SMILES: *c1sc(C)nc1CC]

In some embodiments, $R^1$ is methyl, $R^2$ is cyclopropylmethyl, $X^1$ is $C(R^3)$, $R^3$ is —H, and Ring A is

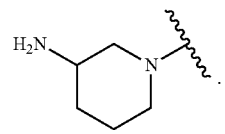 [SMILES: *N1CCCC(N)C1]

In some embodiments, $R^1$ is methyl, $R^2$ is cyclopropylmethyl, $X^1$ is $C(R^3)$, $R^3$ is —H, and Ring A is

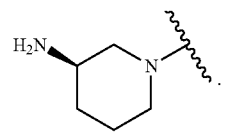 [SMILES: *N1CCC[C@@H](N)C1]

In some embodiments, $R^1$ is methyl, $R^2$ is cyclopropylmethyl, $X^1$ is $C(R^3)$, $R^3$ is —OCH$_3$, and Ring A is

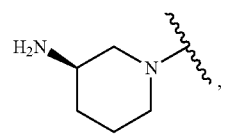

and Ring B is.

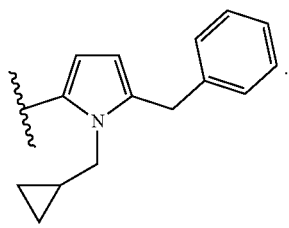 [SMILES: *c1ccc(Cc2ccccc2)n1CC1CC1]

As defined above and described herein, L is selected from a covalent bond or a $C_{1-6}$ membered straight or branched, saturated or unsaturated hydrocarbon chain wherein one methylene unit of L is optionally replaced by —C(O)N(R)—, wherein R is R or —CH$_2$phenyl. In some embodiments, L is a covalent bond. In some embodiments, L is —(CH$_2$)—. In some embodiments, L is —C(O)N(R)—. In some embodiments, R is R. In some embodiments, R is hydrogen. In some embodiments, R is $C_{1-6}$ aliphatic optionally substituted with 1-3 fluorine atoms. In some embodiments, R is —CH$_2$phenyl. In some embodiments, -L- is selected from those depicted in Table 1, below.

In some embodiments, L is a $C_{1-6}$ membered straight or branched, saturated or unsaturated hydrocarbon chain wherein one methylene unit of L is optionally replaced by —S(O)$_2$—. In some embodiments, L is —S(O)$_2$—. In some embodiments, L is —CH$_2$CH$_2$—.

In some embodiments, L is

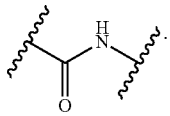

In some embodiments, L is

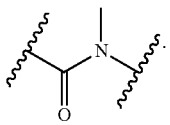 [SMILES: *C(=O)N(*)C]

In some embodiments, L is

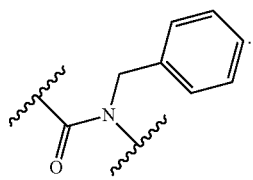 [SMILES: *C(=O)N(*)Cc1ccccc1]

In some embodiments, L is

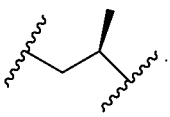 [SMILES: *C[C@H](*)C]

In some embodiments, L is

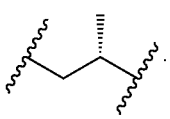 [SMILES: *C[C@@H](*)C]

In some embodiments, L is

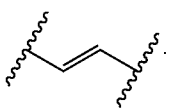 [SMILES: */C=C/*]

As defined above and described herein, $R^4$ is halogen, R, phenyl, or a 5-6-membered heteroaryl ring having 1-3 heteroatoms independently selected from nitrogen, oxygen, or sulphur, wherein $R^4$ is optionally substituted with 1-4 groups independently selected from halogen, —CN, —OR, or $C_{1-6}$ aliphatic optionally substituted with 1-3 fluorine atoms.

In some embodiments, $R^4$ is halogen. In some embodiments, $R^4$ is —Br. In some embodiments, $R^4$ is cyano. In some embodiments, $R^4$ is phenyl. In some embodiments, $R^4$ is pyridyl. In some embodiments, $R^4$ is a 5-6 membered heteroaryl ring having 1-3 heteroatoms independently selected from nitrogen, oxygen or sulphur, wherein $R^4$ is optionally substituted with 1-4 groups independently selected from halogen, —CN, —OR, or $C_{1-6}$ aliphatic optionally substituted with 1-3 fluorine atoms. In some embodiments, $R^4$ is selected from those depicted in Table 1, below.

In some embodiments, $R^4$ is substituted with —C(O)OH.

In some embodiments, $R^4$ is methyl. In some embodiments, $R^4$ is ethyl. In some embodiments, $R^4$ is hydrogen. In some embodiments, $R^4$ is cyclopropyl. In some embodiments, $R^4$ is cyclobutyl. In some embodiments, $R^4$ is n-propyl. In some embodiments, $R^4$ is iso-propyl. In some embodiments, $R^4$ is fluoro.

In some embodiments, $R^4$ is

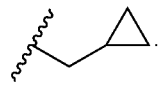

In some embodiments, $R^4$ is

In some embodiments, $R^4$ is

In some embodiments, $R^4$ is

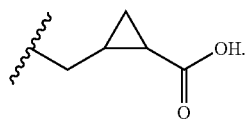 [SMILES: *CC1CC1C(=O)O]

In some embodiments, $R^4$ is

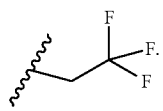

In some embodiments, $R^4$ is

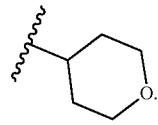

In some embodiments, R⁴ is

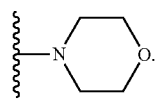

In some embodiments, R⁴ is

In some embodiments, R⁴ is

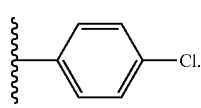

In some embodiments, R⁴ is

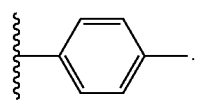

In some embodiments, R⁴ is

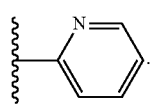

In some embodiments, R⁴ is

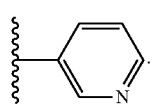

In some embodiments, R⁴ is

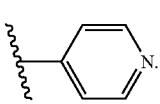

In some embodiments, R⁴ is

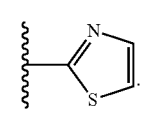

In some embodiments, R⁴ is

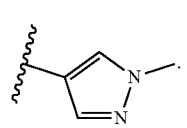 [SMILES: *c1cnn(C)c1]

As defined above and described herein, n is 1, 2, or 3. In some embodiments, n is 1. In some embodiments, n is 2. In some embodiments, n is 3. In some embodiments, n is selected from those depicted in Table 1, below.

In some embodiments, the compound of formula I or formula I' is selected from those depicted below in Table 1.

TABLE 1

Exemplary Compounds of Formula I or Formula I'

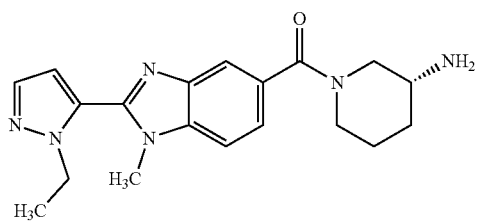 [SMILES: CCn1nccc1-c1nc2cc(C(=O)N3CCC[C@@H](N)C3)ccc2n1C]

I-1

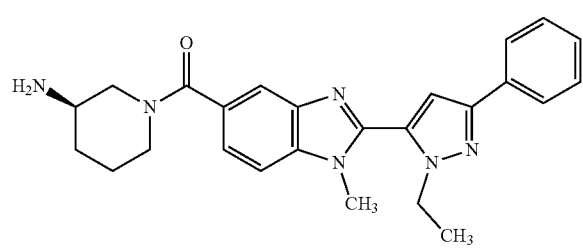 [SMILES: CCn1nc(-c2ccccc2)cc1-c1nc2cc(C(=O)N3CCC[C@@H](N)C3)ccc2n1C]

I-2

TABLE 1-continued
Exemplary Compounds of Formula I or Formula I'
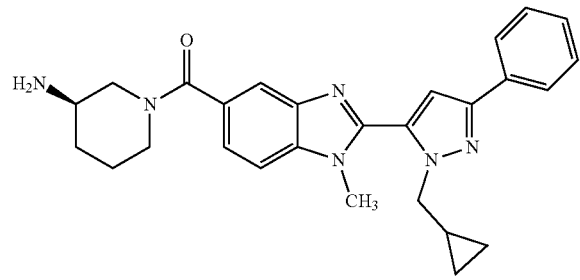 [SMILES: Cn1c(-c2cc(-c3ccccc3)nn2CC2CC2)nc2cc(C(=O)N3CCC[C@@H](N)C3)ccc21] I-3
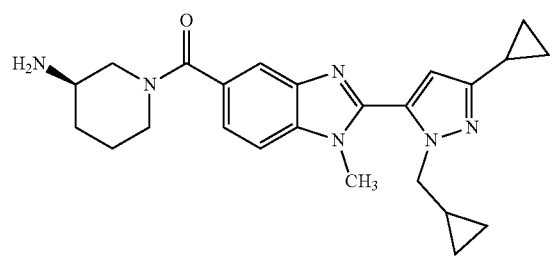 [SMILES: Cn1c(-c2cc(C3CC3)nn2CC2CC2)nc2cc(C(=O)N3CCC[C@@H](N)C3)ccc21] I-4
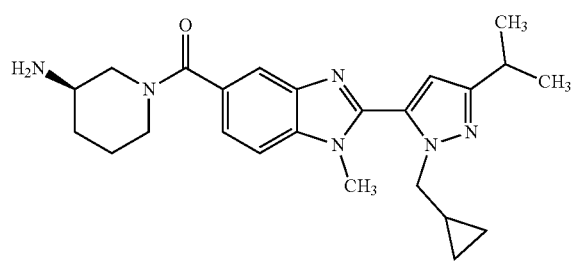 [SMILES: CC(C)c1cc(-c2nc3cc(C(=O)N4CCC[C@@H](N)C4)ccc3n2C)n(CC2CC2)n1] I-5
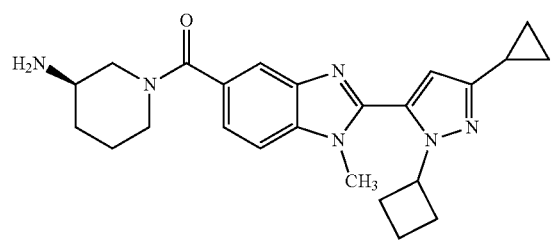 [SMILES: Cn1c(-c2cc(C3CC3)nn2C2CCC2)nc2cc(C(=O)N3CCC[C@@H](N)C3)ccc21] I-6
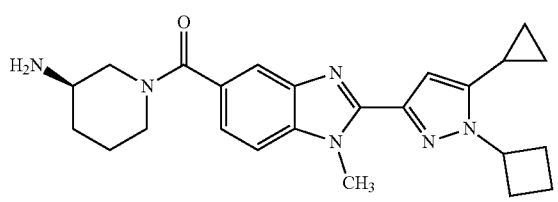 [SMILES: Cn1c(-c2cc(C3CC3)n(C3CCC3)n2)nc2cc(C(=O)N3CCC[C@@H](N)C3)ccc21] I-7
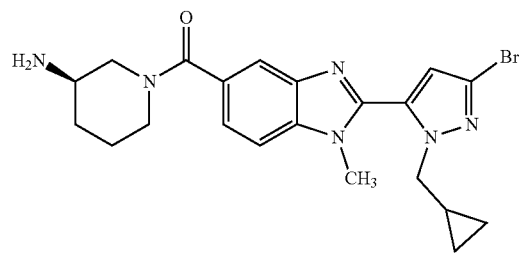 [SMILES: Cn1c(-c2cc(Br)nn2CC2CC2)nc2cc(C(=O)N3CCC[C@@H](N)C3)ccc21] I-8

TABLE 1-continued
Exemplary Compounds of Formula I or Formula I'
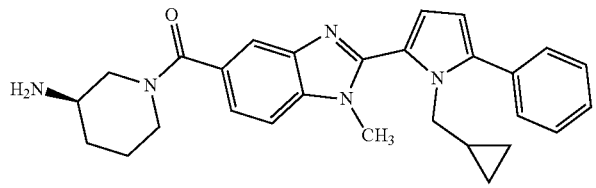 [SMILES: Cn1c(-c2ccc(-c3ccccc3)n2CC2CC2)nc2cc(C(=O)N3CCC[C@@H](N)C3)ccc21]
I-9
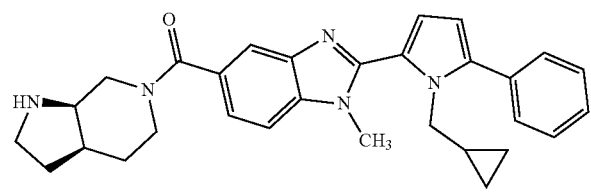 [SMILES: Cn1c(-c2ccc(-c3ccccc3)n2CC2CC2)nc2cc(C(=O)N3CC[C@H]4CCN[C@H]4C3)ccc21]
I-10
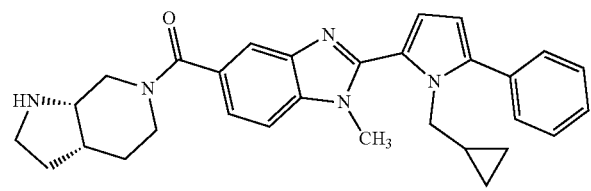 [SMILES: Cn1c(-c2ccc(-c3ccccc3)n2CC2CC2)nc2cc(C(=O)N3CC[C@@H]4CCN[C@@H]4C3)ccc21]
I-11
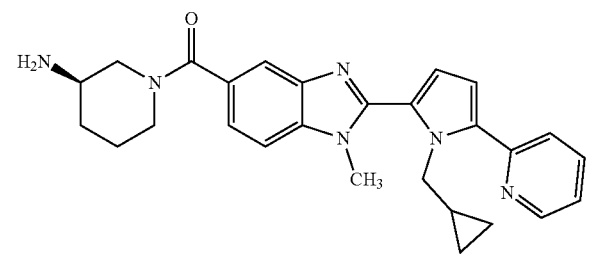 [SMILES: Cn1c(-c2ccc(-c3ccccn3)n2CC2CC2)nc2cc(C(=O)N3CCC[C@@H](N)C3)ccc21]
I-12
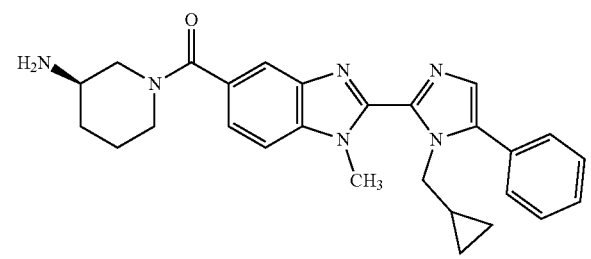 [SMILES: Cn1c(-c2ncc(-c3ccccc3)n2CC2CC2)nc2cc(C(=O)N3CCC[C@@H](N)C3)ccc21]
I-13
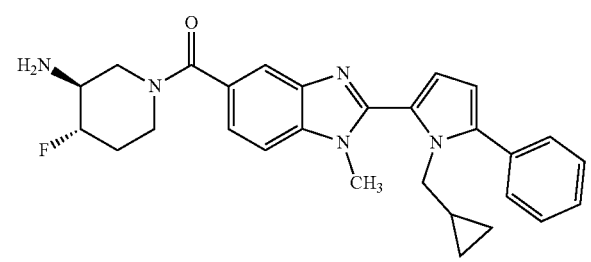 [SMILES: Cn1c(-c2ccc(-c3ccccc3)n2CC2CC2)nc2cc(C(=O)N3CC[C@H](F)[C@@H](N)C3)ccc21]
I-14

TABLE 1-continued
Exemplary Compounds of Formula I or Formula I'
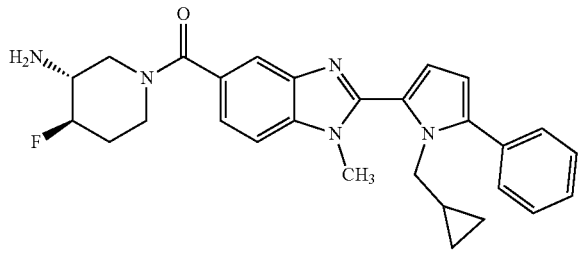 [SMILES: Cn1c(-c2ccc(-c3ccccc3)n2CC2CC2)nc2cc(C(=O)N3CC[C@@H](F)[C@H](N)C3)ccc21]
I-15
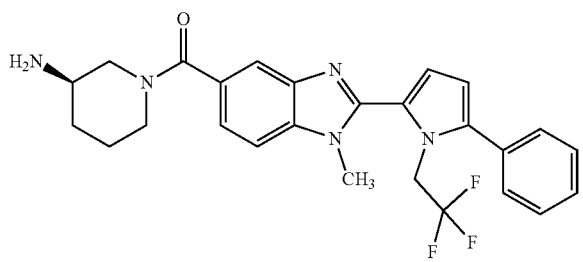 [SMILES: Cn1c(-c2ccc(-c3ccccc3)n2CC(F)(F)F)nc2cc(C(=O)N3CCC[C@@H](N)C3)ccc21]
I-16
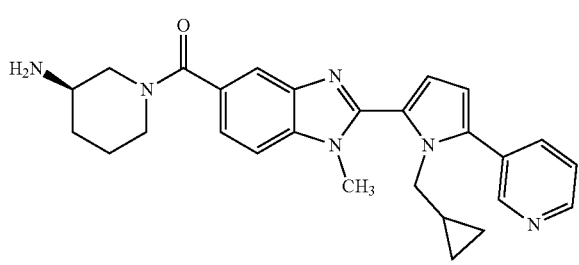 [SMILES: Cn1c(-c2ccc(-c3cccnc3)n2CC2CC2)nc2cc(C(=O)N3CCC[C@@H](N)C3)ccc21]
I-17
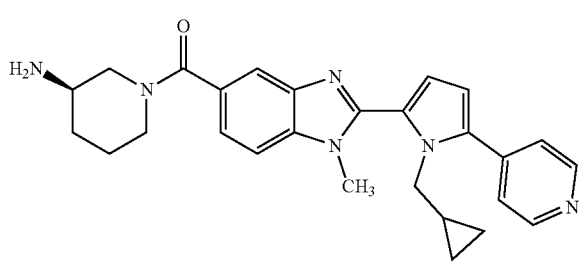 [SMILES: Cn1c(-c2ccc(-c3ccncc3)n2CC2CC2)nc2cc(C(=O)N3CCC[C@@H](N)C3)ccc21]
I-18
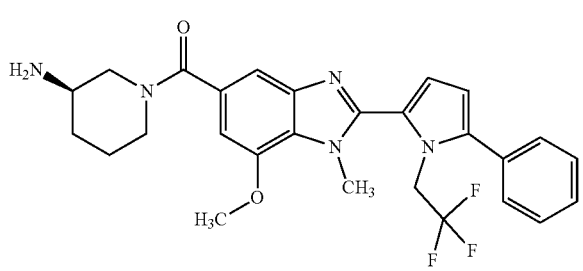 [SMILES: COc1cc(C(=O)N2CCC[C@@H](N)C2)cc2nc(-c3ccc(-c4ccccc4)n3CC(F)(F)F)n(C)c12]
I-19
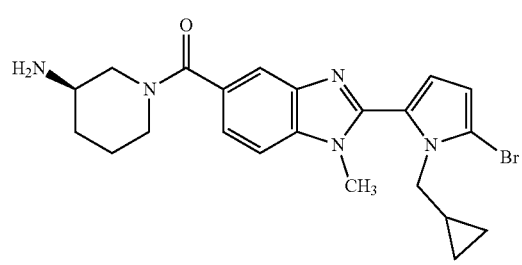 [SMILES: Cn1c(-c2ccc(Br)n2CC2CC2)nc2cc(C(=O)N3CCC[C@@H](N)C3)ccc21]
I-20

TABLE 1-continued
Exemplary Compounds of Formula I or Formula I'
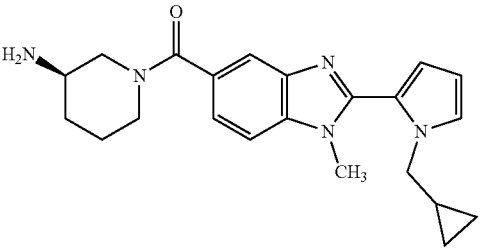 [SMILES: Cn1c(-c2cccn2CC2CC2)nc2cc(C(=O)N3CCC[C@@H](N)C3)ccc21]
I-21
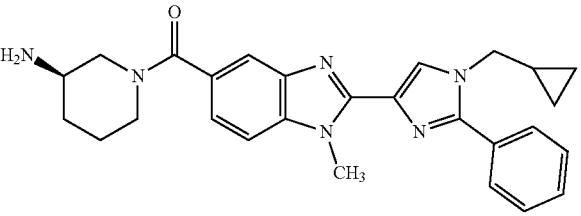 [SMILES: Cn1c(-c2cn(CC3CC3)c(-c3ccccc3)n2)nc2cc(C(=O)N3CCC[C@@H](N)C3)ccc21]
I-22
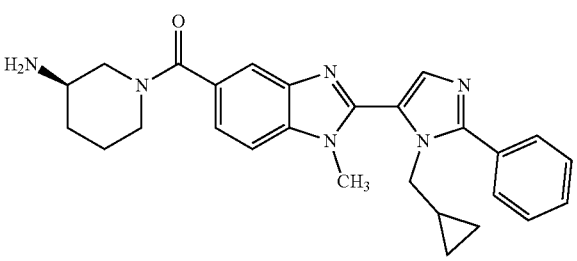 [SMILES: Cn1c(-c2cnc(-c3ccccc3)n2CC2CC2)nc2cc(C(=O)N3CCC[C@@H](N)C3)ccc21]
I-23
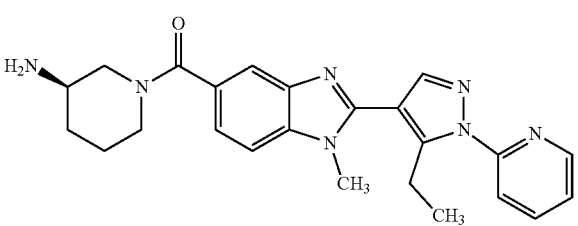 [SMILES: CCc1c(-c2nc3cc(C(=O)N4CCC[C@@H](N)C4)ccc3n2C)cnn1-c1ccccn1]
I-24
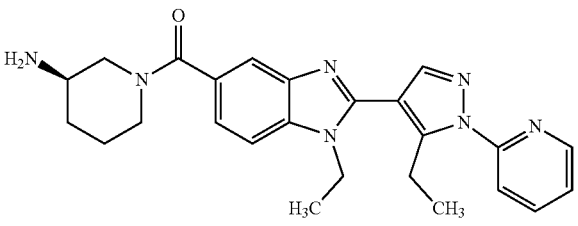 [SMILES: CCc1c(-c2nc3cc(C(=O)N4CCC[C@@H](N)C4)ccc3n2CC)cnn1-c1ccccn1]
I-25
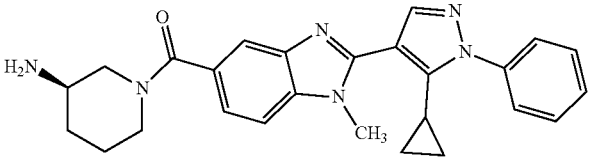 [SMILES: Cn1c(-c2cnn(-c3ccccc3)c2C2CC2)nc2cc(C(=O)N3CCC[C@@H](N)C3)ccc21]
I-26
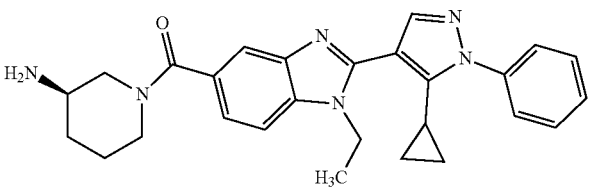 [SMILES: CCn1c(-c2cnn(-c3ccccc3)c2C2CC2)nc2cc(C(=O)N3CCC[C@@H](N)C3)ccc21]
I-27

TABLE 1-continued
Exemplary Compounds of Formula I or Formula I'
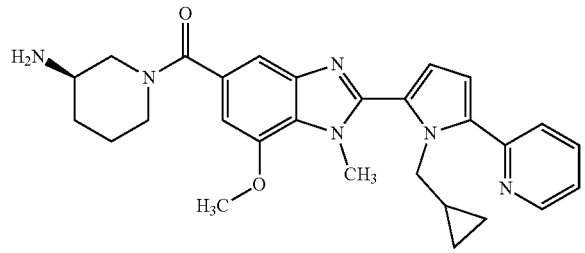 [SMILES: COc1cc(C(=O)N2CCC[C@@H](N)C2)cc2nc(-c3ccc(-c4ccccn4)n3CC3CC3)n(C)c12]
I-28
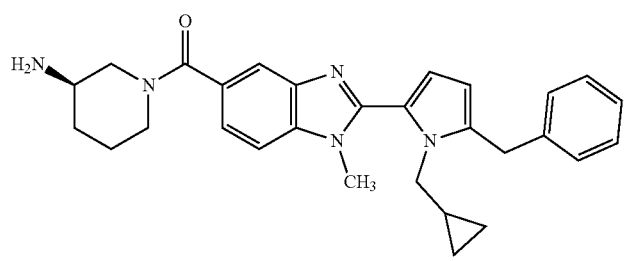
I-29
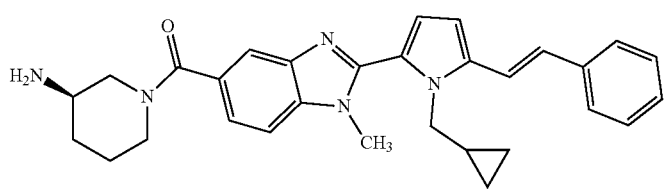 [SMILES: Cn1c(-c2ccc(/C=C/c3ccccc3)n2CC2CC2)nc2cc(C(=O)N3CCC[C@@H](N)C3)ccc21]
I-30
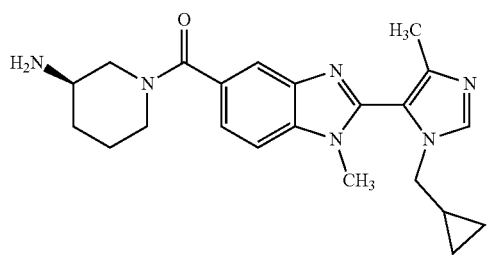 [SMILES: Cc1ncn(CC2CC2)c1-c1nc2cc(C(=O)N3CCC[C@@H](N)C3)ccc2n1C]
I-31
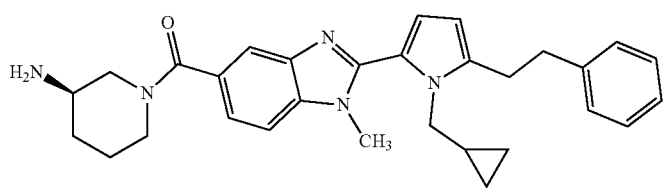 [SMILES: Cn1c(-c2ccc(CCc3ccccc3)n2CC2CC2)nc2cc(C(=O)N3CCC[C@@H](N)C3)ccc21]
I-32
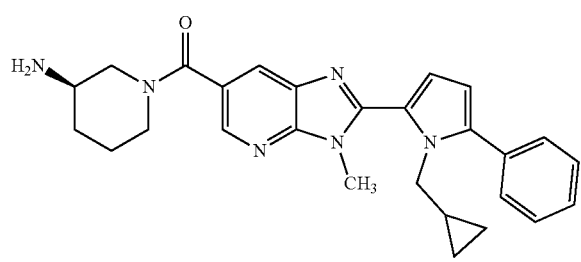 [SMILES: Cn1c(-c2ccc(-c3ccccc3)n2CC2CC2)nc2cc(C(=O)N3CCC[C@@H](N)C3)cnc21]
I-33

TABLE 1-continued
Exemplary Compounds of Formula I or Formula I'
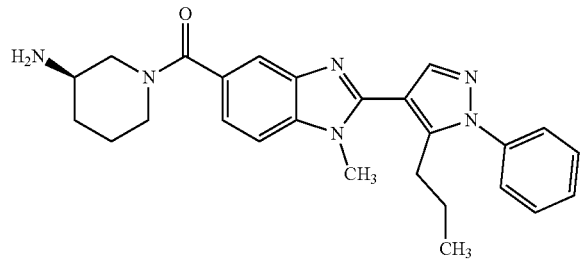 [SMILES: CCCc1c(-c2nc3cc(C(=O)N4CCC[C@@H](N)C4)ccc3n2C)cnn1-c1ccccc1]
I-34
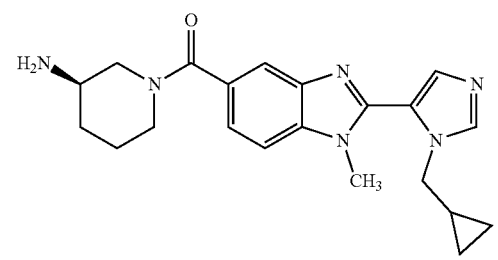 [SMILES: Cn1c(-c2cncn2CC2CC2)nc2cc(C(=O)N3CCC[C@@H](N)C3)ccc21]
I-35
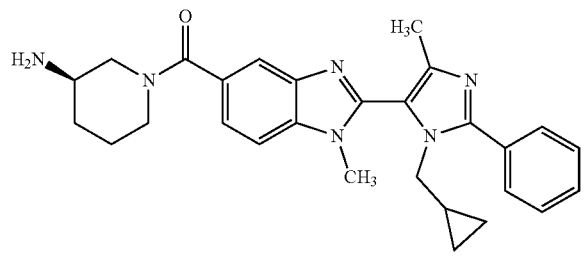 [SMILES: Cc1nc(-c2ccccc2)n(CC2CC2)c1-c1nc2cc(C(=O)N3CCC[C@@H](N)C3)ccc2n1C]
I-36
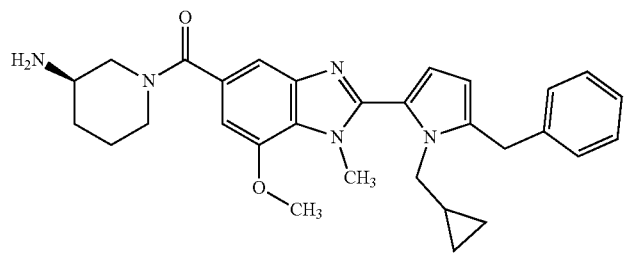 [SMILES: COc1cc(C(=O)N2CCC[C@@H](N)C2)cc2nc(-c3ccc(Cc4ccccc4)n3CC3CC3)n(C)c12]
I-37
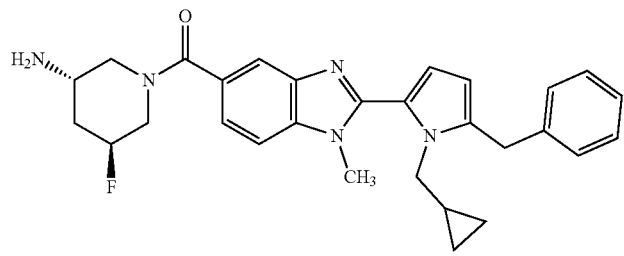 [SMILES: Cn1c(-c2ccc(Cc3ccccc3)n2CC2CC2)nc2cc(C(=O)N3C[C@@H](N)C[C@H](F)C3)ccc21]
I-38
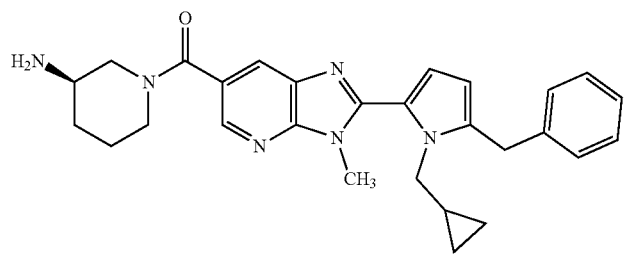 [SMILES: Cn1c(-c2ccc(Cc3ccccc3)n2CC2CC2)nc2cc(C(=O)N3CCC[C@@H](N)C3)cnc21]
I-39

TABLE 1-continued
Exemplary Compounds of Formula I or Formula I'
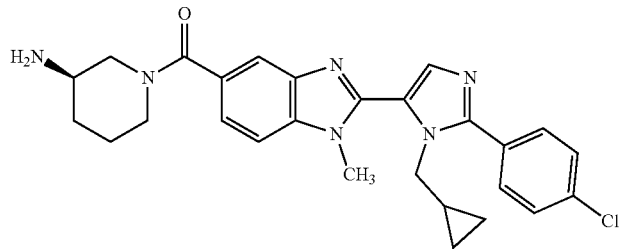 [SMILES: Cn1c(-c2cnc(-c3ccc(Cl)cc3)n2CC2CC2)nc2cc(C(=O)N3CCC[C@@H](N)C3)ccc21]
I-40
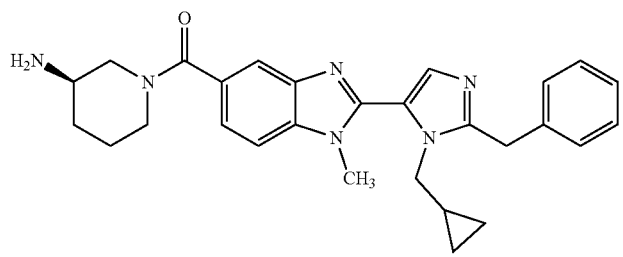 [SMILES: Cn1c(-c2cnc(Cc3ccccc3)n2CC2CC2)nc2cc(C(=O)N3CCC[C@@H](N)C3)ccc21]
I-41
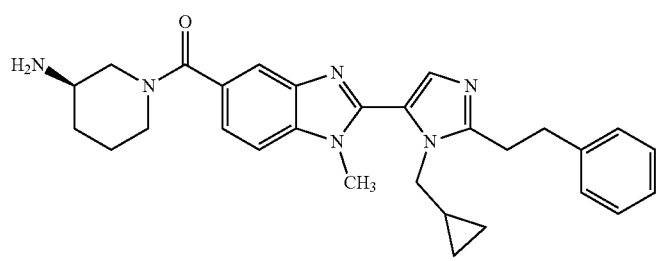 [SMILES: Cn1c(-c2cnc(CCc3ccccc3)n2CC2CC2)nc2cc(C(=O)N3CCC[C@@H](N)C3)ccc21]
I-42
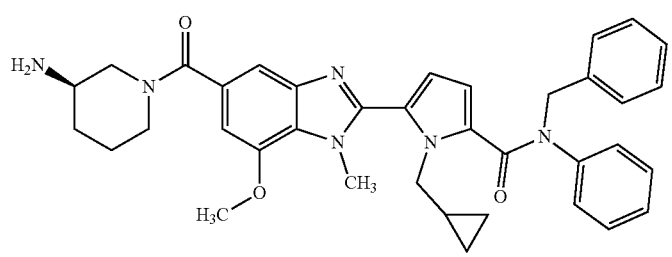 [SMILES: COc1cc(C(=O)N2CCC[C@@H](N)C2)cc2nc(-c3ccc(C(=O)N(Cc4ccccc4)c4ccccc4)n3CC3CC3)n(C)c12]
I-43
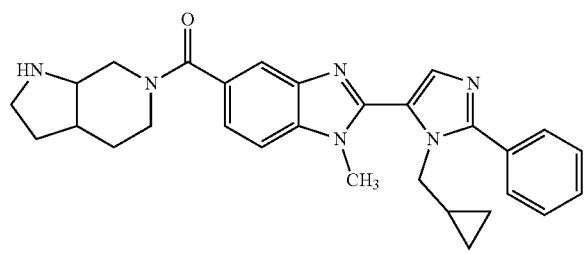 [SMILES: Cn1c(-c2cnc(-c3ccccc3)n2CC2CC2)nc2cc(C(=O)N3CCC4CCNC4C3)ccc21]
I-44
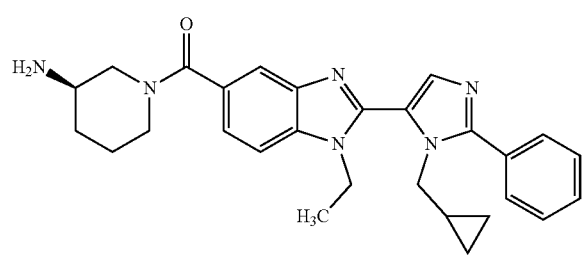 [SMILES: CCn1c(-c2cnc(-c3ccccc3)n2CC2CC2)nc2cc(C(=O)N3CCC[C@@H](N)C3)ccc21]
I-45

TABLE 1-continued
Exemplary Compounds of Formula I or Formula I'
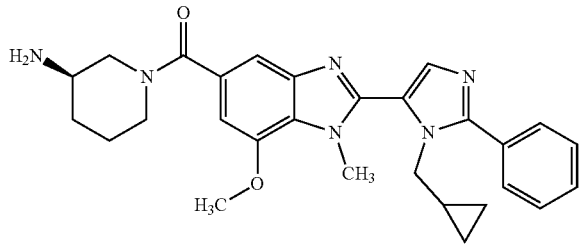 [SMILES: COc1cc(C(=O)N2CCC[C@@H](N)C2)cc2nc(-c3cnc(-c4ccccc4)n3CC3CC3)n(C)c12]
I-46
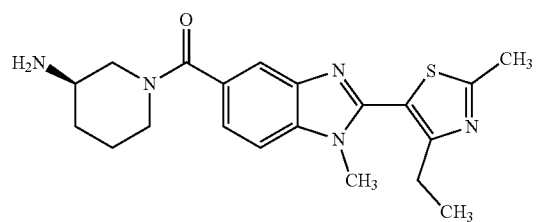 [SMILES: CCc1nc(C)sc1-c1nc2cc(C(=O)N3CCC[C@@H](N)C3)ccc2n1C]
I-47
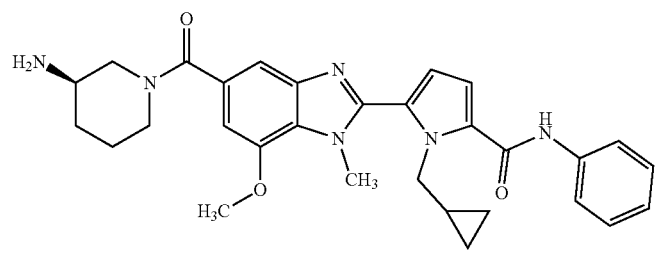 [SMILES: COc1cc(C(=O)N2CCC[C@@H](N)C2)cc2nc(-c3ccc(C(=O)Nc4ccccc4)n3CC3CC3)n(C)c12]
I-48
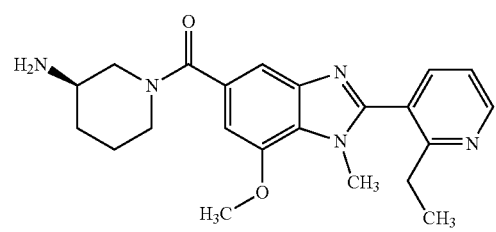 [SMILES: CCc1ncccc1-c1nc2cc(C(=O)N3CCC[C@@H](N)C3)cc(OC)c2n1C]
I-49
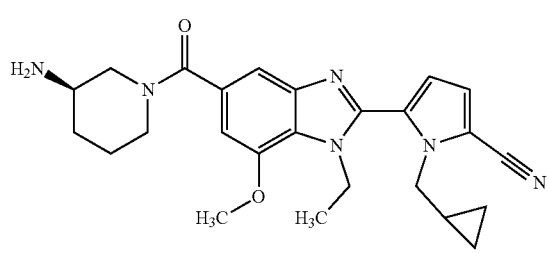 [SMILES: CCn1c(-c2ccc(C#N)n2CC2CC2)nc2cc(C(=O)N3CCC[C@@H](N)C3)cc(OC)c21]
I-50
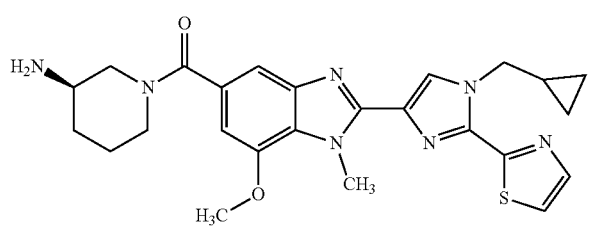 [SMILES: COc1cc(C(=O)N2CCC[C@@H](N)C2)cc2nc(-c3cn(CC4CC4)c(-c4nccs4)n3)n(C)c12]
I-51

TABLE 1-continued
Exemplary Compounds of Formula I or Formula I'
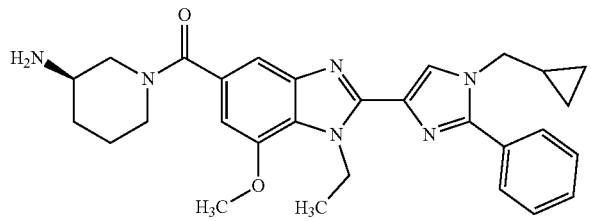 [SMILES: CCn1c(-c2cn(CC3CC3)c(-c3ccccc3)n2)nc2cc(C(=O)N3CCC[C@@H](N)C3)cc(OC)c21]
I-52
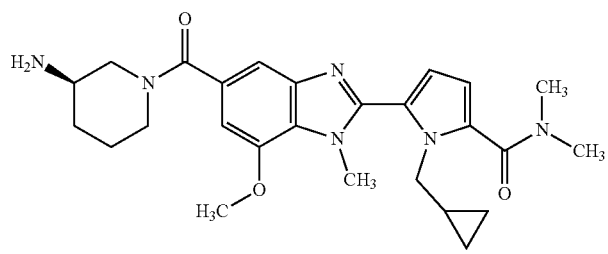 [SMILES: COc1cc(C(=O)N2CCC[C@@H](N)C2)cc2nc(-c3ccc(C(=O)N(C)C)n3CC3CC3)n(C)c12]
I-53
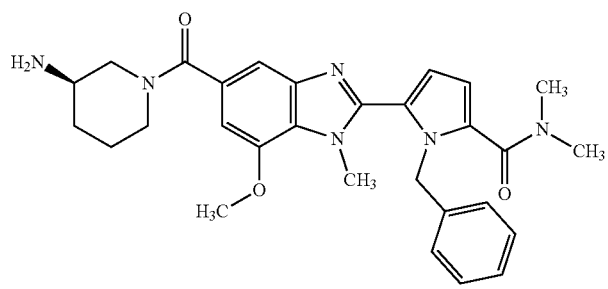 [SMILES: COc1cc(C(=O)N2CCC[C@@H](N)C2)cc2nc(-c3ccc(C(=O)N(C)C)n3Cc3ccccc3)n(C)c12]
I-54
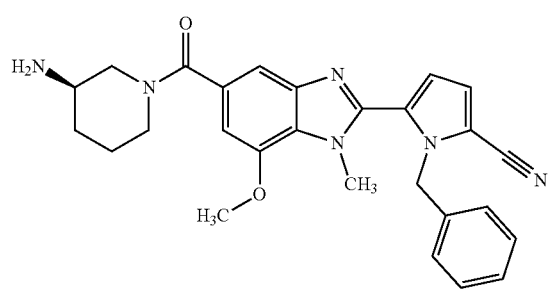 [SMILES: COc1cc(C(=O)N2CCC[C@@H](N)C2)cc2nc(-c3ccc(C#N)n3Cc3ccccc3)n(C)c12]
I-55
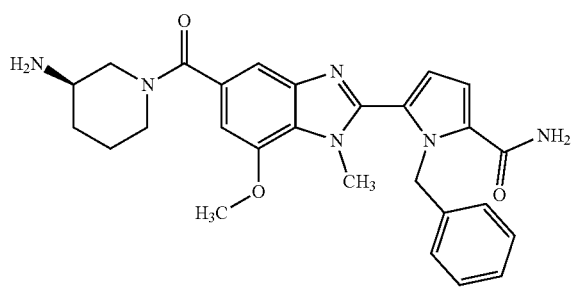 [SMILES: COc1cc(C(=O)N2CCC[C@@H](N)C2)cc2nc(-c3ccc(C(N)=O)n3Cc3ccccc3)n(C)c12]
I-56
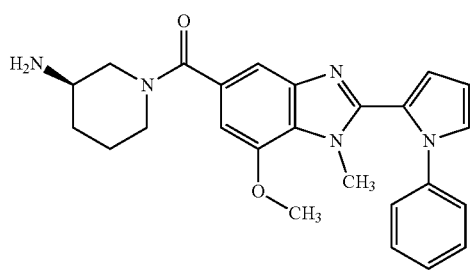 [SMILES: COc1cc(C(=O)N2CCC[C@@H](N)C2)cc2nc(-c3cccn3-c3ccccc3)n(C)c12]
I-57

TABLE 1-continued
Exemplary Compounds of Formula I or Formula I'
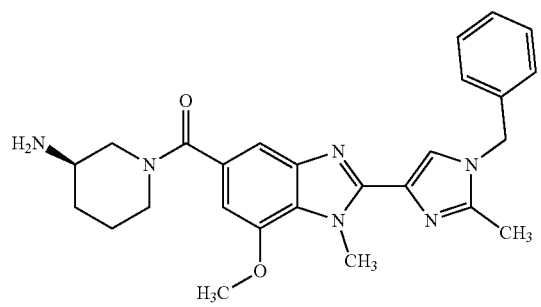 [SMILES: COc1cc(C(=O)N2CCC[C@@H](N)C2)cc2nc(-c3cn(Cc4ccccc4)c(C)n3)n(C)c12]
I-58
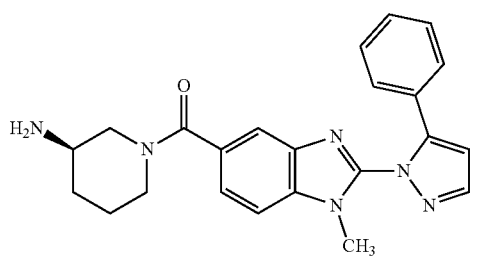 [SMILES: Cn1c(-n2nccc2-c2ccccc2)nc2cc(C(=O)N3CCC[C@@H](N)C3)ccc21]
I-59
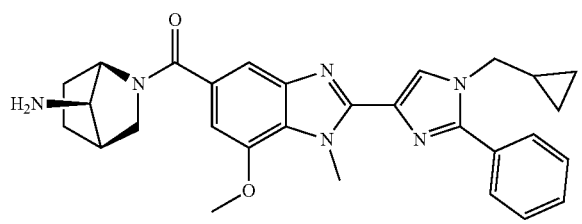 [SMILES: COc1cc(C(=O)N2C[C@H]3CC[C@@H]2[C@@H]3N)cc2nc(-c3cn(CC4CC4)c(-c4ccccc4)n3)n(C)c12]
I-60
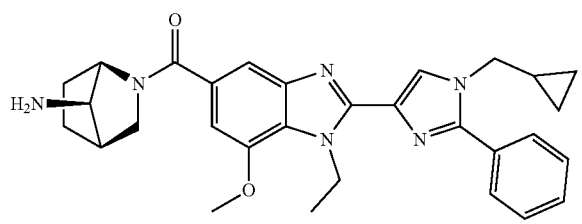 [SMILES: CCn1c(-c2cn(CC3CC3)c(-c3ccccc3)n2)nc2cc(C(=O)N3C[C@H]4CC[C@@H]3[C@@H]4N)cc(OC)c21]
I-61
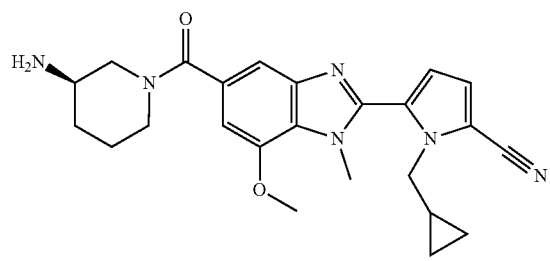 [SMILES: COc1cc(C(=O)N2CCC[C@@H](N)C2)cc2nc(-c3ccc(C#N)n3CC3CC3)n(C)c12]
I-62
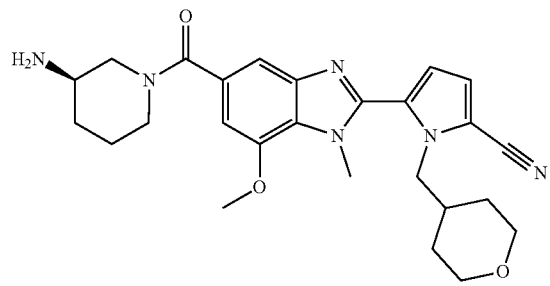 [SMILES: COc1cc(C(=O)N2CCC[C@@H](N)C2)cc2nc(-c3ccc(C#N)n3CC3CCOCC3)n(C)c12]
I-63

TABLE 1-continued
Exemplary Compounds of Formula I or Formula I'
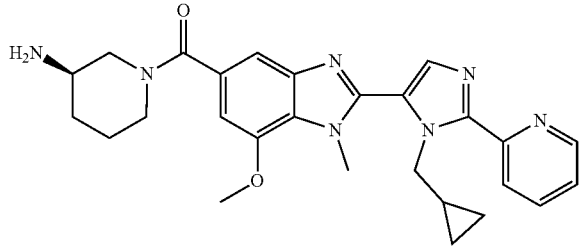 [SMILES: COc1cc(C(=O)N2CCC[C@@H](N)C2)cc2nc(-c3cnc(-c4ccccn4)n3CC3CC3)n(C)c12]
I-64
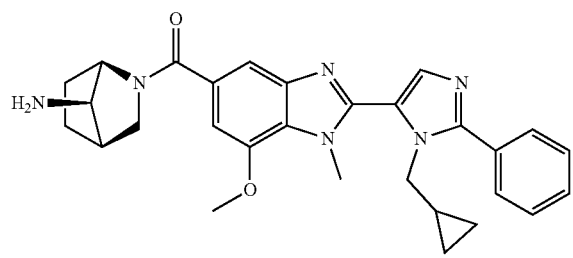 [SMILES: COc1cc(C(=O)N2C[C@H]3CC[C@@H]2[C@@H]3N)cc2nc(-c3cnc(-c4ccccc4)n3CC3CC3)n(C)c12]
I-65
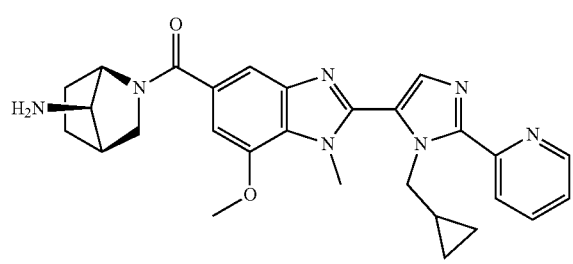 [SMILES: COc1cc(C(=O)N2C[C@H]3CC[C@@H]2[C@@H]3N)cc2nc(-c3cnc(-c4ccccn4)n3CC3CC3)n(C)c12]
I-66
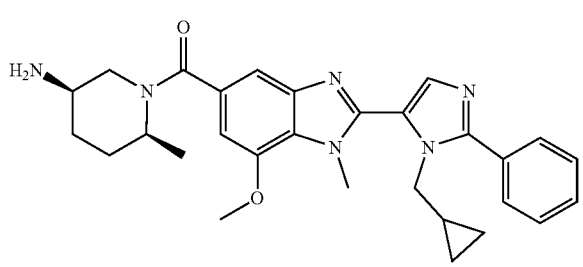 [SMILES: COc1cc(C(=O)N2C[C@H](N)CC[C@@H]2C)cc2nc(-c3cnc(-c4ccccc4)n3CC3CC3)n(C)c12]
I-67
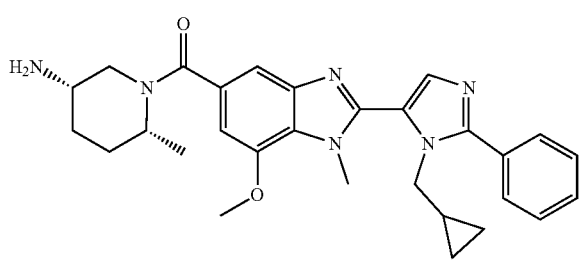 [SMILES: COc1cc(C(=O)N2C[C@@H](N)CC[C@H]2C)cc2nc(-c3cnc(-c4ccccc4)n3CC3CC3)n(C)c12]
I-68
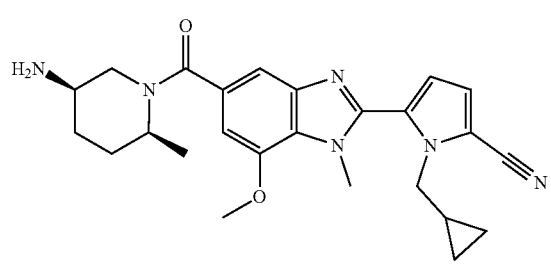 [SMILES: COc1cc(C(=O)N2C[C@H](N)CC[C@@H]2C)cc2nc(-c3ccc(C#N)n3CC3CC3)n(C)c12]
I-69

TABLE 1-continued
Exemplary Compounds of Formula I or Formula I'
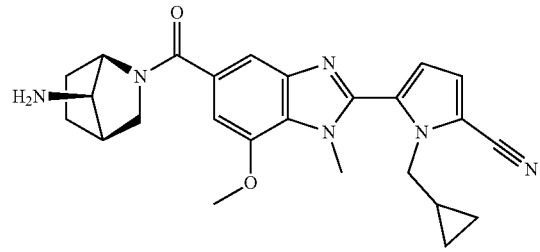 [SMILES: COc1cc(C(=O)N2C[C@H]3CC[C@@H]2[C@@H]3N)cc2nc(-c3ccc(C#N)n3CC3CC3)n(C)c12]
I-70
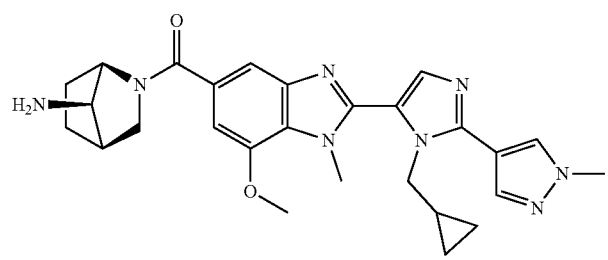 [SMILES: COc1cc(C(=O)N2C[C@H]3CC[C@@H]2[C@@H]3N)cc2nc(-c3cnc(-c4cnn(C)c4)n3CC3CC3)n(C)c12]
I-71
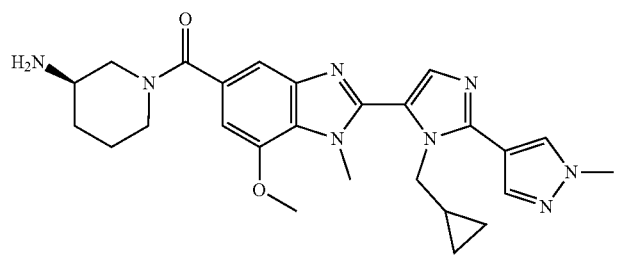 [SMILES: COc1cc(C(=O)N2CCC[C@@H](N)C2)cc2nc(-c3cnc(-c4cnn(C)c4)n3CC3CC3)n(C)c12]
I-72
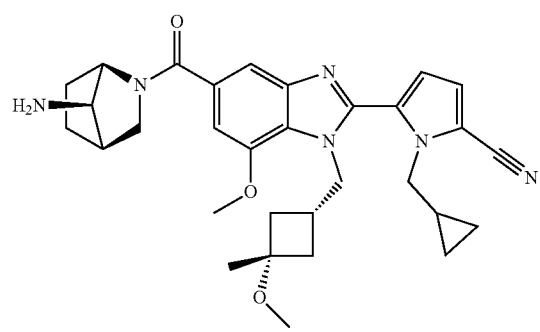 [SMILES: COc1cc(C(=O)N2C[C@H]3CC[C@@H]2[C@@H]3N)cc2nc(-c3ccc(C#N)n3CC3CC3)n(C[C@H]3C[C@@](C)(OC)C3)c12]
I-73
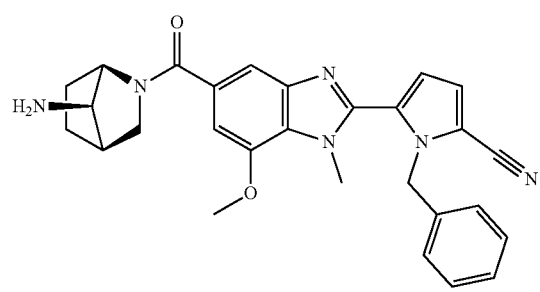 [SMILES: COc1cc(C(=O)N2C[C@H]3CC[C@@H]2[C@@H]3N)cc2nc(-c3ccc(C#N)n3Cc3ccccc3)n(C)c12]
I-74

TABLE 1-continued
Exemplary Compounds of Formula I or Formula I'
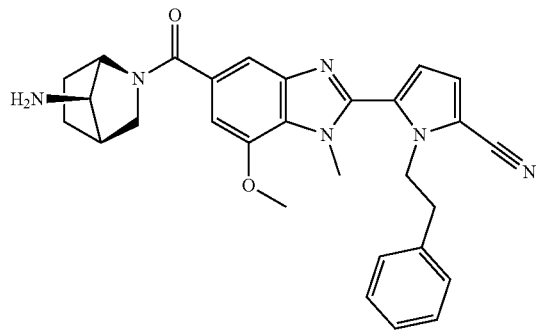
I-75
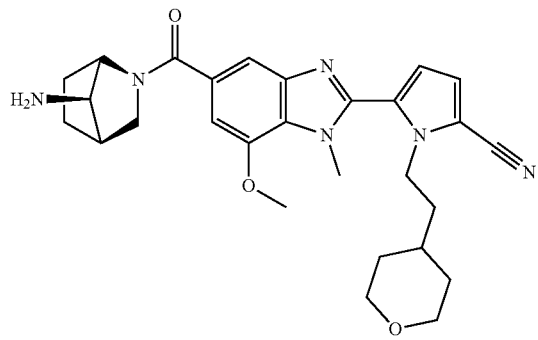
I-76
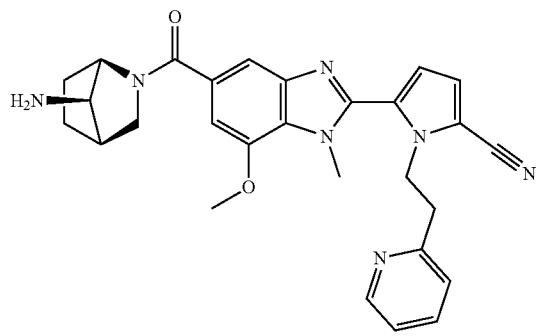 [SMILES: COc1cc(C(=O)N2C[C@H]3CC[C@@H]2[C@@H]3N)cc2nc(-c3ccc(C#N)n3CCc3ccccn3)n(C)c12]
I-77
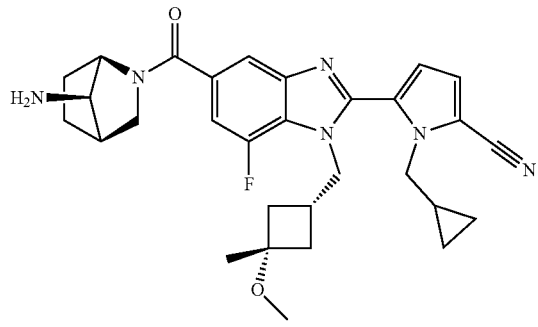 [SMILES: CO[C@]1(C)C[C@H](Cn2c(-c3ccc(C#N)n3CC3CC3)nc3cc(C(=O)N4C[C@H]5CC[C@@H]4[C@@H]5N)cc(F)c32)C1]
I-78

TABLE 1-continued
Exemplary Compounds of Formula I or Formula I'
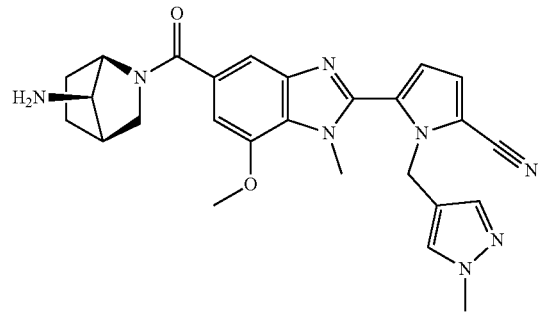 [SMILES: COc1cc(C(=O)N2C[C@H]3CC[C@@H]2[C@@H]3N)cc2nc(-c3ccc(C#N)n3Cc3cnn(C)c3)n(C)c12]
I-79
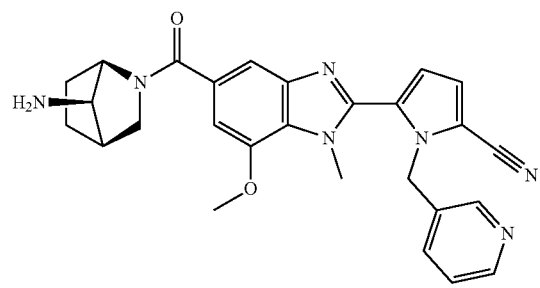 [SMILES: COc1cc(C(=O)N2C[C@H]3CC[C@@H]2[C@@H]3N)cc2nc(-c3ccc(C#N)n3Cc3cccnc3)n(C)c12]
I-80
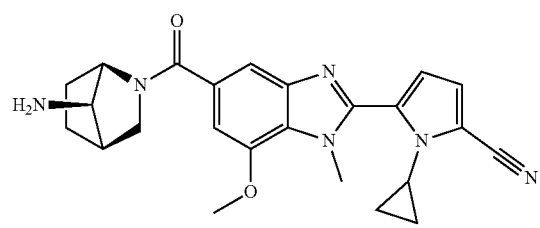 [SMILES: COc1cc(C(=O)N2C[C@H]3CC[C@@H]2[C@@H]3N)cc2nc(-c3ccc(C#N)n3C3CC3)n(C)c12]
I-81
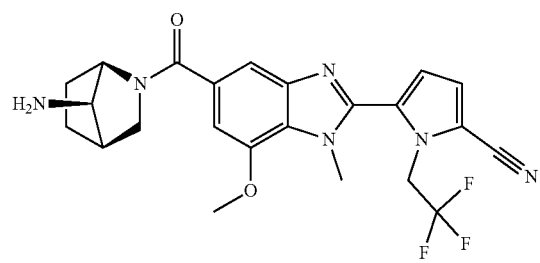 [SMILES: COc1cc(C(=O)N2C[C@H]3CC[C@@H]2[C@@H]3N)cc2nc(-c3ccc(C#N)n3CC(F)(F)F)n(C)c12]
I-82
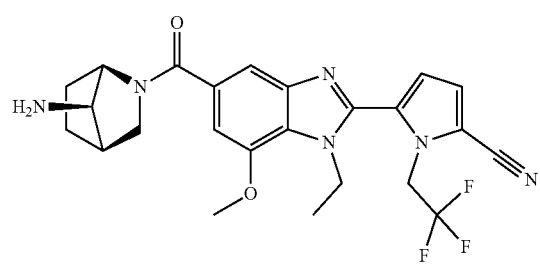 [SMILES: CCn1c(-c2ccc(C#N)n2CC(F)(F)F)nc2cc(C(=O)N3C[C@H]4CC[C@@H]3[C@@H]4N)cc(OC)c21]
I-83

TABLE 1-continued
Exemplary Compounds of Formula I or Formula I'
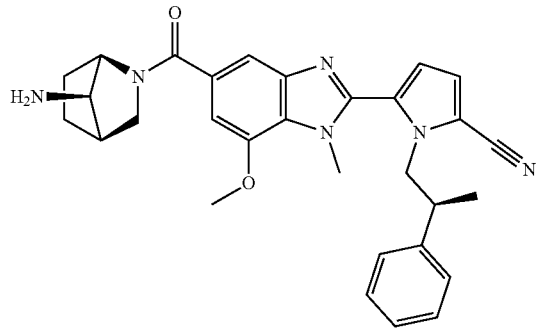 [SMILES: COc1cc(C(=O)N2C[C@H]3CC[C@@H]2[C@@H]3N)cc2nc(-c3ccc(C#N)n3C[C@@H](C)c3ccccc3)n(C)c12]
I-84
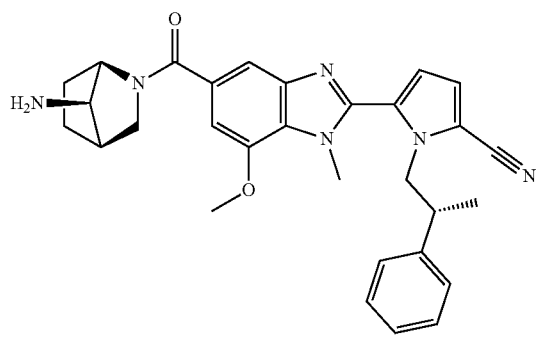 [SMILES: COc1cc(C(=O)N2C[C@H]3CC[C@@H]2[C@@H]3N)cc2nc(-c3ccc(C#N)n3C[C@H](C)c3ccccc3)n(C)c12]
I-85
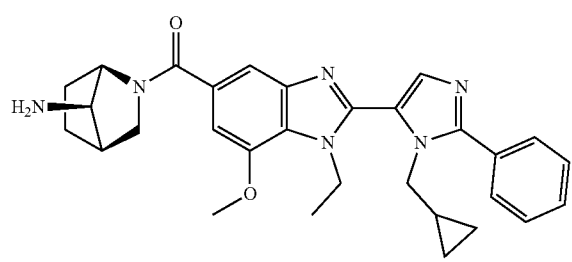 [SMILES: CCn1c(-c2cnc(-c3ccccc3)n2CC2CC2)nc2cc(C(=O)N3C[C@H]4CC[C@@H]3[C@@H]4N)cc(OC)c21]
I-86
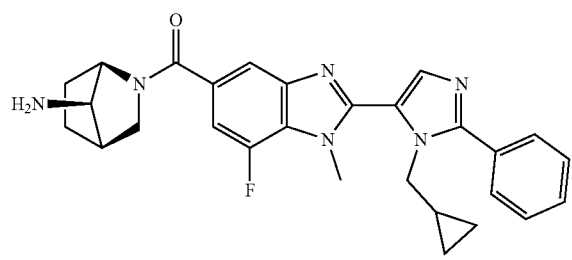 [SMILES: Cn1c(-c2cnc(-c3ccccc3)n2CC2CC2)nc2cc(C(=O)N3C[C@H]4CC[C@@H]3[C@@H]4N)cc(F)c21]
I-87
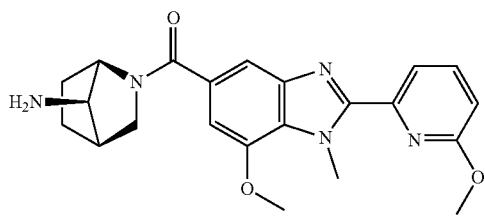 [SMILES: COc1cccc(-c2nc3cc(C(=O)N4C[C@H]5CC[C@@H]4[C@@H]5N)cc(OC)c3n2C)n1]
I-88

TABLE 1-continued
Exemplary Compounds of Formula I or Formula I'
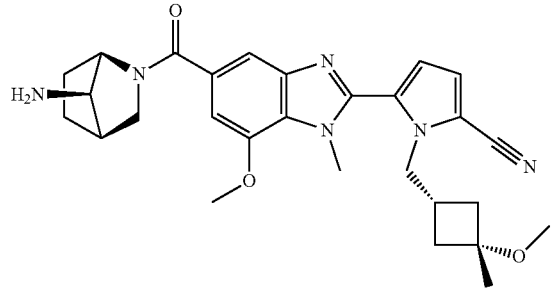 [SMILES: COc1cc(C(=O)N2C[C@H]3CC[C@@H]2[C@@H]3N)cc2nc(-c3ccc(C#N)n3C[C@H]3C[C@@](C)(OC)C3)n(C)c12]
I-89
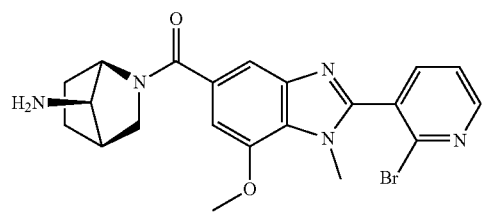 [SMILES: COc1cc(C(=O)N2C[C@H]3CC[C@@H]2[C@@H]3N)cc2nc(-c3cccnc3Br)n(C)c12]
I-90
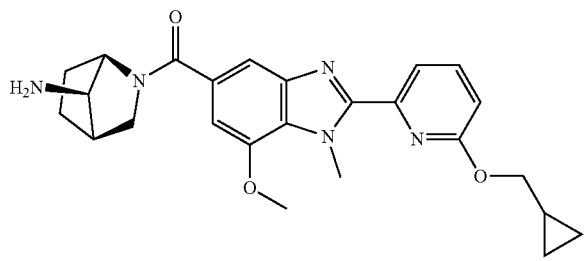 [SMILES: COc1cc(C(=O)N2C[C@H]3CC[C@@H]2[C@@H]3N)cc2nc(-c3cccc(OCC4CC4)n3)n(C)c12]
I-91
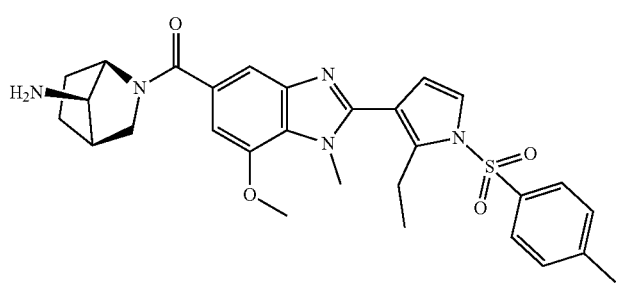 [SMILES: CCc1c(-c2nc3cc(C(=O)N4C[C@H]5CC[C@@H]4[C@@H]5N)cc(OC)c3n2C)ccn1S(=O)(=O)c1ccc(C)cc1]
I-92
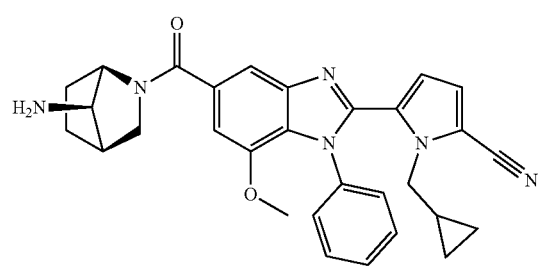 [SMILES: COc1cc(C(=O)N2C[C@H]3CC[C@@H]2[C@@H]3N)cc2nc(-c3ccc(C#N)n3CC3CC3)n(-c3ccccc3)c12]
I-93

TABLE 1-continued
Exemplary Compounds of Formula I or Formula I'
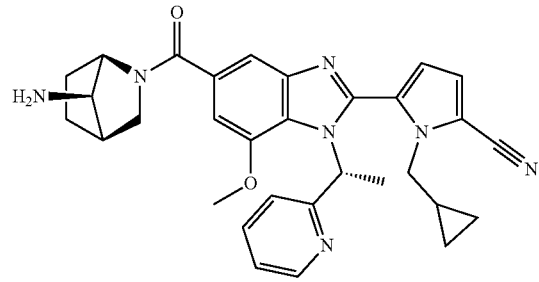 [SMILES: COc1cc(C(=O)N2C[C@H]3CC[C@@H]2[C@@H]3N)cc2nc(-c3ccc(C#N)n3CC3CC3)n([C@H](C)c3ccccn3)c12]
I-94
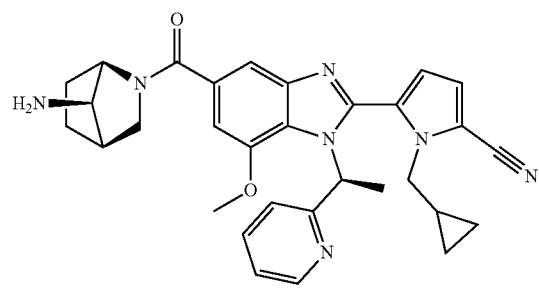 [SMILES: COc1cc(C(=O)N2C[C@H]3CC[C@@H]2[C@@H]3N)cc2nc(-c3ccc(C#N)n3CC3CC3)n([C@@H](C)c3ccccn3)c12]
I-95
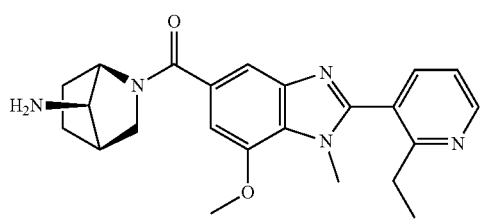 [SMILES: CCc1ncccc1-c1nc2cc(C(=O)N3C[C@H]4CC[C@@H]3[C@@H]4N)cc(OC)c2n1C]
I-96
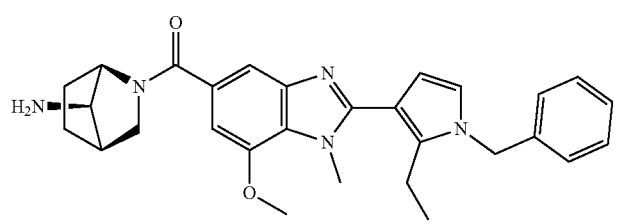 [SMILES: CCc1c(-c2nc3cc(C(=O)N4C[C@H]5CC[C@@H]4[C@@H]5N)cc(OC)c3n2C)ccn1Cc1ccccc1]
I-97
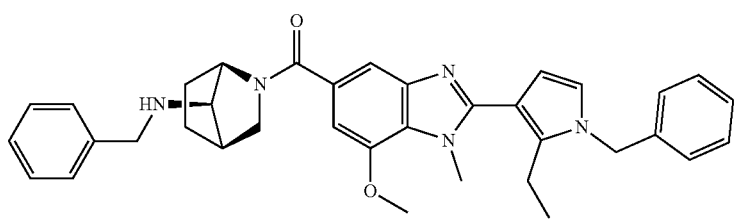 [SMILES: CCc1c(-c2nc3cc(C(=O)N4C[C@H]5CC[C@@H]4[C@@H]5NCc4ccccc4)cc(OC)c3n2C)ccn1Cc1ccccc1]
I-98
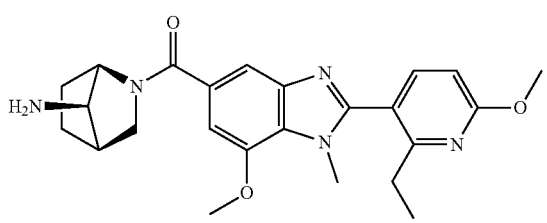 [SMILES: CCc1nc(OC)ccc1-c1nc2cc(C(=O)N3C[C@H]4CC[C@@H]3[C@@H]4N)cc(OC)c2n1C]
I-99

TABLE 1-continued
Exemplary Compounds of Formula I or Formula I'
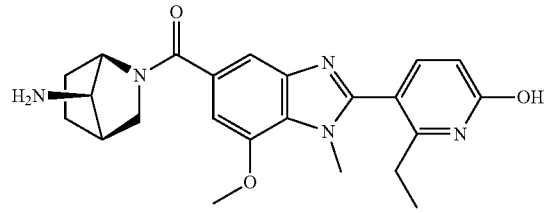 [SMILES: CCc1nc(O)ccc1-c1nc2cc(C(=O)N3C[C@H]4CC[C@@H]3[C@@H]4N)cc(OC)c2n1C]
I-100
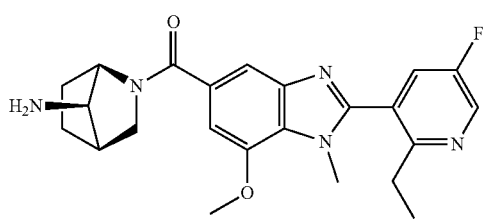 [SMILES: CCc1ncc(F)cc1-c1nc2cc(C(=O)N3C[C@H]4CC[C@@H]3[C@@H]4N)cc(OC)c2n1C]
I-101
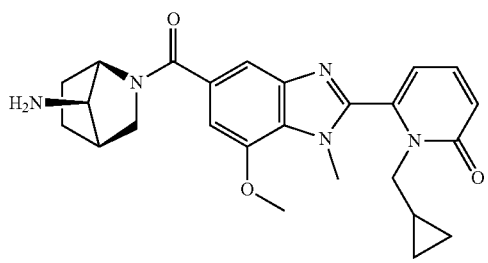 [SMILES: COc1cc(C(=O)N2C[C@H]3CC[C@@H]2[C@@H]3N)cc2nc(-c3cccc(=O)n3CC3CC3)n(C)c12]
I-102
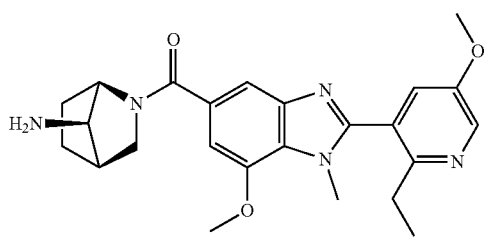 [SMILES: CCc1ncc(OC)cc1-c1nc2cc(C(=O)N3C[C@H]4CC[C@@H]3[C@@H]4N)cc(OC)c2n1C]
I-103
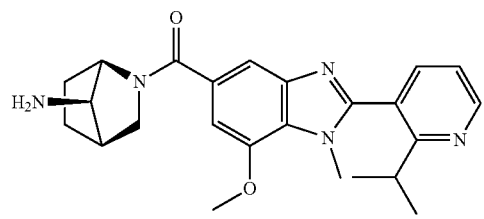 [SMILES: COc1cc(C(=O)N2C[C@H]3CC[C@@H]2[C@@H]3N)cc2nc(-c3cccnc3C(C)C)n(C)c12]
I-104
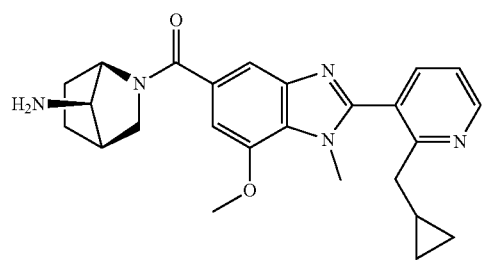 [SMILES: COc1cc(C(=O)N2C[C@H]3CC[C@@H]2[C@@H]3N)cc2nc(-c3cccnc3CC3CC3)n(C)c12]
I-105

TABLE 1-continued
Exemplary Compounds of Formula I or Formula I'
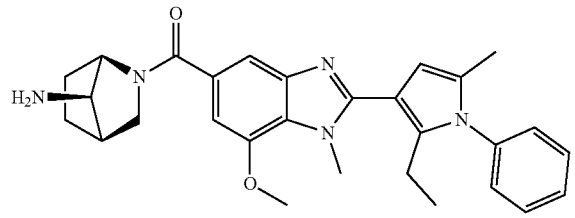 [SMILES: CCc1c(-c2nc3cc(C(=O)N4C[C@H]5CC[C@@H]4[C@@H]5N)cc(OC)c3n2C)cc(C)n1-c1ccccc1]
I-106
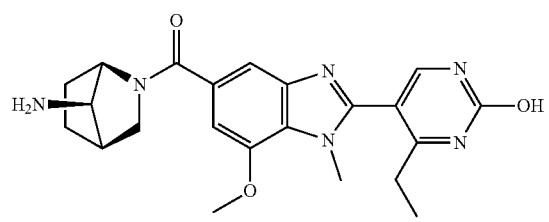 [SMILES: CCc1nc(O)ncc1-c1nc2cc(C(=O)N3C[C@H]4CC[C@@H]3[C@@H]4N)cc(OC)c2n1C]
I-107
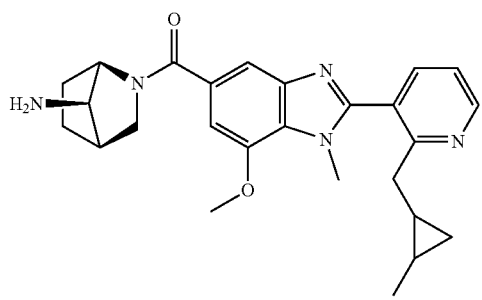 [SMILES: COc1cc(C(=O)N2C[C@H]3CC[C@@H]2[C@@H]3N)cc2nc(-c3cccnc3CC3CC3C)n(C)c12]
I-108
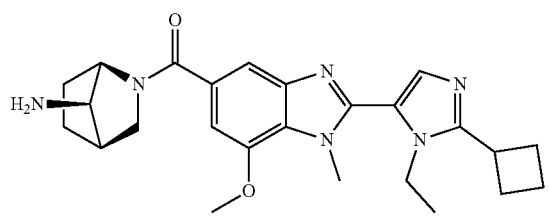 [SMILES: CCn1c(-c2nc3cc(C(=O)N4C[C@H]5CC[C@@H]4[C@@H]5N)cc(OC)c3n2C)cnc1C1CCC1]
I-109
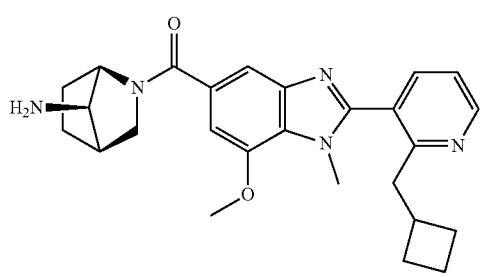 [SMILES: COc1cc(C(=O)N2C[C@H]3CC[C@@H]2[C@@H]3N)cc2nc(-c3cccnc3CC3CCC3)n(C)c12]
I-110
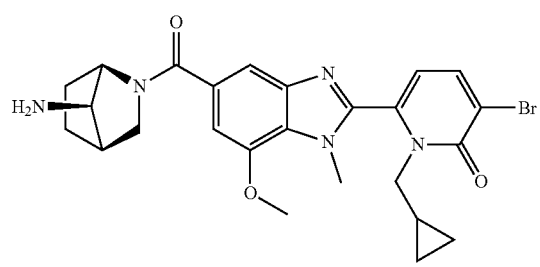 [SMILES: COc1cc(C(=O)N2C[C@H]3CC[C@@H]2[C@@H]3N)cc2nc(-c3ccc(Br)c(=O)n3CC3CC3)n(C)c12]
I-111

TABLE 1-continued
Exemplary Compounds of Formula I or Formula I'
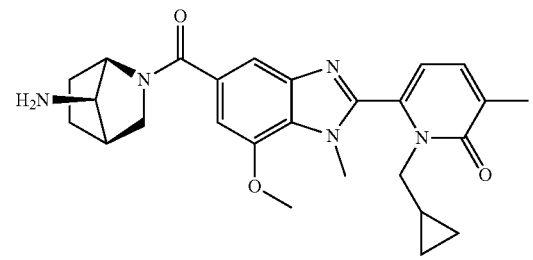 [SMILES: COc1cc(C(=O)N2C[C@H]3CC[C@@H]2[C@@H]3N)cc2nc(-c3ccc(C)c(=O)n3CC3CC3)n(C)c12]
I-112
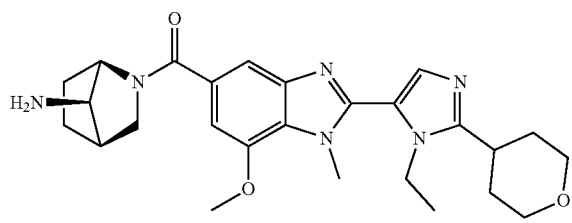 [SMILES: CCn1c(-c2nc3cc(C(=O)N4C[C@H]5CC[C@@H]4[C@@H]5N)cc(OC)c3n2C)cnc1C1CCOCC1]
I-113
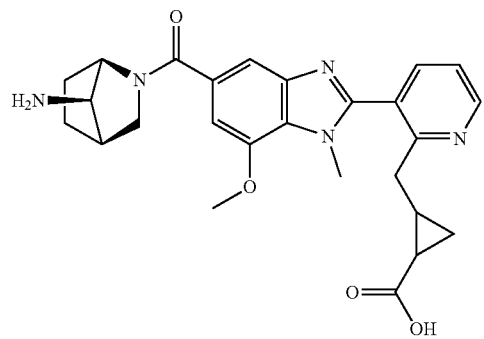 [SMILES: COc1cc(C(=O)N2C[C@H]3CC[C@@H]2[C@@H]3N)cc2nc(-c3cccnc3CC3CC3C(=O)O)n(C)c12]
I-114
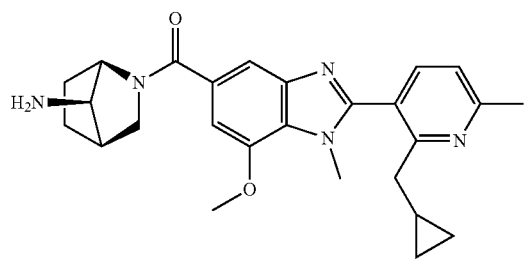 [SMILES: COc1cc(C(=O)N2C[C@H]3CC[C@@H]2[C@@H]3N)cc2nc(-c3ccc(C)nc3CC3CC3)n(C)c12]
I-115
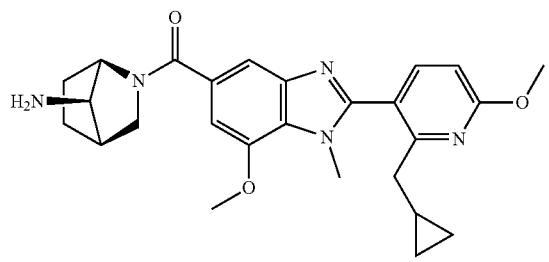 [SMILES: COc1ccc(-c2nc3cc(C(=O)N4C[C@H]5CC[C@@H]4[C@@H]5N)cc(OC)c3n2C)c(CC2CC2)n1]
I-116
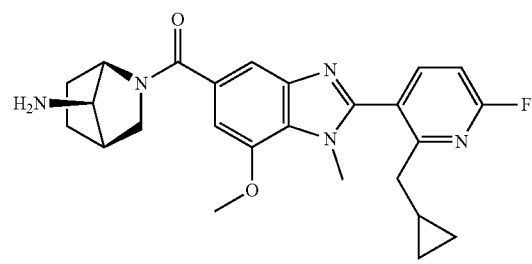 [SMILES: COc1cc(C(=O)N2C[C@H]3CC[C@@H]2[C@@H]3N)cc2nc(-c3ccc(F)nc3CC3CC3)n(C)c12]
I-117

TABLE 1-continued

Exemplary Compounds of Formula I or Formula I'

I-118

I-119

I-120

I-121

I-122

In certain embodiments, the present invention provides any compound described above and herein, or a pharmaceutically acceptable salt thereof. In some embodiments, the present invention provides a compound as depicted in Table 1, above, or a pharmaceutically acceptable salt thereof.

In some embodiments, the present invention provides any compound described above and herein in isolated form.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosis. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosis, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosis, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, behcet's disease, Behcet's syndrome, Bells Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cyrptococcosis, cystic fibrosis, deficiency of the interleukin-1-receptor antagonist (DTRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungiodes, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osterarthritis, otitis media, paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis *nodosa*, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, and Wegener's granulomatosis.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosis. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosis. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosis comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparative HPLC methods

Basic HPLC preparative method

Column: XBridge™ Prep. C18 10 um OBD™, 30×100 mm

Mobile Phase: 5-95% Acetonitrile (0.2% ammonium hydroxide) in Water (0.2% ammonium hydroxide) over 14 minutes Flow Rate: 40 mL/min UV Detection: 215 and 254 nm Acidic HPLC preparative method Column: Sunfire™ Prep. C18 10 um OBD™, 30×100 mm Mobile Phase: 5-95% Acetonitrile (0.1% formic acid) in Water (0.1% formic acid) over 14 minutes Flow Rate: 40 mL/min UV Detection: 215 and 254 nm Analytical LCMS methods:

Method A

MET/u-HPLC (low pH MSQ1 7 min method)

Column: Phenomenex Kinetex-XB C18, 2.1 mm×100 mm, 1.7 µm

Flow rate: 0.6 ml/min

Mobile Phase: A, Formic acid (aqueous) 0.1% and B, Formic acid (MeCN) 0.1%

Injection Vol: 3 µl

Temp.: 40° C.

Detection: 215 nm (nominal)

Gradient Time (minutes)—% B 0.00-5

5.30-100

5.80-100

5.82-5

Method B

MET/CR/1600 (high pH MS10 7 min method)

Column: Phenomenex Gemini C18, 2.0 mm×100 mm, 3 m

Flow rate: 0.5 ml/min

Mobile phase: A, 2 mM ammonium bicarbonate in HPLC grade water pH10

B HPLC grade MeCN

Injection volume: 3

Temperature: 50° C.

Detection: 215 nm

Gradient time: (minutes)—% B 0.0-5

5.50-100

5.90-100

5.92-5

9.00-5

Method C

METCR 1416 (low pH Shimadzu 7 min method)

Column: Waters Atlantis dC18, 2.1 mm×100 mm, 3 µm column

Flow rate: 0.6 ml/min

Mobile Phase: A, Formic acid (aqueous) 0.1% and B, Formic acid (acetonitrile) 0.1%

Injection Vol: 3

Temp.: 40° C.

Detection: 215 nm (nominal)

Gradient Time (minutes)—% B 0.00-5

5.00-100

5.40-100

5.42-5

Method D
METCR 1410 (low pH Shimadzu 2 min method)
Column: Kinetex Core-Shell C18, 2.1 mm×50 mm, 5 μm column
Flow rate: 1.2 ml/min
Mobile Phase: A, Formic acid (aqueous) 0.1% and B, Formic acid (acetonitrile) 0.1%
Injection Vol: 3 μl
Temp.: 40° C.
Detection: 215 nm (nominal)
Gradient Time (minutes)—% B
0.00-5
1.20-100
1.30-100
1.31-5
Method H
MET/u-HPLC (high pH MS16 7 min method)
Column: Waters UPLC CSH C18, 2.1 mm×100 mm 5 μm column
Flow rate: 0.6 ml/min
Mobile Phase: A, 2 mM Ammonium bicarbonate modified to pH 10 with Ammonium hydroxide (aqueous) and B, acetonitrile
Injection Vol: 3 μl
Temp.: 40° C.
Detection: 215 nm (nominal)
Gradient Time (minutes)—% B
0.00-5
5.30-100
5.80-100
5.82-5

Method J
MET/CR/0990 (high pH 3 min method)
Column: Phenomenex Gemini C18, 2.0 mm×100 mm, 3 m
Flow rate: 1 ml/min
Mobile phase: A, 2 mM ammonium bicarbonate in HPLC grade water pH10
B HPLC grade MeCN
Injection volume: 3
Temperature: 60° C.
Detection: 215 nm
Gradient time: (minutes)—% B
0.0-1
1.80-100
2.10-100
2.30-1
Analytical and preparative chiral HPLC methods:
Method E:
Chiral HPLC preparative method
Column: Chiralpak IC 250 mm×4.6 mm, 5 μm column
Flow rate: 15 ml/min
Mobile Phase: 35% Ethanol: 65% CO2
Sample Diluent: Ethanol
Temp.: 40° C.
Detection: 215 nm (nominal)
Method F:
Chiral purity analysis method
Column: Chiralpak IC 250 mm×4.6 mm, 5 μm column
Flow Rate: 4 ml/min
Injection Vol: 10 μL
Temp.: 40° C.
Detection: 215 nm
Isocratic Conditions 40% Ethanol: 60% CO2

Certain compounds of the present invention were prepared according to Schemes 1 and 2, below.

Scheme 1

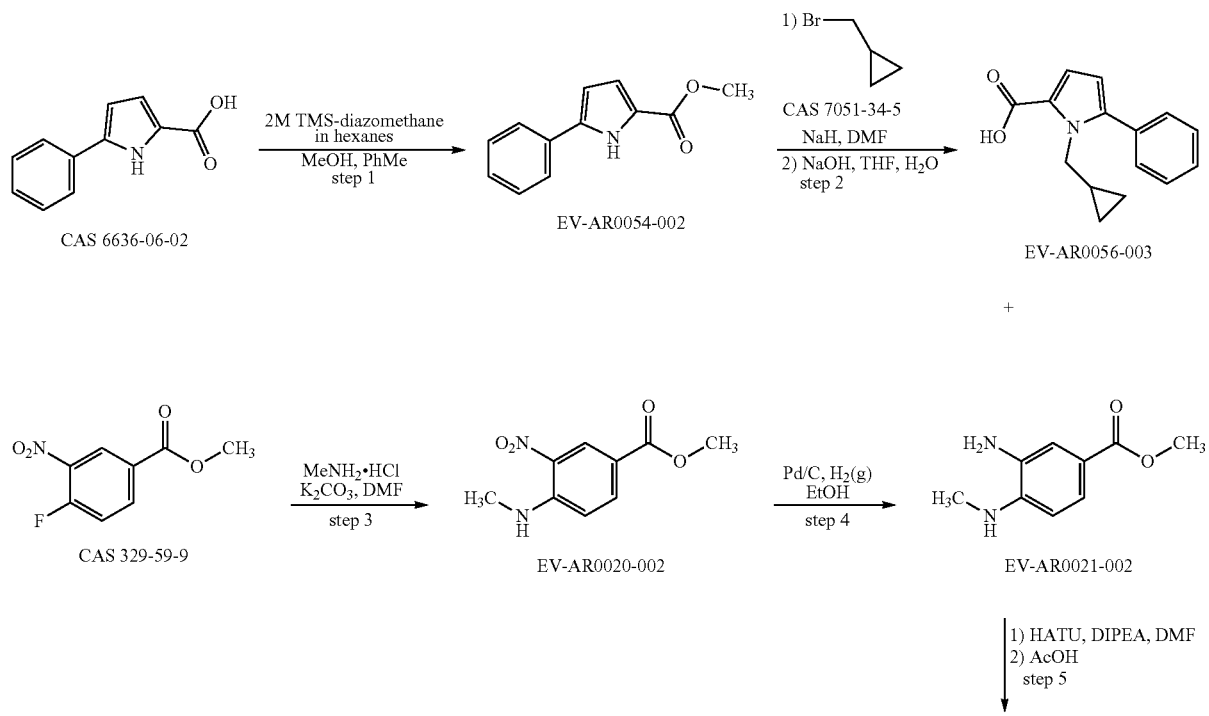

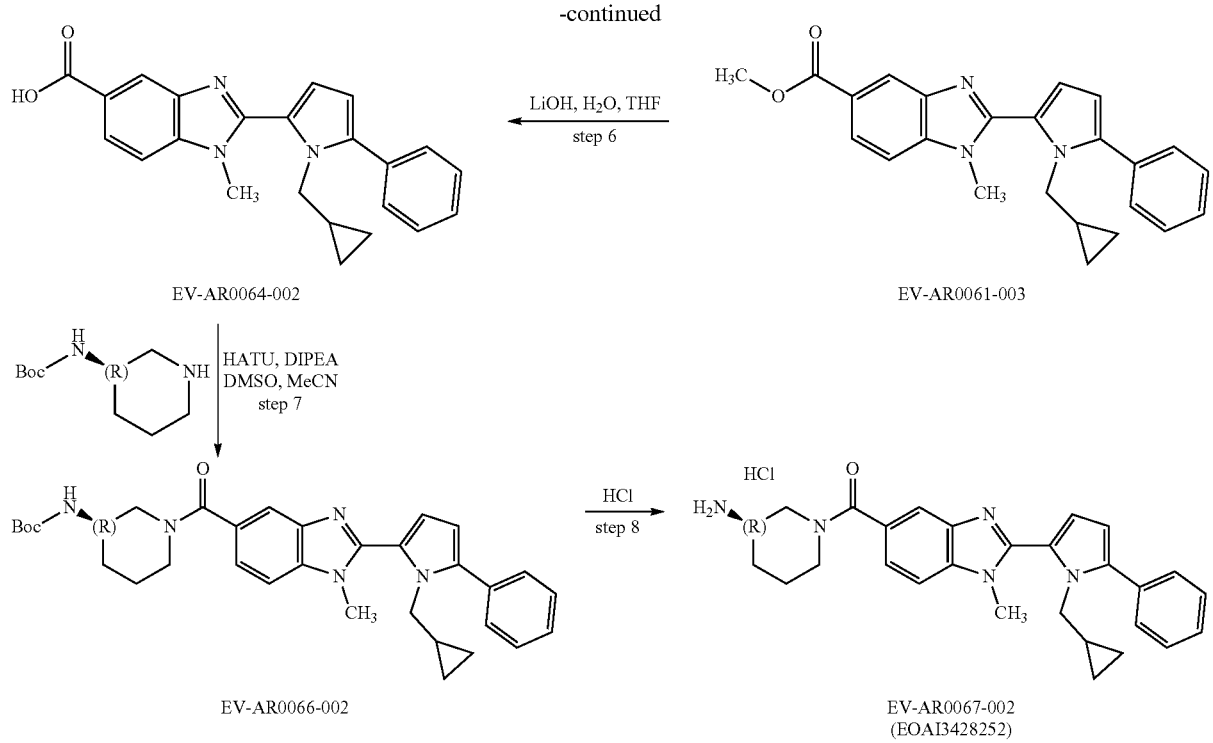

Synthesis of (3R)-1-{2-[1-(cyclopropylmethyl)-5-phenyl-1H-pyrrol-2-yl]-1-methyl-1H-1,3-benzodiazole-5-carbonyl}piperidin-3-amine hydrochloride I-9 EOAI3428252 (EV-AR0067-002)

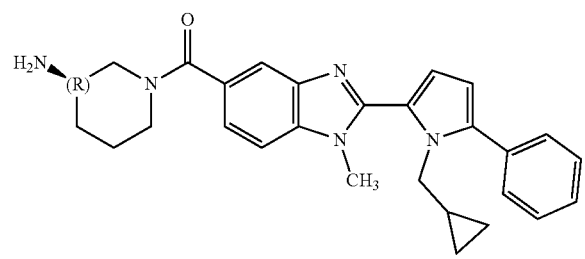

Methyl 5-phenyl-1H-pyrrole-2-carboxylate (EV-AR0054-002)—Step 1

To a solution of 5-phenyl-1H-pyrrole-2-carboxylic acid (500 mg, 2.67 mmol) in toluene (10 ml) and methanol (3 ml) was added 2M (diazomethyl)(trimethyl)silane in hexane (2 ml) and the mixture was stirred under nitrogen at room temperature for 30 minutes. To the reaction mixture was added acetic acid (1 ml) and the mixture was concentrated in vacuo to afford 530 mg (99%) of methyl 5-phenyl-1H-pyrrole-2-carboxylate (EV-AR0054-002) as a pale yellow powder. LCMS (method D): retention time 1.14 min, M/z=202.0 (M+1).

1-(Cyclopropylmethyl)-5-phenyl-1H-pyrrole-2-carboxylic acid (EV-AR0056-003)—Step 2

To a solution of methyl 5-phenyl-1H-pyrrole-2-carboxylate (EV-AR0054-002, 530 mg, 2.63 mmol) in anhydrous DMF (10 ml) was added sodium hydride (60%, 120 mg, 3.00 mmol) portion wise and the resulting mixture was stirred for 15 minutes. After this time (bromomethyl)cyclopropane (285 μl, 2.94 mmol) was added and the mixture was stirred under nitrogen at room temperature for 72 h. The mixture was treated with further (bromomethyl)cyclopropane (450 μl, 4.65 mmol) and sodium hydride (60%, 60 mg, 1.50 mmol) and stirred at 40° C. for 30 minutes. The reaction mixture was concentrated in vacuo and the residue was dissolved in ethanol (8 ml) and water (2 ml). 5M aqueous sodium hydroxide (2 ml) was added and the resulting mixture was stirred in a pressure tube at 80° C. for 2 h. The reaction mixture was concentrated in vacuo and taken up in water (5 ml), acidified with 5N aqueous hydrochloric acid (~5 ml) until no further precipitation was observed. The resulting suspension was stirred on an ice bath for 15 minutes and filtered through filter paper under vacuum. The resulting solid was dried to afford 495 mg (78%) of 1-(cyclopropylmethyl)-5-phenyl-1H-pyrrole-2-carboxylic acid (EV-AR0056-003) as a beige powder. LCMS (method D): retention time 1.17 min, M/z=242.0 (M+1).

Methyl 4-(methylamino)-3-nitrobenzoate (EV-AR0020-002)—Step 3

To a stirred solution of methyl 4-fluoro-3-nitrobenzoate (10.0 g, 50.2 mmol) in DMF (100 ml) was added methanamine hydrochloride (1:1) (4.00 g, 59.2 mmol). Potassium carbonate (99%, 9.00 g, 64.5 mmol) was added and the mixture was stirred under nitrogen at room temperature for 18 h. The reaction crude was concentrated in vacuo and partitioned between ethyl acetate (400 ml) and 1M aqueous hydrochloric acid (2×25 ml). The organic layer was washed with brine (25 ml), dried over sodium sulfate, filtered and concentrated in vacuo to afford 6.00 g (57%) of methyl 4-(methylamino)-3-nitrobenzoate (EV-AR0020-002) as a yellow powder. LCMS (method D): retention time 1.23 min, M/z=210.9 (M+1).

Methyl 3-amino-4-(methylamino)benzoate (EV-AR0021-002)—Step 4

To a solution of methyl 4-(methylamino)-3-nitrobenzoate (EV-AR0020-002, 6.00 g, 28.6 mmol) in ethanol (100 ml) was added 10% w/w Pd/C (0.15 g, 1.41 mmol). The reaction mixture was stirred under an atmosphere of hydrogen at room temperature for 18 h. The reaction crude was filtered through Kieselguhr and washed through with methanol (200 ml). The filtrate was concentrated in vacuo to afford 5.00 g (97%) of methyl 3-amino-4-(methylamino)benzoate (EV-AR0021-002) as a purple solid. LCMS (method D): retention time 0.84 min, M/z=181.0 (M+1).

Methyl 2-[1-(cyclopropylmethyl)-5-phenyl-1H-pyrrol-2-yl]-1-methyl-1H-1,3-benzodiazole-5-carboxylate (EV-AR0061-003)—Step 5

To a solution of 1-(cyclopropylmethyl)-5-phenyl-1H-pyrrole-2-carboxylic acid (EV-AR0056-003, 295 mg, 1.22 mmol) in DMF (5 ml) was added DIPEA (225 µl, 1.36 mmol) followed by HATU (520 mg, 1.37 mmol) and the resulting mixture was stirred at room temperature for 30 minutes. Methyl 3-amino-4-(methylamino)benzoate (EV-AR0021-002, 250 mg, 1.39 mmol) was added and the mixture was stirred under nitrogen at room temperature for 3 h, at 60° C. for 3 h and at room temperature for 16 h. The mixture was then concentrated in vacuo, the residue was suspended in acetic acid (3 ml) and the resulting mixture was stirred under nitrogen at 80° C. for 7 h. The solvent was removed in vacuo and the remaining material purified by flash column chromatography (10-25% ethyl acetate/heptane) to obtain a solid which was triturated from diethyl ether (5 ml) to afford 140 mg (29%) of methyl 2-[1-(cyclopropylmethyl)-5-phenyl-1H-pyrrol-2-yl]-1-methyl-H-1,3-benzodiazole-5-carboxylate (EV-AR0061-003) as a white powder. LCMS (method D): retention time 1.28 min, M/z=386.1 (M+1).

2-[1-(cyclopropylmethyl)-5-phenyl-1H-pyrrol-2-yl]-1-methyl-1H-1,3-benzodiazole-5-carboxylic acid (EV-AR0064-002)—Step 6

To a solution of methyl 2-[1-(cyclopropylmethyl)-5-phenyl-1H-pyrrol-2-yl]-1-methyl-1H-1,3-benzodiazole-5-carboxylate (EV-AR0061-003, 140 mg, 0.36 mmol) in THF (3 ml) was added a solution of lithium hydroxide (26 mg, 1.09 mmol) in water (3 ml) and the resulting mixture was stirred under nitrogen at 50° C. for 16 h. The reaction crude was concentrated in vacuo and taken up in water (5 ml), acidified with 5N aqueous hydrochloric acid (~0.5 ml) until no further precipitation was observed. The resulting suspension was allowed to stir for 30 minutes and filtered through filter paper. The resulting solid was dried to afford 130 mg (96%) of 2-[1-(cyclopropylmethyl)-5-phenyl-1H-pyrrol-2-yl]-1-methyl-1H-1,3-benzodiazole-5-carboxylic acid (EV-AR0064-002) as a white powder. LCMS (method D): retention time 1.13 min, M/z=372.0 (M+1).

Tert-butyl N-[(3R)-1-{2-[1-(cyclopropylmethyl)-5-phenyl-1H-pyrrol-2-yl]-1-methyl-1H-1,3-benzodiazole-5-carbonyl}piperidin-3-yl]carbamate (EV-AR0066-002)—Step 7

To a solution of 2-[1-(cyclopropylmethyl)-5-phenyl-1H-pyrrol-2-yl]-1-methyl-1H-1,3-benzodiazole-5-carboxylic acid (EV-AR0064-002, 50 mg, 0.13 mmol) in 2:1 DMSO acetonitrile (3 ml) was added DIPEA (26 µl, 0.16 mmol) followed by HATU (60 mg, 0.16 mmol) and the resulting mixture was stirred at room temperature for 15 minutes. To this solution was added tert-butyl (3R)-piperidin-3-ylcarbamate (30 mg, 0.15 mmol) and the mixture was stirred under nitrogen at room temperature for 16 h. To the mixture was added 3:2 acetonitrile water (0.5 ml), 2:1 DMSO acetonitrile (2 ml) and water (5 ml) and the resulting suspension was filtered through filter paper under vacuum. The solid was washed with water (10 ml) and dried to afford 53 mg (71%) of tert-butyl N-[(3R)-1-{2-[1-(cyclopropylmethyl)-5-phenyl-1H-pyrrol-2-yl]-1-methyl-1H-1,3-benzodiazole-5-carbonyl}piperidin-3-yl]carbamate (EV-AR0066-002) as a white powder. LCMS (method D): retention time 1.20 min, M/z=554.2 (M+1).

(3R)-1-{2-[1-(Cyclopropylmethyl)-5-phenyl-1H-pyrrol-2-yl]-1-methyl-1H-1,3-benzodiazole-5-carbonyl}piperidin-3-amine hydrochloride (I-9)(EV-AR0067-002)—Step 8

To a suspension of tert-butyl N-[(3R)-1-{2-[1-(cyclopropylmethyl)-5-phenyl-1H-pyrrol-2-yl]-1-methyl-1H-1,3-benzodiazole-5-carbonyl}piperidin-3-yl]carbamate (EV-AR0066-002, 53 mg, 0.10 mmol) in methanol (2 ml) was added 4M hydrochloric acid in dioxane (1 ml) and the resulting solution was stirred under air at room temperature for 2 h. The reaction crude was concentrated in vacuo and the residue was freeze-dried from water (4 ml) to obtain 46 mg (98%) of (3R)-1-{2-[1-(cyclopropylmethyl)-5-phenyl-1H-pyrrol-2-yl]-1-methyl-1H-1,3-benzodiazole-5-carbonyl}piperidin-3-amine hydrochloride (EV-AR0067-002) as a white powder. LCMS (method A): retention time 2.17 min, M/z=454.2 (M+1).

Special cases for Scheme 1
I-12
(3R)-1-{2-[1-(Cyclopropylmethyl)-5-(pyridin-2-yl)-1H-pyrrol-2-yl]-1-methyl-1H-1,3-benzodiazole-5-carbonyl}piperidin-3-amine I-12 EV-AS5724-003 (EOAI3435373) was synthesised according to the procedures described in Scheme 1 via methyl 1-(cyclopropylmethyl)-5-(pyridin-2-yl)-1H-pyrrole-2-carboxylate (EV-AS5714-004) synthesised according to Scheme 1.1

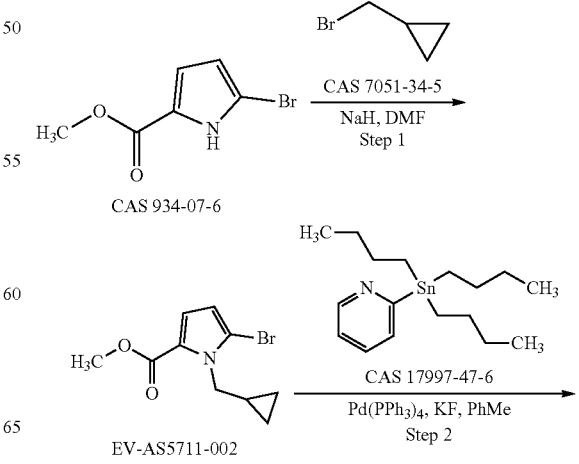

Scheme 1.1

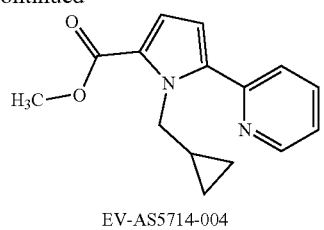

EV-AS5714-004

Methyl 5-bromo-1-(cyclopropylmethyl)-1H-pyrrole-2-carboxylate (EV-AS5711-002)—Step 1

To a solution of methyl 5-bromo-1H-pyrrole-2-carboxylate (CAS 934-07-6, 500 mg, 2.45 mmol) in anhydrous DMF (5 ml) was added sodium hydride (60%, 150 mg, 3.75 mmol). To this solution was added (bromomethyl)cyclopropane (350 μl, 3.61 mmol) and the mixture stirred under nitrogen at 30° C. in a sealed tube for 8 h. The reaction mixture was concentrated, quenched with methanol and purified by flash column chromatography (0-50% ethyl acetate/heptane) to afford 566 mg (89%) of methyl 5-bromo-(cyclopropylmethyl)-1H-pyrrole-2-carboxylate (EV-AS5711-002) as a yellow oil. LCMS (method D): retention time 1.44 min, M/z=258/260 (M+1).

Methyl 1-(cyclopropylmethyl)-5-(pyridin-2-yl)-1H-pyrrole-2-carboxylate (EV-AS5714-004)—Step 2

To a solution of methyl 5-bromo-1-(cyclopropylmethyl)-1H-pyrrole-2-carboxylate (EV-AS5711-002, 566 mg, 2.19 mmol) in toluene (3 ml) was added palladium-triphenylphosphane (1:4) (100 mg, 0.09 mmol). To this solution was added 2-(tributylstannanyl)pyridine (0.84 ml, 2.63 mmol) and the mixture stirred under nitrogen at 110° C. for 18 h. The reaction mixture was cooled, diluted with ethyl acetate (5 ml) and quenched with 1M potassium fluoride (2.5 ml). The mixture was stirred for 15 minutes, the resulting suspension was filtered through Kieselguhr and the filter washed with ethyl acetate (100 ml). The organic layer was washed with 1M potassium fluoride (2×6 ml), saturated aqueous sodium chloride (6 ml) then dried over sodium sulfate, filtered and concentrated. The residue was purified by flash column chromatography (0-50% ethyl acetate/heptane) to afford 176 mg (31%) of methyl 1-(cyclopropylmethyl)-5-(pyridin-2-yl)-1H-pyrrole-2-carboxylate (EV-AS5714-004) as a yellow gum. LCMS (method D): retention time 1.22 min, M/z=257 (M+1).

I-17

(3R)-1-{2-[1-(Cyclopropylmethyl)-5-(pyridin-3-yl)-1H-pyrrol-2-yl]-1-methyl-1H-1,3-benzodiazole-5-carbonyl}piperidin-3-amine I-17 EV-AS5752-002 (EOAI3435970) was synthesised according to the procedures described in Scheme 1 via methyl 1-(cyclopropylmethyl)-5-(pyridin-3-yl)-1H-pyrrole-2-carboxylate (EV-AS5741-002) synthesised according to Scheme 1.2

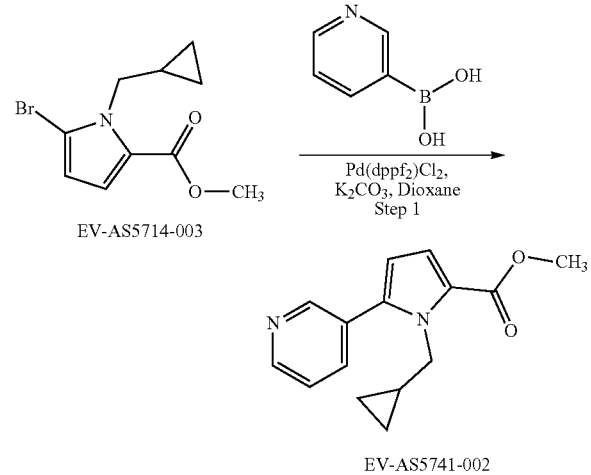

Methyl 1-(cyclopropylmethyl)-5-(pyridin-3-yl)-1H-pyrrole-2-carboxylate (EV-AS5741-002)—Step 1

To a solution of methyl 5-bromo-1-(cyclopropylmethyl)-1H-pyrrole-2-carboxylate (EV-AS5714-003, 135 mg, 0.52 mmol) in dioxane (1 ml) was added pyridin-3-ylboronic acid (75 mg, 0.61 mmol). To this solution was added 1,1'-bis(diphenylphosphanyl)ferrocene-dichloropalladium (1:1) (15 mg, 0.02 mmol) and the mixture stirred under nitrogen at 100° C. for 1 h. The reaction mixture was concentrated and the residue purified by flash column chromatography (8-50% ethyl acetate/heptane) to afford 100 mg (71%) of methyl 1-(cyclopropylmethyl)-5-(pyridin-3-yl)-1H-pyrrole-2-carboxylate (EV-AS5741-002) as a yellow oil. LCMS (method D): retention time 1.08 min, M/z=257 (M+1).

I-22

(3R)-1-{2-[1-(Cyclopropylmethyl)-2-phenyl-1H-imidazol-4-yl]-1-methyl-1H-1,3-benzodiazole-5-carbonyl}piperidin-3-amine I-22 EV-AS5480-001 (EOAI3441169) was synthesised according to the procedures described in Scheme 1 via methyl 1-(cyclopropylmethyl)-2-phenyl-1H-imidazole-4-carboxylate (EV-AS5469-002) synthesised according to Scheme 1.3.

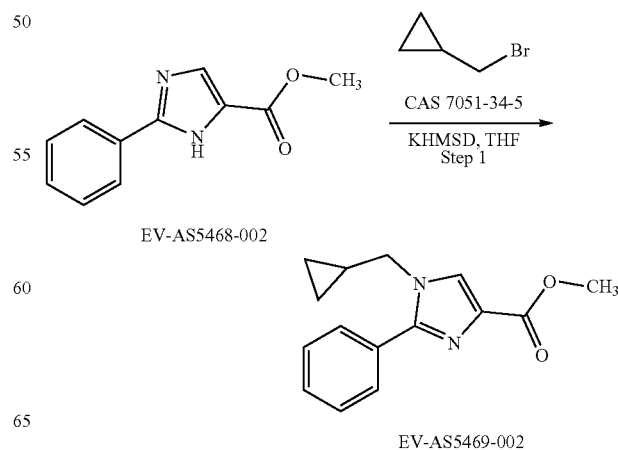

Methyl 1-(cyclopropylmethyl)-2-phenyl-1H-imidazole-4-carboxylate (EV-AS5469-002)—Step 1

To a solution of methyl 2-phenyl-H-imidazole-5-carboxylate (EV-AS5468-002 prepared as described in scheme 1.10, 683 mg, 3.38 mmol) in THE (20 ml) at 0° C. was added potassium hexamethyldisilazane (15% solution in toluene, 5.64 ml, 3.72 mmol) and stirred for 5 mins, before (bromomethyl)cyclopropane (360 µl, 3.72 mmol) was added and stirred at 70° C. for 20 h. The reaction mixture was cooled to 0° C. and saturated aqueous ammonium chloride (20 ml) was added. The reaction mixture was extracted with DCM (2×20 ml), the organic extracts were dried over sodium sulfate and concentrated. The residue was purified by flash column chromatography (0-50% ethyl acetate/heptane) to afford 381 mg (43%) of methyl 1-(cyclopropylmethyl)-2-phenyl-1H-imidazole-4-carboxylate (EV-AS5469-002) as a beige powder. LCMS (method D): retention time 1.12 min, M/z=257 (M+1).

I-32

(3R)-1-{2-[1-(Cyclopropylmethyl)-5-(2-phenylethyl)-1H-pyrrol-2-yl]-1-methyl-1H-1,3-benzodiazole-5-carbonyl}piperidin-3-amine hydrochloride I-32 EV-AU3425-003 (EOA13447741) was obtained according to Scheme 1.4 from tert-butyl N-[(3R)-1-{2-[1-(cyclopropylmethyl)-5-[(E)-2-phenylethenyl]-1H-pyrrol-2-yl]-1-methyl-H-1,3-benzodiazole-5-carbonyl}piperidin-3-yl]carbamate (EV-AU3418-004) which was synthesised according to the procedures described in Schemes 1 and 1.1.

(3R)-1-{2-[1-(cyclopropylmethyl)-5-(2-phenylethyl)-1H-pyrrol-2-yl]-1-methyl-1H-1,3-benzodiazole-5-carbonyl}piperidin-3-amine hydrochloride (EV-AU3425-003)—Step 1

To a solution of tert-butyl N-[(3R)-1-{2-[1-(cyclopropylmethyl)-5-[(E)-2-phenylethenyl]-1H-pyrrol-2-yl]-1-methyl-1H-1,3-benzodiazole-5-carbonyl}piperidin-3-yl]carbamate (EV-AU3418-004, 17 mg, 0.03 mmol) in ethanol (2 ml) was added 10% w/w Pd/C (2 mg, 0.02 mmol). The mixture was stirred for 5 h at room temperature under a hydrogen atmosphere and filtered through Kieselguhr. The filter was washed with methanol (20 ml) and the filtrate was concentrated in vacuo. The obtained material was dissolved in DCM (2 ml) and 2M hydrogen chloride in diethyl ether (0.5 ml) was added. The mixture was stirred for 2 h at room temperature. The solvents were then removed under a stream of nitrogen and the material further dried in a vacuum oven for 16 h to obtain 13 mg (85%) of (3R)-1-{2-[1-(cyclopropylmethyl)-5-(2-phenylethyl)-1H-pyrrol-2-yl]-1-methyl-1H-1,3-benzodiazole-5-carbonyl}piperidin-3-amine hydrochloride (EV-AU3425-003) as a white powder. LCMS (method A): retention time 2.48 min, M/z=482 (M+1).

I-21

(3R)-1-{2-[1-(Cyclopropylmethyl)-1H-pyrrol-2-yl]-1-methyl-1H-1,3-benzodiazole-5-carbonyl}piperidin-3-amine hydrochloride I-21 EV-AS5766-001 (EOA13437830) was obtained from boc-deprotection of tert-butyl N-[(3R)-1-{2-[1-(cyclopropylmethyl)-1H-pyrrol-2-yl]-1-methyl-1H-1,3-benzodiazole-5-carbonyl}piperidin-3-yl]carbamate (EV-AS5765-002) obtained according to Scheme 1.5 starting from of tert-butyl N-[(3R)-1-{2-[5-bromo-1-(cyclopropylmethyl)-1H-pyrrol-2-yl]-1-methyl-H-1,3-benzodiazole-5-carbonyl}piperidin-3-yl]carbamate (EV-AS5763-002) which was synthesised according to the procedures described in Scheme 1.

Scheme 1.4

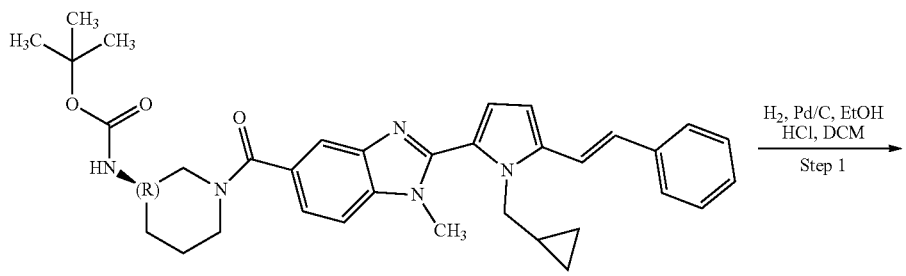

EV-AU3418-004

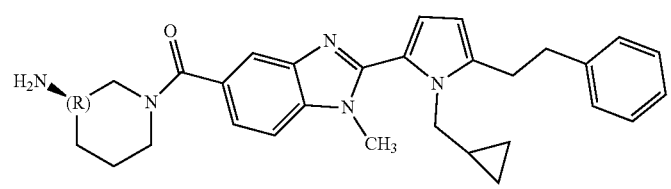

EV-AU3425-003

Scheme 1.5

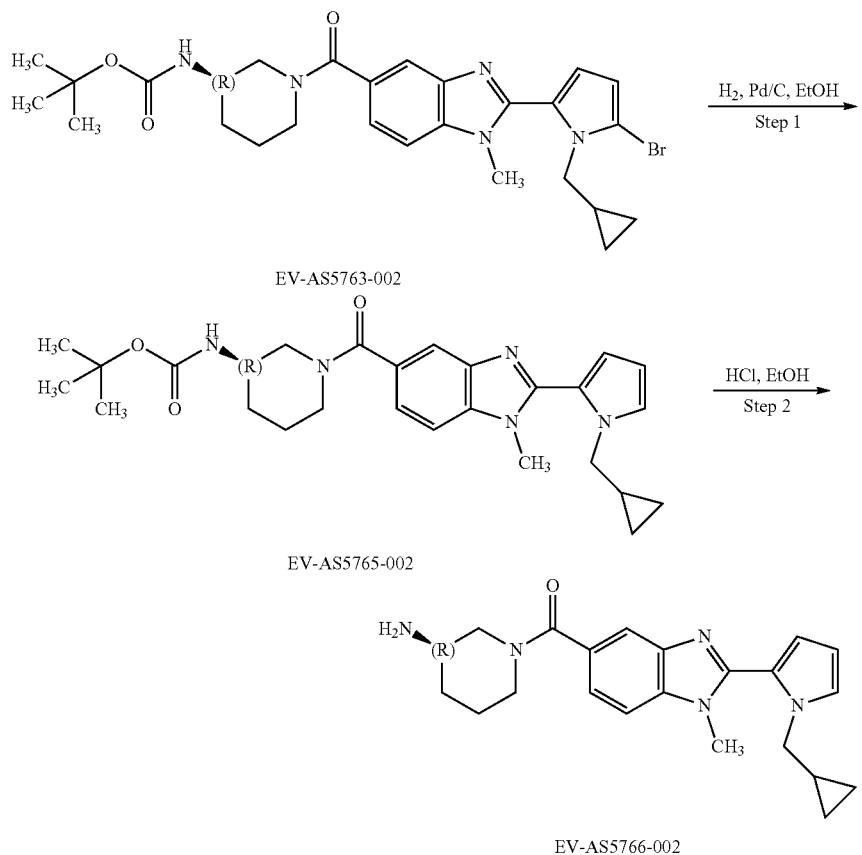

Tert-butyl N-[(3R)-1-{2-[1-(cyclopropylmethyl)-1H-pyrrol-2-yl]-1-methyl-1H-1,3-benzodiazole-5-carbonyl}piperidin-3-yl]carbamate (EV-AS5765-001)—Step 1

To a solution of tert-butyl N-[(3R)-1-{2-[5-bromo-1-(cyclopropylmethyl)-1H-pyrrol-2-yl]-1-methyl-1H-1,3-benzodiazole-5-carbonyl}piperidin-3-yl]carbamate (EV-AS5763-002, 50 mg, 0.09 mmol, synthesised according to procedures described in Scheme 1) in ethanol (2 ml) was added 10% w/w Pd/C (5 mg, 0.05 mmol). The mixture was stirred for 17 h at room temperature under a hydrogen atmosphere and filtered through Kieselguhr. The filter was washed with methanol (40 ml) and the filtrate was concentrated in vacuo to obtain 43 mg (99%) of tert-butyl N-[(3R)-1-{2-[1-(cyclopropylmethyl)-1H-pyrrol-2-yl]-1-methyl-1H-1,3-benzodiazole-5-carbonyl}piperidin-3-yl]carbamate (EV-AS5765-002) as a white powder. LCMS (method D): retention time 1.07 min, M/z=478 (M+1).

(3R)-1-{2-[1-(cyclopropylmethyl)-1H-pyrrol-2-yl]-1-methyl-1H-1,3-benzodiazole-5-carbonyl}piperidin-3-amine hydrochloride (EV-AS5766-002)—Step 2

To a solution of tert-butyl N-[(3R)-1-{2-[1-(cyclopropylmethyl)-1H-pyrrol-2-yl]-1-methyl-1H-1,3-benzodiazole-5-carbonyl}piperidin-3-yl]carbamate (EV-AS5765-002, 40 mg, 0.08 mmol) in ethanol (1 ml) was added 1.25M hydrogen chloride in ethanol (1 ml). The mixture was stirred for 4.5 h at 40° C. The solvent was removed under a stream of nitrogen and the residue was purified by basic HPLC preparative method. The residue was dissolved in 2M aqueous hydrogen chloride (1 ml) and the solvent was removed in vacuo. The residue was dissolved in water (4 ml) and dried on a freeze dryer to obtain 31 mg (89%) of (3R)-1-{2-[1-(cyclopropylmethyl)-1H-pyrrol-2-yl]-1-methyl-1H-1,3-benzodiazole-5-carbonyl}piperidin-3-amine hydrochloride (EV-AS5766-002) as a yellow powder. LCMS (method A): retention time 1.46 min, M/z=378 (M+1).

I-6 and I-7

(3R)-1-[2-(1-Cyclobutyl-3-cyclopropyl-1H-pyrazol-5-yl)-1-methyl-1H-1,3-benzodiazole-5-carbonyl]piperidin-3-amine I-6 EV-AR0050-002 (EOA13427617) was synthesised according to the procedures described in Scheme 1 via synthesis of methyl 1-cyclobutyl-3-cyclopropyl-1H-pyrazole-5-carboxylate (EV-AR0034-003) as described in Scheme 1.6. (3R)-1-[2-(1-cyclobutyl-5-cyclopropyl-1H-pyrazol-3-yl)-1-methyl-H-1,3-benzodiazole-5-carbonyl]piperidin-3-amine I-7 EV-AR0051-002 (EOA13427618) was synthesised according to the procedures described in Scheme 1 via synthesis of methyl 1-cyclobutyl-5-cyclopropyl-1H-pyrazole-3-carboxylate (EV-AR0034-004) as described in Scheme 1.6.

Scheme 1.6

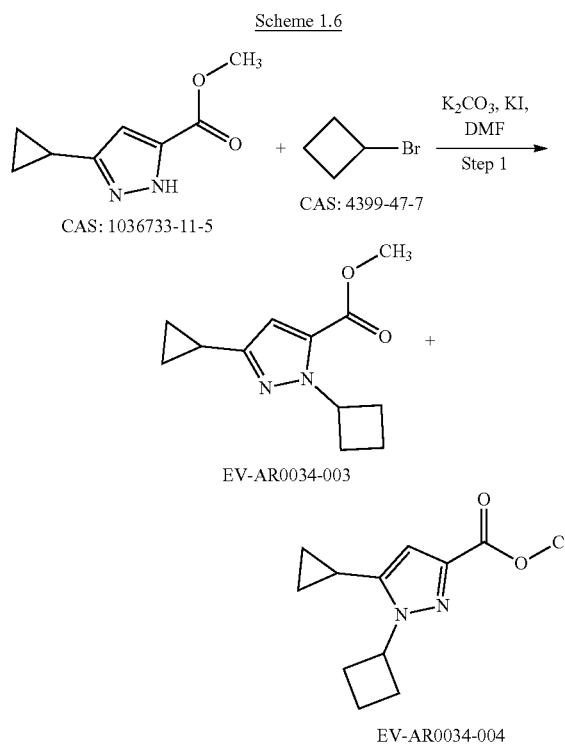

Methyl 1-cyclobutyl-3-cyclopropyl-1H-pyrazole-5-carboxylate (EV-AR0034-003) and methyl 1-cyclobutyl-5-cyclopropyl-1H-pyrazole-3-carboxylate (EV-AR0034-004)—Step 1

To a solution of methyl 3-cyclopropyl-1H-pyrazole-5-carboxylate (CAS 1036733-11-5, 500 mg, 3.01 mmol) in DMF (5 ml) were added potassium carbonate (832 mg, 6.02 mmol), potassium iodide (750 mg, 4.52 mmol) and bromocyclobutane (CAS 4399-47-7, 315 μl, 3.35 mmol). The resulting mixture was stirred for 17 h at 80° C. Additional bromocyclobutane (70 μl, 0.74 mmol) was added and the mixture stirred for 24 h at 80° C. The solvent was removed in vacuo, the residue was dissolved in ethyl acetate (100 ml), washed with water (3×10 ml) then saturated sodium chloride (10 ml). The organic extract was dried over sodium sulfate and concentrated in vacuo. The crude material was purified by flash column chromatography (25% ethyl acetate/heptane) to obtain 2 products.

First eluting isomer: 230 mg (31%) of methyl 1-cyclobutyl-3-cyclopropyl-1H-pyrazole-5-carboxylate (EV-AR0034-003) as a yellow oil. LCMS (method D): retention time 1.26 min, M/z=221 (M+1).

Second eluting isomer: 130 mg (19%) of methyl 1-cyclobutyl-5-cyclopropyl-1H-pyrazole-3-carboxylate (EV-AR0034-004) as a colourless oil. LCMS (method D): retention time 1.12 min, M/z=221 (M+1).

I-36

(3R)-1-{2-[1-(Cyclopropylmethyl)-4-methyl-2-phenyl-1H-imidazol-5-yl]-1-methyl-1H-1,3-benzodiazole-5-carbonyl}piperidin-3-amine EV-AU7213-001 (EOAI3447871) was synthesised according to the procedures described in Scheme 1 via 1-(cyclopropylmethyl)-4-methyl-2-phenyl-1H-imidazole-5-carboxylic acid EV-AT8656-001 synthesised according to Scheme 1.7.

Scheme 1.7

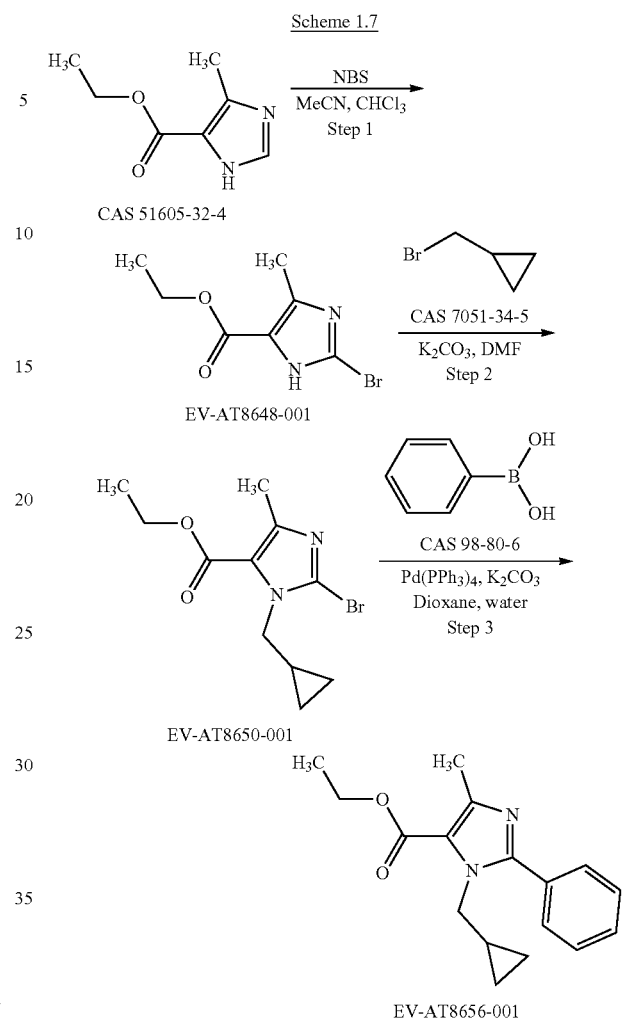

Ethyl 2-bromo-4-methyl-1H-imidazole-5-carboxylate (EV-AT8648-001)—Step 1

To a stirred solution of ethyl 4-methyl-H-imidazole-5-carboxylate (CAS 51605-32-4, 500 mg, 3.24 mmol) in acetonitrile (10 ml) and chloroform (10 ml) was added N-bromosuccinimide (577 mg, 3.24 mmol) and the reaction stirred under a nitrogen atmosphere at room temperature for 18 h. The reaction mixture was concentrated and the residue was purified by flash column chromatography (10-100% ethyl acetate/heptane) to afford 560 mg (73%) of ethyl 2-bromo-4-methyl-1H-imidazole-5-carboxylate (EV-AT8648-001) as an off-white solid. LCMS (method D): retention time 0.87 min, M/z=233/235 (M+1).

Ethyl 2-bromo-1-(cyclopropylmethyl)-4-methyl-1H-imidazole-5-carboxylate (EV-AT8650-001)—Step 2

To ethyl 2-bromo-4-methyl-1H-imidazole-5-carboxylate (EV-AT8648-001, 550 mg, 2.36 mmol) in DMF (10 ml), was added potassium carbonate (652 mg, 4.72 mmol) followed by (bromomethyl)cyclopropane (0.25 ml, 2.60 mmol) and the reaction mixture stirred at room temperature for 16 h. Saturated aqueous ammonium chloride (150 ml) was added to the reaction mixture and the aqueous layer was extracted with ethyl acetate (2×150 ml). The combined organics were then dried over sodium sulfate and concentrated in vacuo.

The residue was purified by flash column chromatography (0-100% ethyl acetate/heptane) to afford 543 mg (80%) of ethyl 2-bromo-1-(cyclopropylmethyl)-4-methyl-1H-imidazole-5-carboxylate (EV-AT8650-001) as a colourless oil. LCMS (method D): retention time 1.23 min, M/z=287/289 (M+1).

1-(Cyclopropylmethyl)-4-methyl-2-phenyl-1H-imidazole-5-carboxylic acid (EV-AT8656-001)—Step 3

A pressure tube was charged with ethyl 2-bromo-1-(cyclopropylmethyl)-4-methyl-1H-imidazole-5-carboxylate (EV-AT8650-001, 200 mg, 0.70 mmol), phenylboronic acid (127 mg, 1.04 mmol), tetrakis(triphenylphosphine)palladium(0) (20 mg, 0.017 mmol) and potassium carbonate (154 mg, 1.11 mmol) in dioxane (2 ml) and water (0.67 ml). The mixture was purged with nitrogen for 10 minutes and stirred at 100° C. for 3 h. The reaction mixture was partitioned between ethyl acetate (100 ml) and water (80 ml). The organic extract was dried over sodium sulfate and concentrated. The residue was purified using flash column chromatography (0-35% ethyl acetate/heptane) to afford 172 mg (82%) of 1-(cyclopropylmethyl)-4-methyl-2-phenyl-1H-imidazole-5-carboxylic acid (EV-AT8656-001) as a yellow oil. LCMS (method D): retention time 1.05 min, M/z=285 (M+1).

I-43

5-{5-[(3R)-3-Aminopiperidine-1-carbonyl]-7-methoxy-1-methyl-1H-1,3-benzodiazol-2-yl}-N-benzyl-1-(cyclopropylmethyl)-N-phenyl-1H-pyrrole-2-carboxamide I-43 EV-AU3468-002 (EOAI3450849) was synthesised according to the procedures described in Scheme 1 via synthesis of 5-[benzyl(phenyl)carbamoyl]-1-(cyclopropylmethyl)-1H-pyrrole-2-carboxylic acid (EV-AU3461-003) as described in Scheme 1.8.

Scheme 1.8

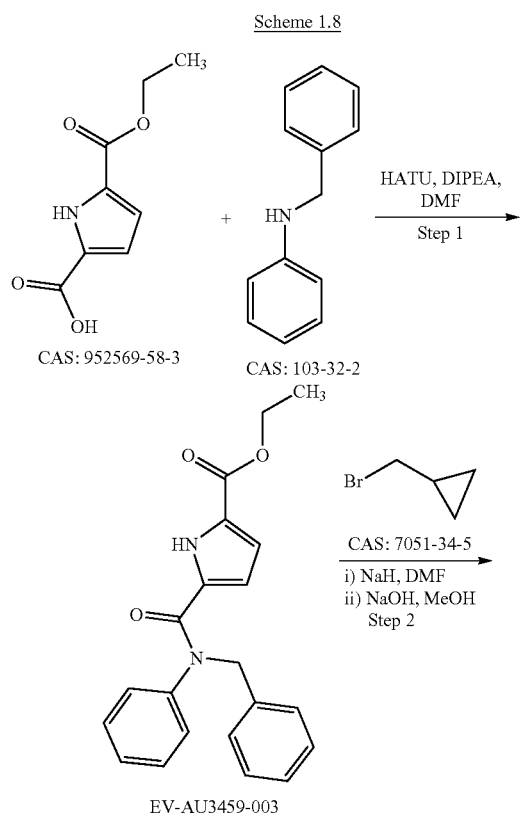

EV-AU3459-003

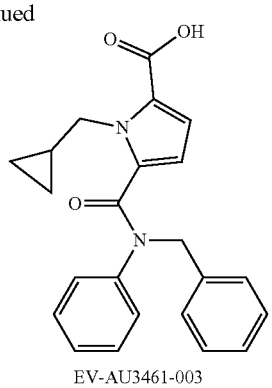

EV-AU3461-003

Ethyl 5-[benzyl(phenyl)carbamoyl]-1H-pyrrole-2-carboxylate (EV-AU3459-003)—Step 1

To a solution of 5-(ethoxycarbonyl)-1H-pyrrole-2-carboxylic acid (CAS 952569-58-3, 200 mg, 1.09 mmol) in DMF (5 ml) was added DIPEA (190 µl, 1.15 mmol) followed by HATU (436 mg, 1.15 mmol). The reaction was stirred for 30 minutes and N-benzylaniline (CAS 103-32-2, 220 mg, 1.20 mmol) was added. The mixture was stirred under nitrogen for 17 h at room temperature then for 23 h at 50° C. The reaction mixture was concentrated in vacuo and the residue diluted with DCM (30 ml) and water (25 ml). The aqueous layer was extracted with DCM (2×30 ml) and the combined organic extracts were washed with water (2×10 ml), saturated aqueous sodium chloride (10 ml), dried over sodium sulfate and concentrated in vacuo. The crude material was purified by flash column chromatography (100% DCM) to obtain 174 mg (46%) of ethyl 5-[benzyl(phenyl)carbamoyl]-1H-pyrrole-2-carboxylate EV-AU3459-003 as a white powder. LCMS (method D): retention time 2.28 min. M/z=349 (M+1).

5-[benzyl(phenyl)carbamoyl]-1-(cyclopropylmethyl)-1H-pyrrole-2-carboxylic acid (EV-AU3461-003)—Step 2

To a solution of ethyl 5-[benzyl(phenyl)carbamoyl]-1H-pyrrole-2-carboxylate (174 mg, 0.50 mmol) in anhydrous DMF (3 ml) was added sodium hydride (60%, 30.1 mg, 0.75 mmol) followed by (bromomethyl)cyclopropane (73 µl, 0.75 mmol). The resulting mixture was stirred for 17 h under nitrogen at room temperature then for 8 h at 50° C. then for 52 h at room temperature. The reaction mixture was concentrated in vacuo and the residue was dissolved in methanol (5 ml). 5M aqueous sodium hydroxide (0.86 ml) was added and the reaction was stirred for 6 h at 50° C. The reaction was allowed to cool to room temperature and acidified with 5N aqueous hydrogen chloride (6 ml). The resulting suspension was concentrated in vacuo and taken up in water (3 ml). The suspension was then filtered and the solid allowed to air dry to obtain 55 mg (83%) of 5-[benzyl(phenyl)carbamoyl]-1-(cyclopropylmethyl)-1H-pyrrole-2-carboxylic acid (EV-AU3461-003) as a pale yellow solid. LCMS (method D): retention time 1.23 min. M/z=375 (M+1).

I-48

5-{5-[(3R)-3-Aminopiperidine-1-carbonyl]-7-methoxy-1-methyl-1H-1,3-benzodiazol-2-yl}-1-(cyclopropylmethyl)-N-phenyl-1H-pyrrole-2-carboxamide I-48

EV-AU3491-002 (EOAI3454072) was synthesised according to the procedures described in Scheme 1 via synthesis of ethyl 1-(cyclopropylmethyl)-5-(phenylcarbamoyl)-1H-pyrrole-2-carboxylate (EV-AU3483-002) as described in Scheme 1.9.

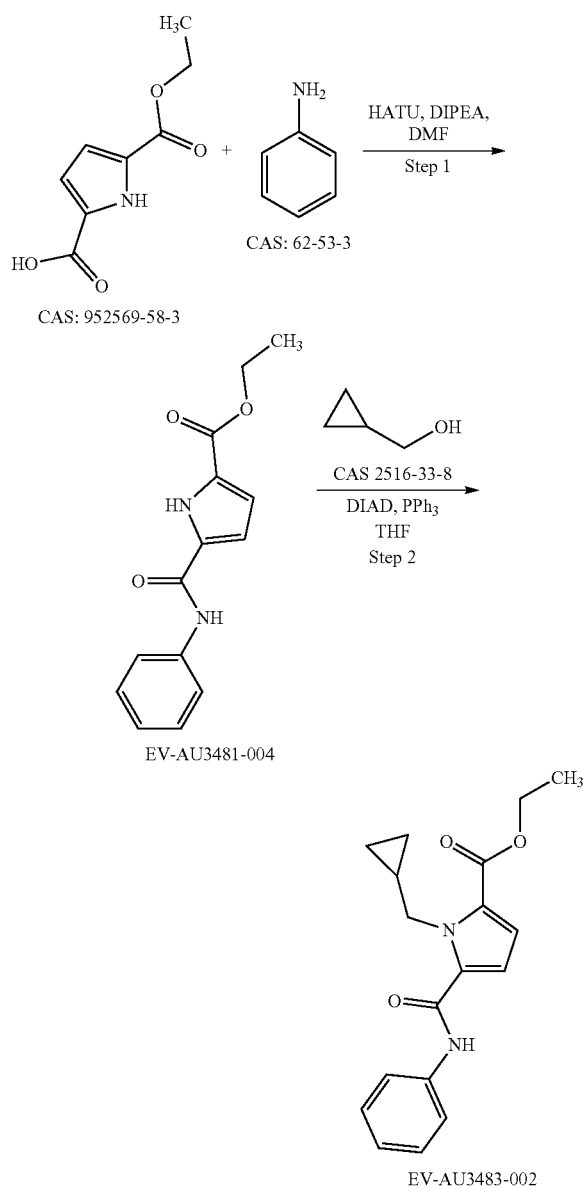

Ethyl 5-(phenylcarbamoyl)-1H-pyrrole-2-carboxylate (EV-AU3481-004)—Step 1

To a solution of 5-(ethoxycarbonyl)-1H-pyrrole-2-carboxylic acid (CAS 952569-58-3, 100 mg, 0.55 mmol) in DMF (2 ml) was added DIPEA (110 µl, 0.67 mmol) followed by HATU (250 mg, 0.66 mmol). After stirring for 15 minutes, aniline (CAS 62-53-3, 60 µl, 0.66 mmol) was added and the mixture was stirred under nitrogen for 1.5 h at room temperature. The reaction mixture was concentrated in vacuo, the residue was diluted with ethyl acetate (100 ml) and washed with 1N aqueous hydrogen chloride (2×20 ml), water (3×20 ml) then saturated aqueous sodium chloride (20 ml). The organic extract was dried over sodium sulfate and concentrated in vacuo to afford the crude material which was purified by flash column chromatography (0-1% MeOH/DCM) to obtain 114 mg (81%) of ethyl 5-(phenylcarbamoyl)-1H-pyrrole-2-carboxylate (EV-AU3481-004) as a white powder. LCMS (method D): retention time 1.08 min, M/z=259 (M+1).

Ethyl 1-(cyclopropylmethyl)-5-(phenylcarbamoyl)-1H-pyrrole-2-carboxylate (EV-AU3483-002)—Step 2

To a solution of DIAD (174 µl, 0.88 mmol) in anhydrous THF (5 ml) was added triphenylphosphane (232 mg, 0.88 mmol) at −20° C. After stirring for 30 minutes a solution of ethyl 5-(phenylcarbamoyl)-1H-pyrrole-2-carboxylate (EV-AU3481-004, 114 mg, 0.44 mmol) in anhydrous THF (5 ml) was added. The solution was stirred for a further 30 minutes, then cyclopropylmethanol (54 µl, 0.67 mmol) was added and the mixture was allowed to reach room temperature over 17 h under an atmosphere of nitrogen. The solvent was removed in vacuo and the crude material was purified by flash column chromatography (5-25% ethyl acetate/heptane) to obtain 150 mg (80%) of ethyl 1-(cyclopropylmethyl)-5-(phenylcarbamoyl)-1H-pyrrole-2-carboxylate (EV-AU3483-002) as a white powder. LCMS (method D): retention time 1.29 min, M/zz=313 (M+1).

I-23

(3R)-1-{2-[1-(cyclopropylmethyl)-2-phenyl-1H-imidazol-5-yl]-1-methyl-1H-1,3-benzodiazole-5-carbonyl}piperidin-3-amine I-23 EV-AT8676-001 (EOAI3441286) was synthesised according to the procedures described in Scheme 1 via synthesis of methyl 1-(cyclopropylmethyl)-2-phenyl-1H-imidazole-5-carboxylate (EV-AT8667-001) as described in Scheme 1.10.

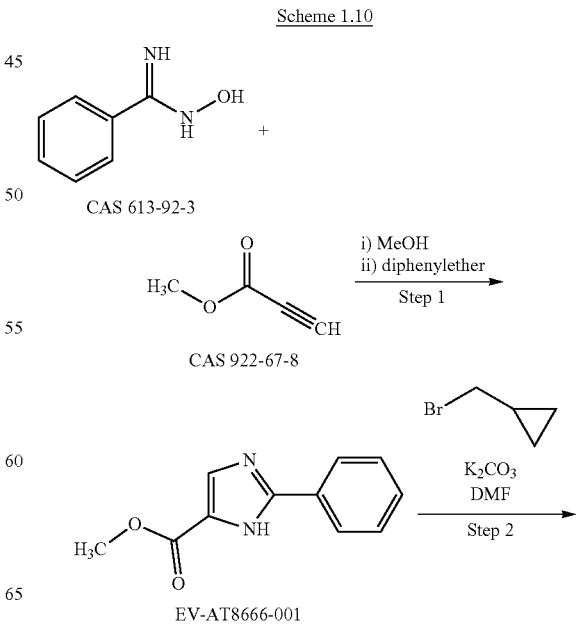

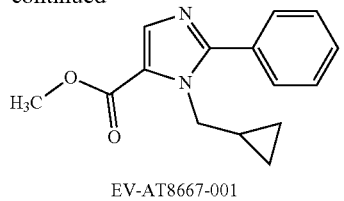

EV-AT8667-001

Methyl 2-phenyl-1H-imidazole-5-carboxylate (EV-AT8666-001)—Step 1

To a suspension of N-hydroxybenzenecarboximidamide (CAS 613-92-3, 3.91 g, 28.7 mmol) in methanol (20 ml) was added methyl prop-2-ynoate (CAS 922-67-8, 2.55 ml, 28.7 mmol). The mixture was stirred at 60° C. under nitrogen for 1 h, concentrated in vacuo, azeotroped with toluene (20 ml) and the solvents were removed in vacuo. Diphenyl ether was added to the resulting solid and the mixture was stirred at 200° C. for 30 minutes. The reaction was allowed to cool to room temperature and diethyl ether (100 ml) was added. The resulting solid was filtered off and purified by flash column chromatography (10-80% ethyl acetate/heptane) to obtain 0.52 g (8.6%) of methyl 2-phenyl-1H-imidazole-5-carboxylate (EV-AT8666-001) as an off white powder. LCMS (method D): retention time 0.80 min, M/z=203 (M+1).

Methyl 1-(cyclopropylmethyl)-2-phenyl-1H-imidazole-5-carboxylate (EV-AT8667-001)—Step 2

To a suspension of methyl 2-phenyl-H-imidazole-4-carboxylate (EV-AT8666-001, 624 mg, 3.09 mmol) and potassium carbonate (853 mg, 6.17 mmol) in DMF (10 ml) was added (bromomethyl)cyclopropane (0.36 ml, 3.70 mmol). The mixture was left stirring for 16 h at room temperature then the mixture was partitioned between ethyl acetate (100 ml) and water (100 ml). The organic extract was dried over sodium sulfate, filtered and concentrated. The residue was purified by flash column chromatography (10-60% ethyl acetate/heptane) to obtain 235 mg (29%) of methyl 1-(cyclopropylmethyl)-2-phenyl-1H-imidazole-5-carboxylate (EV-AT8667-001) as a yellow oil. LCMS (method D): retention time 1.05 min, M/z=257 (M+1).

I-58
(3R)-1-[2-(1-Benzyl-2-methyl-1H-imidazol-4-yl)-7-methoxy-1-methyl-1H-1,3-benzodiazole-5-carbonyl]piperidin-3-amine I-58 EV-AW5508-001 (EOAI3456187) was synthesised according to the procedures described in Scheme 1 via the synthesis of methyl 1-benzyl-2-methyl-1H-imidazole-4-carboxylate (EV-AV3888-001) as described in Scheme 1.11.

Scheme 1.11

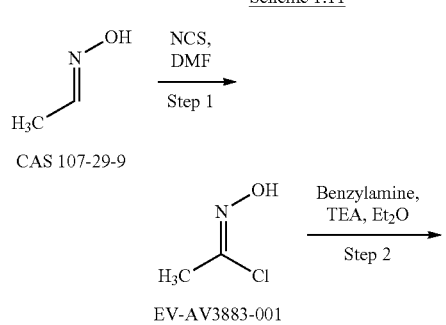

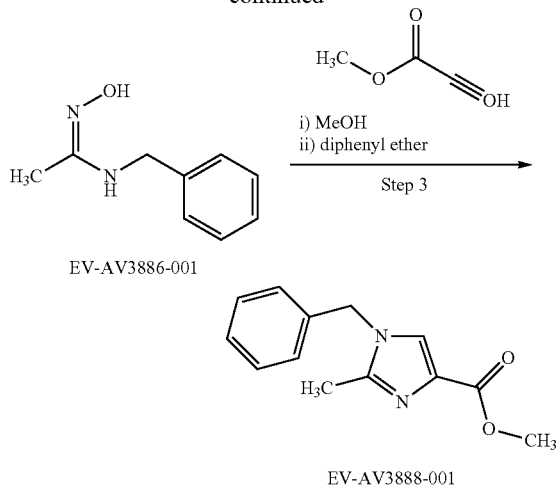

(Z)—N-hydroxyethenecarbonimidoyl chloride (EV-AV3883-001)—Step 1

To a solution of (E)-N-ethylidenehydroxylamine (CAS 107-29-9, 0.50 g, 8.46 mmol) in DMF (20 mL) was added 1-chloropyrrolidine-2,5-dione (685.06 µl, 8.46 mmol) and the reaction was left to stir at room temperature for 2 h. The mixture was diluted with water (10 ml) and extracted with ethyl acetate (2×10 ml). The combined organic extracts were washed with water (3×10 ml), saturated aqueous sodium chloride (10 ml), dried over sodium sulfate and concentrated in vacuo to obtain 0.79 g (assumed quantitative) of (Z)—N-hydroxyethenecarbonimidoyl chloride (EV-AV3883-001) as a colourless oil.

(Z)—N-benzyl-N'-hydroxyethenimidamide (EV-AV3886-001)—Step 2

To a solution of (Z)—N-hydroxyethenecarbonimidoyl chloride (EV-AV3883-001, 0.80 g, 8.56 mmol) in diethyl ether (20 ml) at 0° C. was added triethylamine (1.19 ml, 8.56 mmol) and phenylmethanamine (0.93 ml, 8.56 mmol) and the reaction was stirred at 0° C. for 2 h. The mixture was then diluted with water (10 ml) and extracted with DCM (3×10 ml). The combined organic extracts were washed with water (10 ml), saturated aqueous sodium chloride (10 ml), dried over sodium sulfate and concentrated in vacuo to obtain 730 mg (52%) of (Z)—N-benzyl-N'-hydroxyethenimidamide (EV-AV3886-001) as a white powder. LCMS (method D): retention time 0.37 min, M/z=165 (M+1).

Methyl 1-benzyl-2-methyl-1H-imidazole-4-carboxylate (EV-AV3888-001)—Step 3

To a solution of (Z)—N-benzyl-N'-hydroxyethenimidamide (EV-AV3886-001, 730 mg, 4.45 mmol) in methanol (12 ml) was added methyl prop-2-ynoate (CAS 922-67-8, 404.26 µl, 4.54 mmol). The mixture was stirred at 65° C. under nitrogen for 5 h. The mixture was then concentrated in vacuo, toluene (3 ml) was added and the mixture was concentrated in vacuo to afford an orange oil. Diphenyl ether (12 ml) was added and the mixture was left stirring at 200° C. for 20 minutes. The reaction was cooled to room temperature and the mixture was purified by flash column chromatography (10-100% ethyl acetate/heptanes then 0-20% MeOH/ethyl acetate) to obtain 320 mg (30%) of methyl 1-benzyl-2-methyl-1H-imidazole-4-carboxylate (EV-AV3888-001) as a brown oil. LCMS (method D): retention time 0.77 min, M/z=231 (M+1).

I-55

5-{5-[(3R)-3-Aminopiperidine-1-carbonyl]-7-methoxy-1-methyl-1H-1,3-benzodiazol-2-yl}-1-benzyl-1H-pyrrole-2-carbonitrile I-55 EV-AW5300-001 (EOAI3455897) was synthesised according to the procedures described in Scheme 1 via the synthesis of methyl 1-benzyl-5-cyano-1H-pyrrole-2-carboxylate (EV-AU7292-001) as described in Scheme 1.12.

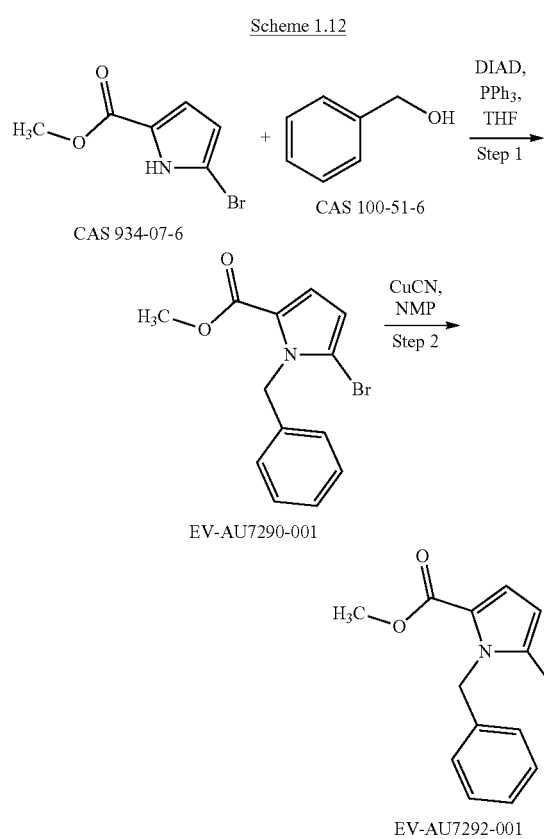

Methyl 1-benzyl-5-bromo-1H-pyrrole-2-carboxylate (EV-AU7290-001)—Step 1

To a solution of DIAD (1.03 ml, 4.90 mmol) in dry THF (5 ml) under nitrogen at −20° C. was added a solution of triphenylphosphine (1.30 g, 4.90 mmol) in dry THF (10 ml). The mixture was stirred for 30 minutes and a solution of methyl 5-bromo-1H-pyrrole-2-carboxylate (CAS 934-07-6, 500 mg, 2.45 mmol) in dry THF (5 ml) was added. The mixture was stirred at −20° C. for a further 30 minutes and phenylmethanol (CAS 100-51-6, 0.38 ml, 3.67 mmol) in dry THF (5 ml) was added dropwise at −20° C. and the reaction mixture was allowed to warm to room temperature and stirred for 62 h. The solvent was removed in vacuo and the crude material was purified by flash column chromatography (5-30% ethyl acetate/heptane) to obtain 730 mg (99%) of methyl 1-benzyl-5-bromo-1H-pyrrole-2-carboxylate (EV-AU7290-001) as a pale yellow oil. LCMS (method D): retention time 1.32 min, M/z=294/296 (M+1).

Methyl 1-benzyl-5-cyano-1H-pyrrole-2-carboxylate (EV-AU7292-001)—Step 2

To a solution of methyl 1-benzyl-5-bromo-1H-pyrrole-2-carboxylate (EV-AU7290-001, 300 mg, 1.00 mmol) in NMP (5 ml) was added copper cyanide (107 mg, 1.2 mmol). The resulting mixture was heated at 160° C. in a sealed tube for 16 h. The reaction was allowed to cool to room temperature and poured into an aqueous 10% EDTA solution in 1M sodium hydroxide (30 ml). The resulting mixture was stirred at room temperature for 30 minutes. The aqueous mixture was extracted with ethyl acetate (3×20 ml) and the combined organic extracts were washed with saturated aqueous sodium chloride (10 ml), dried over sodium sulfate and concentrated in vacuo. The crude material was purified by flash column chromatography (5-30% ethyl acetate/heptane) to obtain 142 mg (58%) of methyl 1-benzyl-5-cyano-1H-pyrrole-2-carboxylate (EV-AU7292-001) as a colourless oil. LCMS (method D): retention time 1.21 min, M/z=241 (M+1).

I-56

5-{5-[(3R)-3-Aminopiperidine-1-carbonyl]-7-methoxy-1-methyl-1H-1,3-benzodiazol-2-yl}-1-benzyl-1H-pyrrole-2-carboxamide I-56 EV-AW5302-001 (EOAI3455898) was synthesised from a byproduct of the synthetic route to I-55 (Scheme 1.12)

I-57

(3R)-1-[7-Methoxy-1-methyl-2-(1-phenyl-1H-pyrrol-2-yl)-1H-1,3-benzodiazole-5-carbonyl]piperidin-3-amine I-57 EV-AW1377-001 (EOAI3456183) was synthesised according to the procedures described in Scheme 1 via synthesis of methyl 1-phenyl-1H-pyrrole-2-carboxylate (EV-AW1367-001) as described in Scheme 1.13.

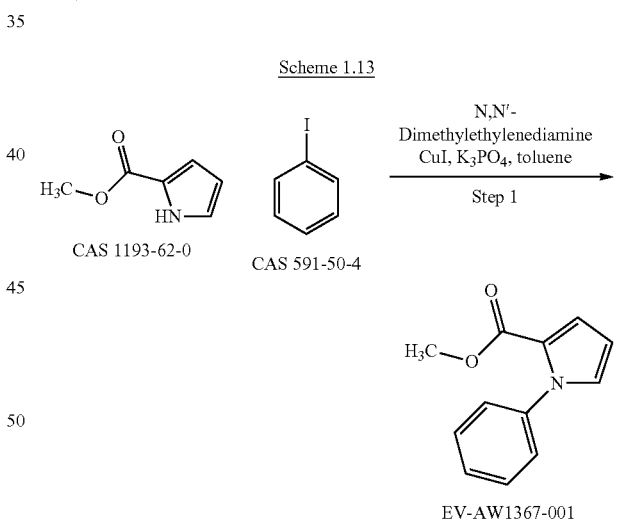

Methyl 1-phenyl-1H-pyrrole-2-carboxylate (EV-AW1367-001)—Step 1

Methyl 1H-pyrrole-2-carboxylate (CAS 1193-62-0, 100 mg, 0.80 mmol) and iodobenzene (CAS591-50-4, 107 µl, 0.96 mmol) were dissolved in toluene (2 ml) and N,N'-dimethyl ethane-1,2-di amine (35 µl, 0.32 mmol) and potassium phosphate (356 mg, 1.68 mmol) were added. The reaction was purged with nitrogen for 5 minutes then copper (I) iodide (30 mg, 0.16 mmol) was added. The mixture was stirred at 110° C. for 17 h. The reaction was allowed to cool to room temperature, diluted with ethyl acetate (20 ml) and washed with water (5×10 ml). The organic layer was dried over sodium sulfate and concentrated in vacuo. The crude material was purified by flash column chromatography (0-100% ethyl acetate/heptane) to obtain 127 mg (79%) of methyl 1-phenyl-H-pyrrole-2-carboxylate (EV-AW1367-001) as a white powder. LCMS (method D): retention time 1.15 min, M/z=202 (M+1).

I-13

(3R)-1-{2-[1-(Cyclopropylmethyl)-5-phenyl-1H-imidazol-2-yl]-1-methyl-1H-1,3-benzodiazole-5-carbonyl}piperidin-3-amine I-13 EV-AS5448-002 (EOAI3435745) was synthesised according to the procedures described in Scheme 1 via synthesis of ethyl 1-(cyclopropylmethyl)-5-phenyl-1H-imidazole-2-carboxylate (EV-AS5437-001) as described in Scheme 1.14.

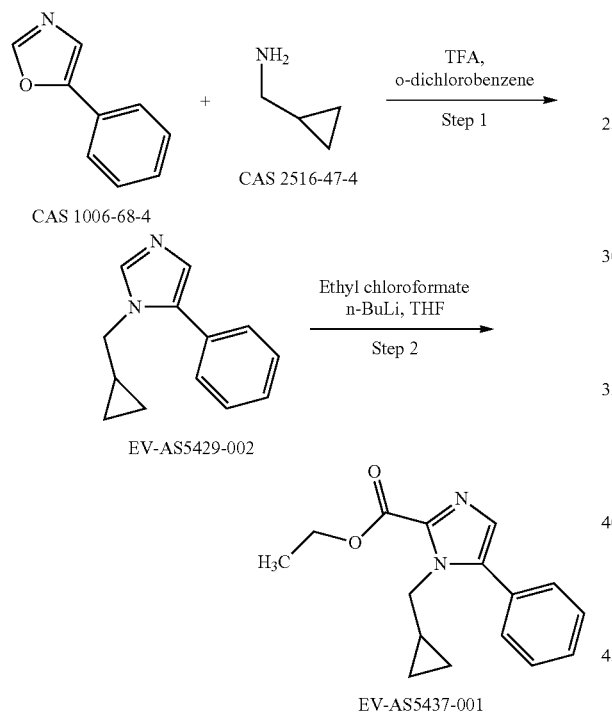

Scheme 1.14

1-(Cyclopropylmethyl)-5-phenyl-1H-imidazole (EV-AS5429-002)—Step 1

To a solution of 5-phenyl-1,3-oxazole (CAS 1006-68-4, 1.00 g, 6.90 mmol) and cyclopropyl-methylamine (CAS 2516-47-4, 980 mg, 13.8 mmol) in o-dichlorobenzene (10 ml) was added trifluoroacetic acid (1.054 ml, 13.78 mmol). The reaction was stirred at 200° C. under microwave irradiation for 1.5 h. The mixture was poured into a mixture of 1M aqueous sodium hydroxide (20 ml) and saturated aqueous sodium chloride (40 ml) and extracted with ethyl acetate (3×20 ml). The combined organic extracts were dried over sodium sulfate and concentrated in vacuo. The crude material was purified with an SCX-II cartridge. The cartridge was washed sequentially with MeOH then with 2M ammonia in MeOH. The ammonia/MeOH washings were concentrated in vacuo to obtain 250 mg of 1-(cyclopropylmethyl)-5-phenyl-1H-imidazole (EV-AS5429-002) as a brown solid. LCMS (method D): retention time 0.71 min, M/z=199 (M+1).

Ethyl 1-(cyclopropylmethyl)-5-phenyl-1H-imidazole-2-carboxylate (EV-AS5437-001)—Step 2

To a solution of 1-(cyclopropylmethyl)-5-phenyl-1H-imidazole (EV-AS5429-002, 50 mg, 0.25 mmol) in anhydrous THF (5 ml) at −60° C. under nitrogen was added a 2.5M solution of n-BuLi in hexane (119 µl, 0.30 mmol). After stirring for 30 minutes, ethylchloroformate (47 µl, 0.50 mmol) was added. The mixture was stirred at room temperature for 16 h, quenched by addition of water (10 ml) and then extracted with ethyl acetate (2×20 ml). The combined organic extracts were dried over sodium sulfate and concentrated in vacuo to obtain 66 mg (85%) of ethyl 1-(cyclopropylmethyl)-5-phenyl-1H-imidazole-2-carboxylate (EV-AS5437-001) as a yellow oil. LCMS (method D): retention time 1.17 min, M/z=271 (M+1).

I-62

5-{5-[(3R)-3-Aminopiperidine-1-carbonyl]-7-methoxy-1-methyl-1H-1,3-benzodiazol-2-yl}-1-(cyclopropylmethyl)-1H-pyrrole-2-carbonitrile, I-62, EV-AW1394-001 (EOAI3458420) was synthesised according to procedures described in Scheme 1 via synthesis of methyl 7-cyano-2-{1-ethyl-1H-pyrrolo[2,3-b]pyridin-2-yl}-1-methyl-1H-1,3-benzodiazole-5-carboxylate (EV-AW1386-001) as described in Scheme 1.15.

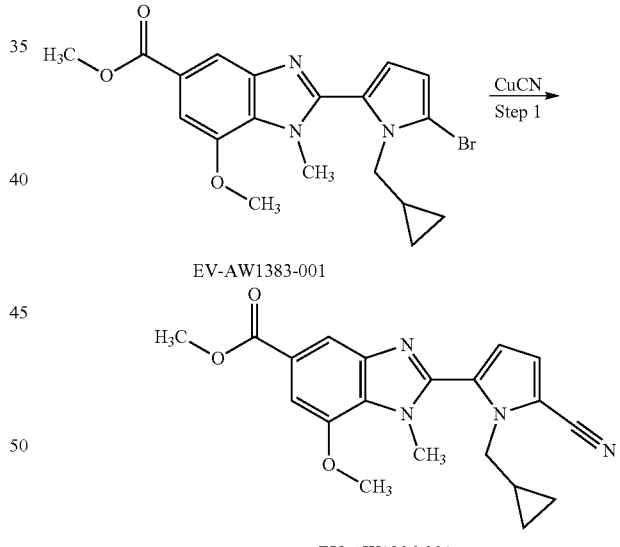

Scheme 1.15

Methyl 7-cyano-2-{1-ethyl-1H-pyrrolo[2,3-b]pyridin-2-yl}-1-methyl-1H-1,3-benzodiazole-5-carboxylate (EV-AW1386-001)—Step 1

Copper(I) cyanide (31 mg, 0.35 mmol) was added to a stirred solution of methyl 2-[5-bromo-1-(cyclopropylmethyl)-1H-pyrrol-2-yl]-7-methoxy-1-methyl-1H-1,3-benzodiazole-5-carboxylate (EV-AW1383-001 synthesised according to Scheme 1, step 1-5, 90%, 162 mg, 0.35 mmol) in NMP (3 ml). The reaction mixture was stirred at 16° C.

for 17 h, cooled down to room temperature and further copper(I) cyanide (16 mg, 0.17 mmol) was added. The reaction was stirred at for 5 h. The reaction mixture was cooled to 0° C. and water (30 ml) was added followed by ethyl acetate (30 ml). The organic phase was isolated and the aqueous extracted with ethyl acetate (2×10 ml). The combined organics were dried over sodium sulfate and concentrated in vacuo. The crude material was purified by flash column chromatography (0-100% ethyl acetate/heptane) to obtain 88 mg (49%) of ethyl 7-cyano-2-{1-ethyl-H-pyrrolo[2,3-b]pyridin-2-yl}-1-methyl-1H-1,3-benzodiazole-5-carboxylate (EV-AW1386-001) as a white powder. LCMS (method D): retention time 1.25 min, M/z=365 (M+1).

I-71

(1R,4R,7R)-2-{2-[1-(Cyclopropylmethyl)-2-(1-methyl-1H-pyrazol-4-yl)-1H-imidazol-5-yl]-7-methoxy-1-methyl-1H-1,3-benzodiazole-5-carbonyl}-2-azabicyclo[2.2.1]heptan-7-amine, I-71, EV-AW6285-001 (EOAI3461374) was synthesised according to the procedures described in Scheme 1 via synthesis of 1-(cyclopropylmethyl)-2-(1-methyl-1H-pyrazol-4-yl)-1H-imidazole-5-carboxylic acid (EV-AW6268-002) as described in Scheme 1.16.

Methyl 2-[N-(cyclopropylmethyl)-1-(1-methyl-1H-pyrazol-4-yl)formamido]acetate EV-AW6260-002—Step 2

Triethylamine (2.98 ml, 21.4 mmol) was added dropwise to a stirred solution of methyl 2-[(cyclopropylmethyl)amino]acetate (EV-AW6256-001, 2.00 g, 10.2 mmol) in dry THF (80 ml) at 0° C. under an atmosphere of nitrogen and stirring was continued for 5 minutes. 1-Methyl-1H-pyrazole-4-carbonyl chloride (CAS 79583-19-0, 1.62 g, 11.2 mmol) was added portionwise to the reaction mixture at 0° C. and stirring was continued for 1 h at this temperature. The reaction was quenched with water (80 ml) and the mixture was concentrated under reduced pressure. The resulting aqueous residue was extracted with ethyl acetate (2×80 ml). The combined organic layers were washed with saturated aqueous sodium chloride, dried over sodium sulfate, filtered and concentrated under reduced pressure. The residue was purified by column chromatography (0-5% methanol/DCM) to obtain 1.82 g (65%) of methyl 2-[N-(cyclopropylmethyl)-1-(1-methyl-1H-pyrazol-4-yl)formamido]acetate (EV-AW6260-002) as a pale yellow oil. LCMS (method D): retention time 0.86 min, M/z=252 (M+1).

Scheme 1.16

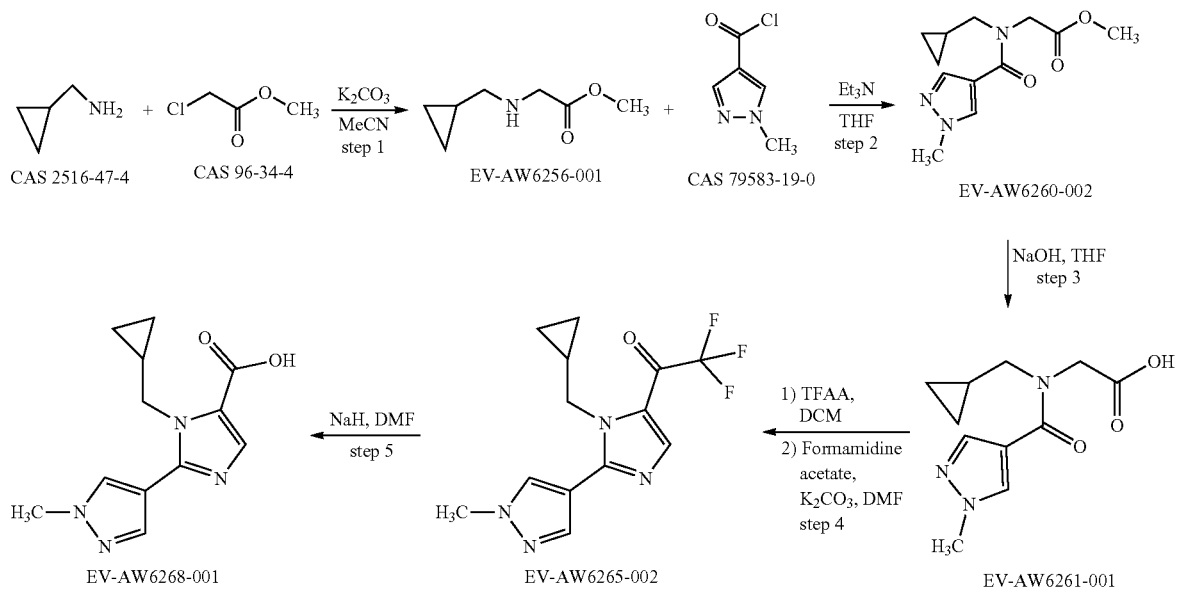

Methyl 2-[(cyclopropylmethyl)amino]acetate EV-AW6256-001—Step 1

To a stirred solution of cyclopropylmethanamine (CAS 2516-47-4, 4.00 g, 56.2 mmol) in acetonitrile (40 ml), was added potassium carbonate (7.77 g, 56.2 mmol) followed by methyl 2-chloroacetate (CAS 96-34-4, 4.93 ml, 56.2 mmol) in acetonitrile (20 ml) dropwise. The mixture was left stirring for 17 h at room temperature. The reaction mixture was filtered and the solid was washed with further acetonitrile (60 ml), the filtrate was concentrated in vacuo to yield 8.07 g (82%) of methyl 2-[(cyclopropylmethyl)amino]acetate (EV-AW6256-001) as a pale yellow solid. LCMS (method D): retention time solvent front, M/z=143.9 (M+1).

Sodium 2-[N-(cyclopropylmethyl)-1-(1-methyl-1H-pyrazol-4-yl)formamido]acetate EV-AW6261-001—Step 3

To methyl 2-[N-(cyclopropylmethyl)-1-(1-methyl-1H-pyrazol-4-yl)formamido]acetate (EV-AW6260-002 and EV-AW6257-003 obtained as EV-AW6260-002, 2.23 g, 8.25 mmol) in THF (15 ml) was added 2M sodium hydroxide (10.3 ml). The reaction mixture was heated at 50° C. with stirring for 2.5 h. The mixture was concentrated to dryness to obtain 3.00 g (98%) of sodium 2-[N-(cyclopropylmethyl)-1-(1-methyl-1H-pyrazol-4-yl)formamido]acetate (EV-AW6261-001). LCMS (method D): retention time 0.79 min, M/z=238 (M+1).

1-[1-(Cyclopropylmethyl)-2-(1-methyl-1H-pyrazol-4-yl)-1H-imidazol-5-yl]-2,2,2-trifluoroethan-1-one EV-AW6265-002—Step 4

To a stirred solution of sodium 2-[N-(cyclopropylmethyl)-1-(1-methyl-1H-pyrazol-4-yl)formamido]acetate (EV-AW6261-001, 2.74 g, 7.40 mmol) in DCM (30 ml) was added trifluoroacetic anhydride (4.12 ml, 29.6 mmol) at 0° C. and the mixture was stirred at room temperature for 2 h. Further trifluoroacetic anhydride (4.12 ml, 29.6 mmol) at 0° C. and stirring at room temperature was continued for 17 h. The solvent was removed in vacuo and the residue was dissolved in DMF (50 ml), the mixture was cooled to 0° C. and methanimidamide acetic acid (2.31 g, 22.2 mmol) and potassium carbonate (3.07 g, 22.2 mmol) were added. The mixture was heated at 70° C. for 3 h, diluted with water (30 ml) and extracted with ethyl acetate (2×30 ml). The combined organic extracts were dried over sodium sulfate, filtered and concentrated in vacuo. The residue was purified by column chromatography (0-75% ethyl acetate/heptane) to obtain 1.32 g (60%) of 1-[1-(cyclopropylmethyl)-2-(1-methyl-H-pyrazol-4-yl)-1H-imidazol-5-yl]-2,2,2-trifluoroethan-1-one (EV-AW6265-002) as an off-white solid. LCMS (method D): retention time 1.18 min, M/z=299 (M+1).

1-(Cyclopropylmethyl)-2-(1-methyl-1H-pyrazol-4-yl)-1H-imidazol-5-carboxylic acid EV-AW6268-002—Step 5

To a solution of 1-[1-(cyclopropylmethyl)-2-(1-methyl-1H-pyrazol-4-yl)-1H-imidazol-5-yl]-2,2,2-trifluoroethan-1-one (EV-AW6265-002, 1.31 g, 4.08 mmol) in DMF (20 ml) under an atmosphere of nitrogen was added portionwise NaH (60%, 0.65 g, 16.3 mmol) with ice-water cooling. The reaction mixture was heated at 70° C. and stirred at this temperature for 3 h. The solvent was removed in vacuo and the residue was dissolved in water (60 ml) and acidified to pH 4 with 1M HCl. The aqueous layer was extracted with a solution of 1:4 2-propanol:chloroform (2×60 ml). The combined organic layers were dried over sodium sulfate, filtered and concentrated under reduced pressure. The crude product and the concentrated aqueous layer were purified by reverse phase chromatography (5-30% acetonitrile/water with 0.1% formic acid additive) to obtain 0.90 g (89%) of 1-(cyclopropylmethyl)-2-(1-methyl-H-pyrazol-4-yl)-1H-imidazole-5-carboxylic acid (EV-AW6268-002) as a creamy coloured solid. LCMS (method D): retention time 0.74 min, M/z=247 (M+1).

I-109
(1R,4R,7R)-2-[2-(2-Cyclobutyl-1-ethyl-1H-imidazol-5-yl)-7-methoxy-1-methyl-1H-1,3-benzodiazole-5-carbonyl]-2-azabicyclo[2.2.1]heptan-7-amine, 1-109, EV-AY4676-001 (EOAI3482311) was synthesised according to the procedures described in Scheme 1 via synthesis of methyl 2-cyclobutyl-1-ethyl-H-imidazole-5-carboxylate (EV-AY4663-002) as described in Scheme 1.17.

Scheme 1.17

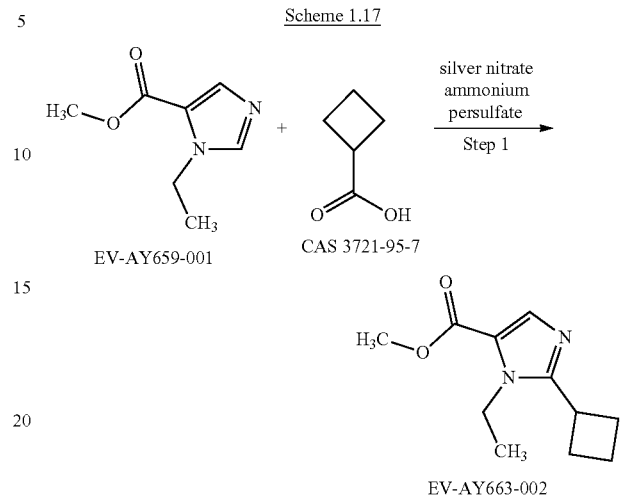

Methyl 2-cyclobutyl-1-ethyl-1H-imidazole-5-carboxylate (EV-AY4663-002)—Step 1

To a suspension of silver(1+) nitrate (161 mg, 0.95 mmol) and cyclobutanecarboxylic acid (CAS 3721-95-7, 473 mg, 4.73 mmol) in 10% aqueous $H_2SO_4$ (15 ml) was added methyl 1-ethyl-1H-imidazole-5-carboxylate (EV-AY4659-001, 243 mg, 1.58 mmol) and the reaction mixture was heated at 70° C. A 0.2M aqueous solution of ammonium persulfate (23.6 ml) was added in small portions during a period of 10 minutes. The reaction mixture was cooled down to room temperature and was stirred for 10 minutes, poured into ice and basified using aqueous ammonia ca. 33%, then extracted with ethyl acetate (2×20 ml). The combined extracts were washed with saturated aqueous sodium chloride (2×20 ml), dried over magnesium sulfate and concentrated in vacuo. The crude material was purified by flash column chromatography (5-50% ethyl acetate/heptane) to obtain 72 mg (22%) of methyl 2-cyclobutyl-1-ethyl-1H-imidazole-5-carboxylate (EV-AY4663-002) as a pale oil. LCMS (method D): retention time 0.82 min, M/z=209 (M+1).

I-112
6-{5-[(1R,4R,7R)-7-Amino-2-azabicyclo[2.2.1] heptane-2-carbonyl]-7-methoxy-1-methyl-1H-1,3-benzodiazol-2-yl}-1-(cyclopropylmethyl)-3-methyl-1,2-dihydropyridin-2-one, 112, EV-AY2080-001 (EOAI3655173) was synthesised according to the procedures described in Scheme 1 and Scheme 1.18.

Scheme 1.18

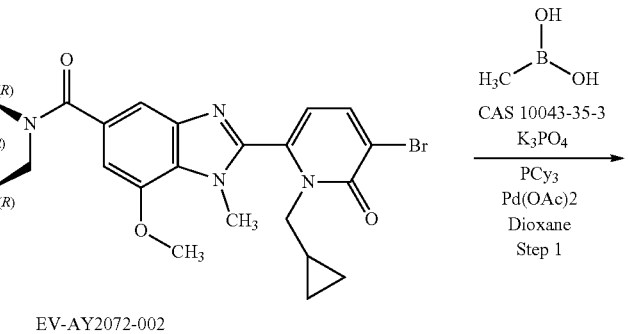

EV-AY2072-002

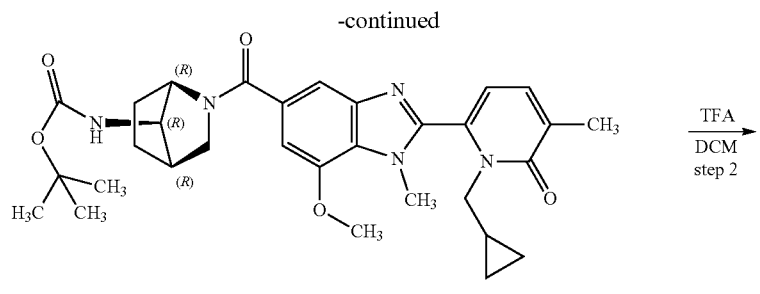

EV-AY2075-002

EV-AY2080-001

Tert-butyl N-[(1R,4R,7R)-3-[2-[1-(cyclopropylmethyl)-5-methyl-6-oxo-2-pyridyl]-7-methoxy-1-methyl-benzimidazole-5-carbonyl]-3-azabicyclo[2.2.1]heptan-7-yl]carbamate (EV-AY2075-002) Step 1

To a solution of tert-butyl N-[(1R,4R,7R)-3-[2-[5-bromo-1-(cyclopropylmethyl)-6-oxo-2-pyridyl]-7-methoxy-1-methyl-benzimidazole-5-carbonyl]-3-azabicyclo[2.2.1]heptan-7-yl]carbamate (EV-AY2072-002 synthesised according to Scheme 1, 142 mg, 0.12 mmol) in dioxane (1.5 ml) and water (0.15 ml) was added methylboronic acid (CAS 10043-35-3, 14 mg, 0.23 mmol), tripotassium phosphate (19 μl, 0.23 mmol) and tricyclohexylphosphane (7 μl, 0.02 mmol). The reaction mixture was purged with nitrogen for 5 minutes and palladium(2+) diacetate (3 mg, 0.01 mmol) was added in one portion. The reaction vessel was sealed and heated to 120° C. for 16 h. The mixture was diluted with water (5 ml), extracted with DCM (2×15 ml). The combined organics were concentrated and purified by column chromatography (0-10% methanol/ethyl acetate) to obtain 37 mg (46%) of tert-butyl N-[(1R,4R,7R)-3-[2-[1-(cyclopropylmethyl)-5-methyl-6-oxo-2-pyridyl]-7-methoxy-1-methyl-benzimidazole-5-carbonyl]-3-azabicyclo[2.2.1]heptan-7-yl]carbamate (EV-AY2075-002) as a yellow oil. LCMS (method D): retention time 1.15 min, M/z=562 (M+1).

Tert-butyl N-[(1R,4R,7R)-3-[2-[1-(cyclopropylmethyl)-5-methyl-6-oxo-2-pyridyl]-7-methoxy-1-methyl-benzimidazole-5-carbonyl]-3-azabicyclo[2.2.1]heptan-7-yl]carbamate (EV-AY2080-001)— Step 2

Tert-butyl N-[(1R,4R,7R)-3-[2-[1-(cyclopropylmethyl)-5-methyl-6-oxo-2-pyridyl]-7-methoxy-1-methyl-benzimidazole-5-carbonyl]-3-azabicyclo[2.2.1]heptan-7-yl]carbamate (EV-AY2075-002, 37 mg, 0.07 mmol) was dissolved in DCM (ml) and treated with trifluoroacetic acid (0.22 ml, 2.83 mmol) under an atmosphere of nitrogen and stirred at room temperature for 1 h. The mixture was concentrated in vacuo and azeotroped with toluene/acetonitrile. The residue was purified by prep HPLC (basic method), treated with Smopex-105 (5 mg) for 1 hour and freeze dried to obtain 0.016 g (49%) of 6-[5-[(1R,4R,7R)-7-amino-3-azabicyclo[2.2.1]heptane-3-carbonyl]-7-methoxy-1-methyl-benzimidazol-2-yl]-1-(cyclopropylmethyl)-3-methyl-pyridin-2-one I-112 (EV-AY2080-001) as a white powder. LCMS (method H): retention time 2.28 min, M/z=462 (M+1).

I-118

(1R,4R,7R)-2-[2-(3-Ethylpyridin-4-yl)-7-methoxy-1-methyl-1H-1,3-benzodiazole-5-carbonyl]-2-azabicyclo[2.2.1]heptan-7-amine, I-118, EV-BA1121-001 (EOAI3694084) was synthesised according to the procedures described in Scheme 1 via synthesis of methyl 3-ethylpyridine-4-carboxylate (EV-BA1108-001) as described in Scheme 1.19.

Scheme 1.19

Methyl 3-ethenylpyridine-4-carboxylate (EV-BA1103-002)—Step 1

A suspension of methyl 3-bromopyridine-4-carboxylate (CAS 59786-31-1, 0.50 g, 2.31 mmol), caesium fluoride (1.05 g, 6.94 mmol) and 2,4,6-etenylboroxin-pyridine complex (CAS 95010-17-6, 1.39 g, 5.79 mmol) in THF (20 ml) was purged with nitrogen for 5 minutes. Pd(dppf)Cl$_2$ (0.34 g, 0.46 mmol) was added and the reaction mixture was heated at 70° C. for 2 h. The mixture was cooled down to room temperature and filtered through Celite washing the solid with ethyl acetate. The filtrate was washed with saturated aqueous sodium chloride, dried over magnesium sulfate, filtered and concentrated in vacuo. The residue was purified by column chromatography (12-100% ethyl acetate/heptane) to obtain 0.37 g (97%) of methyl 3-ethenylpyridine-4-carboxylate (EV-BA1103-002). LCMS (method D): retention time 0.88 min, M/z=137 (M+1).

Methyl 3-ethenylpyridine-4-carboxylate (EV-BA1108-001)—Step 2

A suspension of methyl 3-ethenylpyridine-4-carboxylate (EV-BA1103-002, 100 mg, 0.61 mmol) and Pd/C (10%, 33 mg, 0.03 mmol) in ethanol (2 ml) was stirred at room temperature under an atmosphere of hydrogen for 16 h. The reaction mixture was filtered through Celite and the filtrate was concentrated to obtain 140 mg (55%) of methyl 3-ethylpyridine-4-carboxylate (EV-BA1108-001). LCMS (method D): retention time 0.85 min, M/z=166 (M+1).

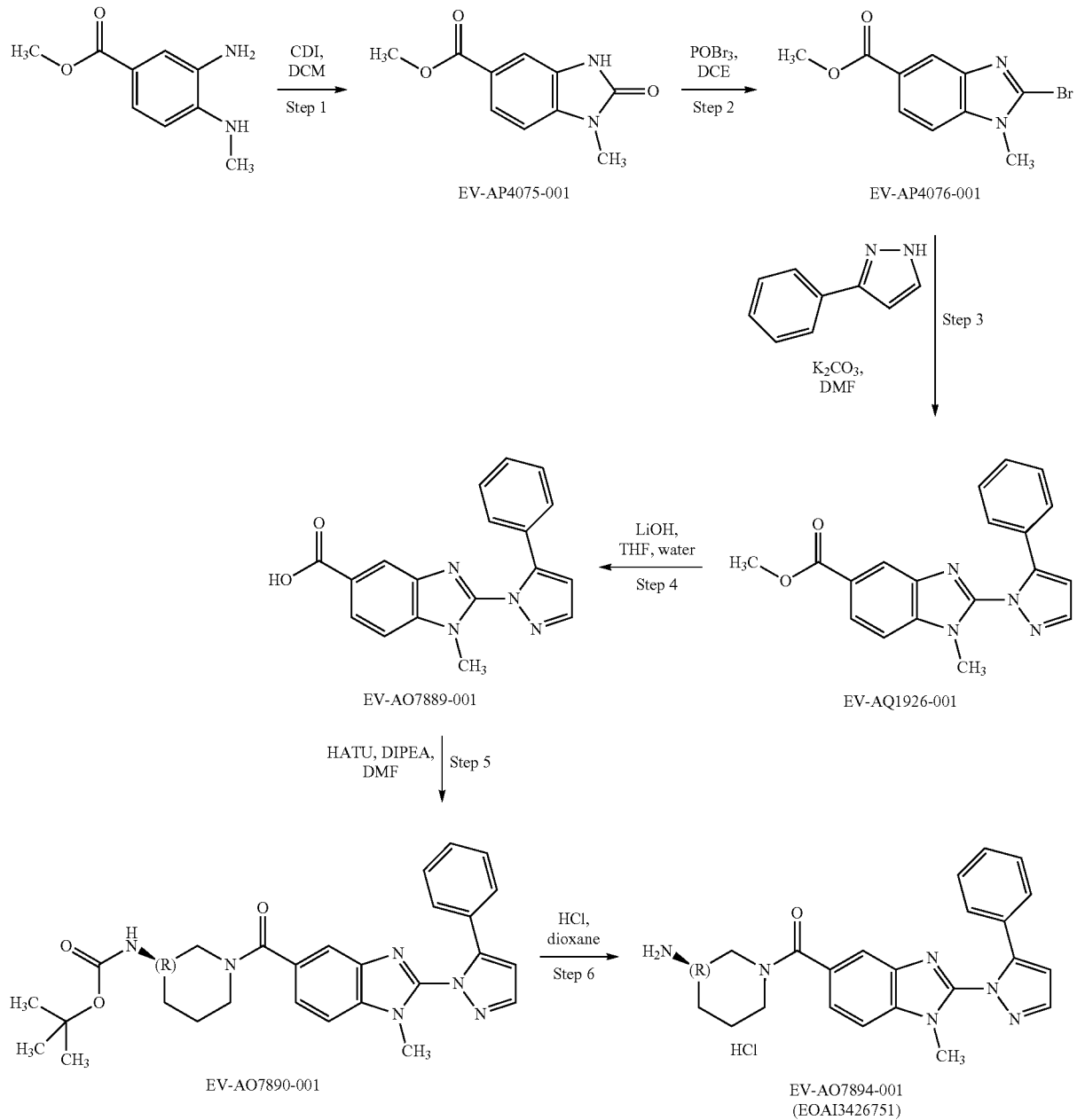

Scheme 2

Synthesis of (3R)-1-[1-methyl-2-(5-phenyl-1H-pyrazol-1-yl)-1H-1,3-benzodiazole-5-carbonyl]piperidin-3-amine hydrochloride, I-59, EOAI3426751 (EV-AO7894-001)

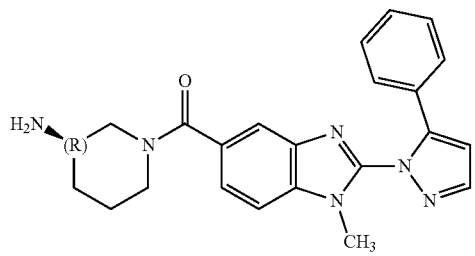

Methyl 1-methyl-2-oxo-2,3-dihydro-1H-1,3-benzodiazole-5-carboxylate (EV-AP4075-001)—Step 1

To a solution of methyl 3-amino-4-(methylamino)benzoate (EV-AN2487-001, synthesised as described in Scheme 1, 100 mg, 0.54 mmol) in anhydrous DCM (3 ml) was added 1,1'-carbonyldiimidazole (110 mg, 0.68 mmol). The mixture was stirred at room temperature for 16 h. The precipitate was collected by vacuum filtration and washed with ice-cold diethyl ether (2×2 ml). The solid was air dried for 2 h to obtain 82 mg (73%) of methyl 1-methyl-2-oxo-2,3-dihydro-1H-1,3-benzodiazole-5-carboxylate (EV-AP4075-001) as a white powder. LCMS (method D): retention time 0.94 min, M/z=207 (M+1).

Methyl 2-bromo-1-methyl-1H-1,3-benzodiazole-5-carboxylate (EV-AP4076-001)—Step 2

To a solution of phosphorus oxybromide (217 mg, 0.76 mmol) in dichloroethane (3 ml) in a pressure tube was added methyl 1-methyl-2-oxo-2,3-dihydro-1H-1,3-benzodiazole-5-carboxylate (EV-AP4075-001, 78 mg, 0.38 mmol). The vessel was sealed and the mixture was stirred at 80° C. for 16 h. The mixture was allowed to cool to room temperature and phosphorus oxybromide (217 mg, 0.76 mmol) was added. The mixture was heated at 80° C. for 5 h then at room temperature for 62 h. Phosphorus oxybromide (434 mg, 1.52 mmol) was added and the reaction heated at 80° C. for 20 h. The reaction was allowed to cool to room temperature and neutralised with water (10 ml) and 2M aqueous sodium carbonate (10 ml). The aqueous mixture was extracted with DCM (3×8 ml) and the combined organic extracts were washed with water (3×5 ml), saturated aqueous sodium chloride (10 ml), dried over magnesium sulfate and concentrated in vacuo to obtain 72 mg (68%) of methyl 2-bromo-1-methyl-1H-1,3-benzodiazole-5-carboxylate (EV-AP4076-001) as a white powder. LCMS (method D): retention time 1.09 min, M/z=269/271 (M+1).

Methyl 1-methyl-2-(5-phenyl-1H-pyrazol-1-yl)-1H-1,3-benzodiazole-5-carboxylate (EV-AQ1926-001)—Step 3

To a solution of methyl 2-bromo-1-methyl-H-1,3-benzodiazole-5-carboxylate (EV-AP4096-001, 57 mg, 0.20 mmol) in DMF (1 ml) in a pressure tube was added potassium carbonate (56.2 mg, 0.41 mmol) followed by 3-phenyl-1H-pyrazole (CAS 2458-26-6, 44.0 mg, 0.31 mmol). The vessel was sealed and the reaction mixture was stirred at 120° C. for 3 h. The mixture was allowed to cool to room temperature and partitioned between ethyl acetate (5 ml) and water (5 ml). The aqueous layer was extracted with ethyl acetate (5 ml) then the combined organic extracts were evaporated to dryness and azeotroped with heptane. The crude material was purified by flash column chromatography (0-60% ethyl acetate/heptane) to obtain 24 mg (35%) of methyl 1-methyl-2-(5-phenyl-1H-pyrazol-1-yl)-1H-1,3-benzodiazole-5-carboxylate (EV-AQ1926-001) as a white solid. LCMS (method D): retention time 1.48 min, M/z=333 (M+1).

1-Methyl-2-(5-phenyl-1H-pyrazol-1-yl)-1H-1,3-benzodiazole-5-carboxylic acid (EV-AO7889-001)—Step 4

To a solution of methyl 1-methyl-2-(5-phenyl-1H-pyrazol-1-yl)-1H-1,3-benzodiazole-5-carboxylate (EV-AQ1926-001, 24 mg, 0.07 mmol) in THF/water (1:1, 4 ml) was added lithium hydroxide (6.0 mg, 0.25 mmol). The resulting mixture was stirred at 50° C. for 2 h. The solvent was removed in vacuo to obtain 23 mg (assumed quantitive) of 1-methyl-2-(5-phenyl-1H-pyrazol-1-yl)-1H-1,3-benzodiazole-5-carboxylic acid (EV-AO7889-001) as a white solid. LCMS (method D): retention time 1.31 min, M/z=319 (M+1).

Tert-butyl N-[(3R)-1-[1-methyl-2-(5-phenyl-1H-pyrazol-1-yl)-1H-1,3-benzodiazole-5-carbonyl]piperidin-3-yl]carbamate (EV-AO7890-001)—Step 5

To a solution of 1-methyl-2-(5-phenyl-1H-pyrazol-1-yl)-1H-1,3-benzodiazole-5-carboxylic acid (EV-AO7889-001, 22 mg, 0.07 mmol) and DIPEA (14 µl, 0.08 mmol) in anhydrous DMF (3 ml) was added HATU (31 mg, 0.08 mmol). The reaction was stirred at room temperature for 10 minutes, tert-butyl (3R)-piperidin-3-ylcarbamate (14 mg, 0.07 mmol) was added and the reaction was continued for 60 h. Further HATU (31 mg, 0.08 mmol), DIPEA (14 µl, 0.08 mmol) and tert-butyl (3R)-piperidin-3-ylcarbamate (14 mg, 0.07 mmol) were added. The reaction was stirred at 60° C. for 2.5 h. The mixture was concentrated in vacuo and the residue was purified by acidic HPLC preparative method to obtain 16 mg (47%) of tert-butyl N-[(3R)-1-[1-methyl-2-(5-phenyl-1H-pyrazol-1-yl)-1H-1,3-benzodiazole-5-carbonyl]piperidin-3-yl]carbamate (EV-A07890-001) as a white powder.

(3R)-1-[1-Methyl-2-(5-phenyl-1H-pyrazol-1-yl)-1H-1,3-benzodiazole-5-carbonyl]piperidin-3-amine hydrochloride, I-59, (EV-A07894-001) Step 6

4M HCl in dioxane (2 ml) was added to a solution of tert-butyl N-[(3R)-1-[1-methyl-2-(5-phenyl-1H-pyrazol-1-yl)-1H-1,3-benzodiazole-5-carbonyl]piperidin-3-yl]carbamate (EV-AO7890-001, 16 mg, 0.03 mmol) in dioxane (2 ml) at room temperature. The mixture was stirred at room temperature for 2 h. The solvent was removed in vacuo and the residue was freeze dried from acetonitrile:water (1:1, 2 ml) to obtain 14 mg (99%) of (3R)-1-[1-methyl-2-(5-phenyl-1H-pyrazol-1-yl)-1H-1,3-benzodiazole-5-carbonyl]piperidin-3-amine hydrochloride, 1-59, (EV-AO7894-001) as a colourless crystalline solid. LCMS (method A): retention time 2.04 min, M/z =401.2 (M+1).

Scheme 3

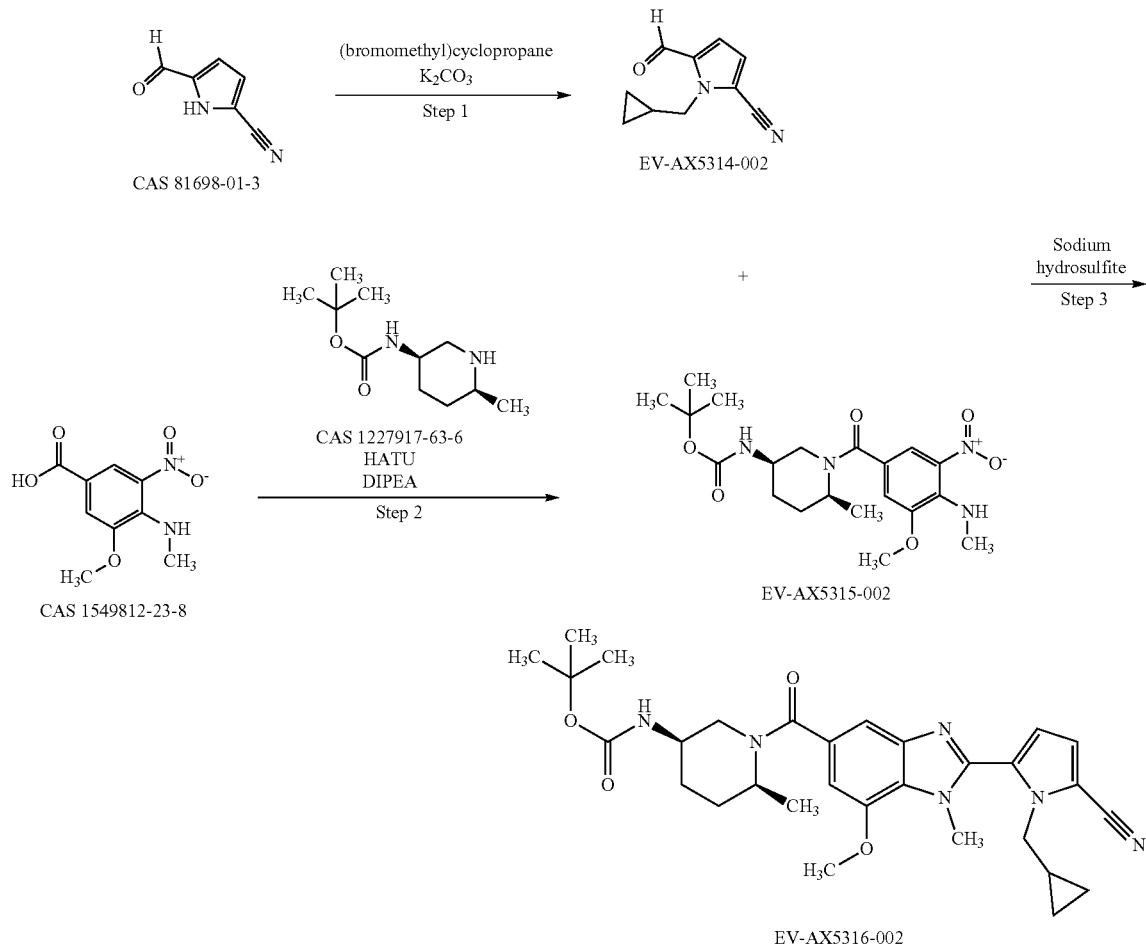

1-(Cyclopropylmethyl)-5-formyl-1H-pyrrole-2-carbonitrile (EV-AX5314-002)—Step 1

To a solution of 5-formyl-1H-pyrrole-2-carbonitrile (CAS 81698-01-3, 749 mg, 6.24 mmol) in acetonitrile (25 ml) was added potassium carbonate (2.15 g, 15.6 mmol) followed by (bromomethyl)cyclopropane (1.51 ml, 15.6 mind). The mixture was stirred at 50° C. for 17 h. The reaction mixture was cooled down to room temperature, poured onto water (75 ml) and extracted with ethyl acetate (3×75 ml). The combined organic layers were washed with water (100 ml) and saturated aqueous sodium chloride (100 ml), dried over sodium sulfate and concentrated in vacuo. The crude product was purified by flash column chromatography (0-20% ethyl acetate/heptane) to obtain 898 mg (79%) of 1-(cyclopropylmethyl)-5-formyl-1H-pyrrole-2-carbonitrile as a white solid (EV-AX5314-002) as a white solid. LCMS (method D): retention time 1.08 min, M/z=175 (M+1).

Tert-butyl N-[(3R,6S)-1-[3-methoxy-4-(methylamino)-5-nitrobenzoyl]-6-methylpiperidin-3-yl]carbamate (EV-AX5315-002)—Step 2

To a solution of 3-methoxy-4-(methylamino)-5-nitrobenzoic acid (CAS 1549812-23-8, 264 mg, 1.17 mmol) and HATU (440 mg, 1.17 mmol) in dry DMF (5 ml) was added DIPEA (0.41 ml, 2.33 mmol) and the mixture was stirred at room temperature for 30 minutes. Tert-butyl N-[(3R,6S)-6-methylpiperidin-3-yl]carbamate (CAS 1227917-63-6, 250 mg, 1.17 mmol) was added and the reaction stirred for 17 h. The reaction mixture was concentrated in vacuo and partitioned between ethyl acetate (50 ml) and saturated aqueous sodium chloride (50 ml). The aqueous layer was extracted with ethyl acetate (30 ml) and the combined organics were washed with water (40 ml), dried over sodium sulfate and concentrated in vacuo. The crude material was purified by flash column chromatography (0-100% ethyl acetate/heptane) to obtain 421 mg (85%) of tert-butyl N-[(3R,6S)-1-[3-methoxy-4-(methylamino)-5-nitrobenzoyl]-6-methylpiperidin-3-yl]carbamate (EV-AX5315-002) as an orange foam. LCMS (method D): retention time 1.18 min, M/z=423 (M+1).

Tert-butyl N-[(3R,6S)-1-{2-[5-cyano-1-(cyclopropylmethyl)-1H-pyrrol-2-yl]-7-methoxy-1-methyl-1H-1,3-benzodiazole-5-carbonyl}-6-methylpiperidin-3-yl]carbamate (EV-AX5316-002)—Step 3

To a mixture of tert-butyl N-[(3R,6S)-1-[3-methoxy-4-(methylamino)-5-nitrobenzoyl]-6-methylpiperidin-3-yl]carbamate (EV-AX5315-002, 150 mg, 0.36 mmol) and 1-(cyclopropylmethyl)-5-formyl-1H-pyrrole-2-carbonitrile (EV-AX5314-002, 64 mg, 0.37 mmol) in ethanol (4 ml) was added portionwise a solution of sodium hydrosulfite (CAS 7775-14-6, 185 mg, 1.07 mmol) in water (2 ml). The mixture was purged with nitrogen and heated at 90° C. for 17 h. The reaction mixture was cooled down to room temperature and concentrated in vacuo. DCM (30 ml) was added to the residue and the heterogeneous solution was dried over sodium sulfate. The solid was filtered off and the filtrate was concentrated in vacuo. The crude material was purified by preparative HPLC (acidic method) to obtain 143 mg (74%) of tert-butyl N-[(3R,6S)-1-{2-[5-cyano-1-(cyclopropylmethyl)-1H-pyrrol-2-yl]-7-methoxy-1-methyl-1H-1,3-benzodiazole-5-carbonyl}-6-methylpiperidin-3-yl]carbamate (EV-AX5316-002) as a white solid. LCMS (method D): retention time 1.28 min, M/z=547 (M+1).

EV-AX5316-002 was used to synthesise 5-{5-[(2S,5R)-5-amino-2-methylpiperidine-1-carbonyl]-7-methoxy-1-methyl-1H-1,3-benzodiazol-2-yl}-1-(cyclopropylmethyl)-1H-pyrrole-2-carbonitrile, I-69, EV-AX5318-001 (EOAI3460934) according to the procedures described in Scheme 1.

Special cases for Scheme 3
I-73
5-{5-[(1R,4R,7R)-7-Amino-2-azabicyclo[2.2.1]heptane-2-carbonyl]-7-methoxy-1-{[(1R,3S)-3-methoxy-3-methylcyclobutyl]methyl}-1H-1,3-benzodiazol-2-yl}-1-(cyclopropylmethyl)-1H-pyrrole-2-carbonitrile, I-73, EV-AX7827-001 (EOAI3461384) was synthesised according to the procedures described in Scheme 3 and Scheme 1 via synthesis of methyl 2-[5-cyano-1-(cyclopropylmethyl)-1H-pyrrol-2-yl]-7-methoxy-1-{[(1R,3S)-3-methoxy-3-methylcyclobutyl]methyl}-1H-1,3-benzodiazole-5-carboxylate (EV-AX7820-001) described in Scheme 3.1

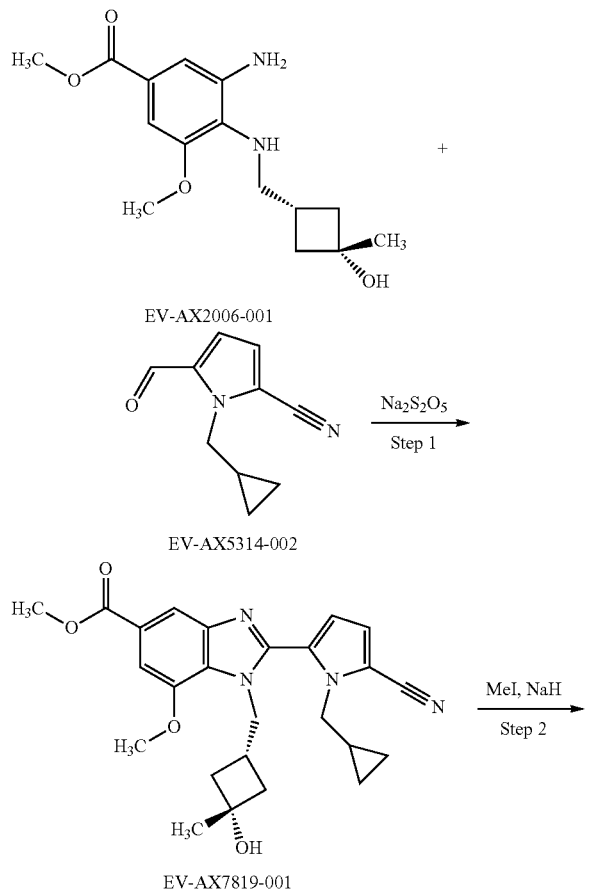

Methyl-2-[5-cyano-1-(cyclopropylmethyl)-1H-pyrrol-2-yl]-7-methoxy-1-{[(1R,3S)-3-hydroxy-3-methylcyclobutyl]methyl}-1H-1,3-benzodiazole-5-carboxylate (EV-AX7819-001)—Step 1

Methyl-3-amino-5-methoxy-4-({[(1R,3S)-3-hydroxy-3-methylcyclobutyl]methyl}amino)benzoate (EV-AX2006-001, 91%, 557 mg, 1.72 mmol) and 1-(cyclopropylmethyl)-5-formyl-1H-pyrrole-2-carbonitrile (EV-AX5314-002, 300 mg, 1.72 mmol) were dissolved in DMF (3 ml) and $Na_2S_2O_5$ (982 mg, 5.17 mmol) was added. The reaction mixture was stirred at 80° C. for 17 h and cooled down to room temperature. The mixture was diluted with ethyl acetate (20 ml), washed with water (3×10 ml) and saturated aqueous sodium chloride (5 ml). The combined organics were dried over sodium sulfate and concentrated in vacuo. The crude was purified by flash column chromatography (0-100% ethyl acetate/heptane) to obtain 574 mg (70%) of methyl-2-[5-cyano-1-(cyclopropylmethyl)-1H-pyrrol-2-yl]-7-methoxy-1-{[(1R,3S)-3-hydroxy-3-methylcyclobutyl]methyl}-1H-1,3-benzodiazole-5-carboxylate (EV-AX7819-001) as a yellow powder. LCMS (method D): retention time 1.19 min, M/z=449 (M+1).

Methyl-2-[5-cyano-1-(cyclopropylmethyl)-1H-pyrrol-2-yl]-7-methoxy-1-{[(1R,3S)-3-methoxy-3-methylcyclobutyl]methyl}-1H-1,3-benzodiazole-5-carboxylate (EV-AX7820-002)—Step 2

Methyl-2-[5-cyano-1-(cyclopropylmethyl)-1H-pyrrol-2-yl]-7-methoxy-1-{[(1R,3S)-3-hydroxy-3-methylcyclobutyl]methyl}-1H-1,3-benzodiazole-5-carboxylate (EV-AX7819-001, 574 mg, 1.20 mmol) was dissolved in DMF (7 ml) and NaH (60%, 96 mg, 2.41 mmol) was added. The reaction mixture was stirred at room temperature for 10 minutes then iodomethane (374 µl, 6.01 mmol) was added. The reaction was stirred at room temperature for 4 h then concentrated in vacuo. The residue was diluted with water (20 ml) and extracted into Ethyl acetate (3×30 ml). The combined organics were dried over sodium sulfate and the evaporated to dryness. The resulting material was purified by flash column chromatography (0-100% ethyl acetate/heptane) then by preparative HPLC (acidic method) to obtain 282 mg (50%) of methyl-2-[5-cyano-1-(cyclopropylmethyl)-1H-pyrrol-2-yl]-7-methoxy-1-{[(1R,3S)-3-methoxy-3-methylcyclobutyl]methyl}-1H-1,3-benzodiazole-5-carboxylate (EV-AX7820-002) as a white powder.

I-81

5-{5-[(1R,4R,7R)-7-Amino-2-azabicyclo[2.2.1]heptane-2-carbonyl]-7-methoxy-1-methyl-1H-1,3-benzodiazol-2-yl}-1-cyclopropyl-1H-pyrrole-2-carbonitrile, I-81, EV-AY4337-001 (EOA13468837) was synthesised according to procedures described in Scheme 3.1 via 1-cyclopropyl-5-formyl-1H-pyrrole-2-carbonitrile EV-AY4323-001 synthesised as described in Scheme 3.2.

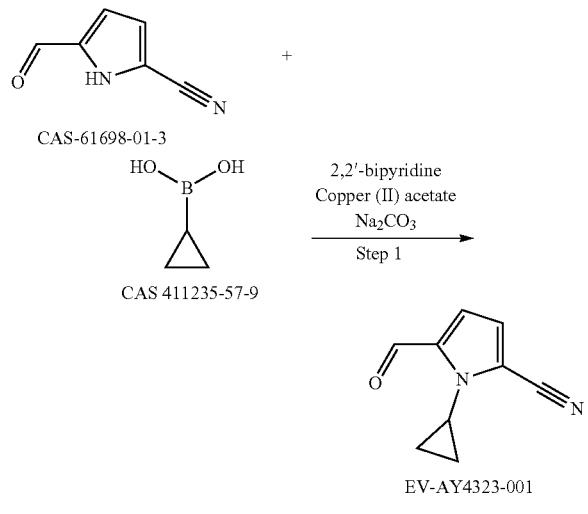

1-Cyclopropyl-5-formyl-1H-pyrrole-2-carbonitrile (EV-AY4323-001)—Step 1

To a solution of 5-formyl-1H-pyrrole-2-carbonitrile (CAS 81698-01-3, 250 mg, 1.98 mmol), cyclopropylboronic acid (CAS 411235-57-9, 510 mg, 5.93 mmol) and Na₂CO₃ (629 mg, 5.93 mmol) in DCE (1 ml) was added a suspension of copper(II) diacetate (539 mg, 2.97 mmol) and 2,2'-bipyridine (463 mg, 2.97 mmol) in DCE (2 ml). The reaction mixture was stirred at 70° C. for 4 h, cooled down to room temperature and quenched with 1M HCl (15 ml). The resulting material was extracted with ethyl acetate (3×10 ml). The combined organic fractions were washed with 5N NaOH (10 ml), saturated aqueous sodium chloride (10 ml), dried over sodium sulphate and concentrated in vacuo. The crude was purified by flash column chromatography (eluting with 0-50% ethyl acetate/heptane) to obtain 120 mg (38%) of 1-cyclopropyl-5-formyl-1H-pyrrole-2-carbonitrile (EV-AY4323-001) as a white powder. LCMS (method D): retention time 0.98 min, M/z=161 (M+1).

I-82

5-{5-[(1R,4R,7R)-7-Amino-2-azabicyclo[2.2.1]heptane-2-carbonyl]-7-methoxy-1-methyl-1H-1,3-benzodiazol-2-yl}-1-(2,2,2-trifluoroethyl)-1H-pyrrole-2-carbonitrile, 1-82, EV-AY4338-001 (EOA13468838) was synthesised according to the procedures described in Scheme 3 via synthesis of 5-formyl-1-(2,2,2-trifluoroethyl)-1H-pyrrole-2-carbonitrile EV-AY4332-001 as described in Scheme 3.3

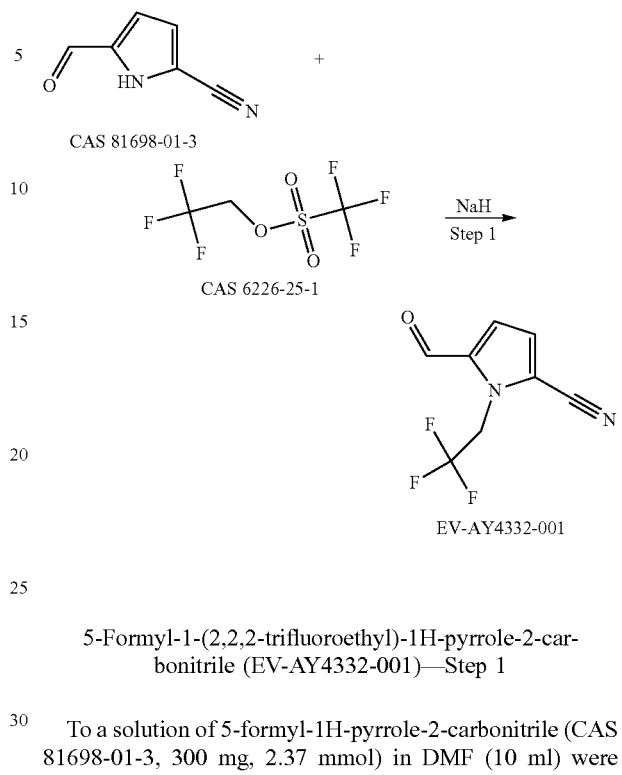

5-Formyl-1-(2,2,2-trifluoroethyl)-1H-pyrrole-2-carbonitrile (EV-AY4332-001)—Step 1

To a solution of 5-formyl-1H-pyrrole-2-carbonitrile (CAS 81698-01-3, 300 mg, 2.37 mmol) in DMF (10 ml) were added NaH (60%, 114 mg, 2.85 mmol) and 2,2,2-trifluoroethyl trifluoromethanesulfonate (582 µl, 4.03 mmol). The reaction was stirred at room temperature for 20 h. The reaction mixture was diluted with water (10 ml) and extracted with ethyl acetate (3×10 ml). The organic extracts were combined and washed with 5N NaOH (10 ml), saturated aqueous sodium chloride (10 ml), dried over sodium sulfate and concentrated in vacuo. The crude was purified by flash column chromatography (0-50% ethyl acetate/heptane) to obtain 406 mg (85%) of 5-formyl-1-(2,2,2-trifluoroethyl)-1H-pyrrole-2-carbonitrile (EV-AY4332-001) as a white solid. LCMS (method D) retention time 1.08 min, mass ion not observed.

I-86

(1R,4R,7R)-2-{2-[1-(Cyclopropylmethyl)-2-phenyl-1H-imidazol-5-yl]-1-ethyl-7-methoxy-1H-1,3-benzodiazole-5-carbonyl}-2-azabicyclo[2.2.1]heptan-7-amine, I-86, EV-AY4530-001 (EOA13469925) was synthesised according to the procedures described in Scheme 3 via synthesis of 1-(cyclopropylmethyl)-2-phenyl-1H-imidazole-5-carbaldehyde (EV-AW6299-002) as described in Scheme 3.4.

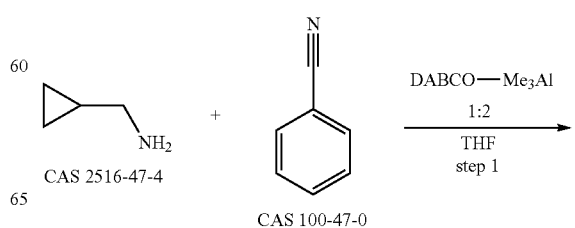

133

-continued

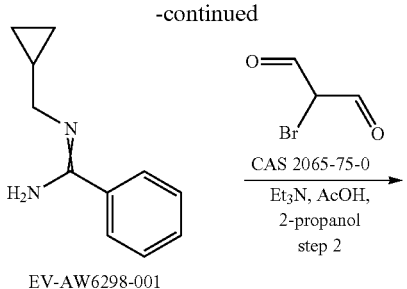

EV-AW6298-001

N'-(Cyclopropylmethyl)benzenecarboximidamide (EV-AW6298-001)—Step 1

To a solution of cyclopropylmethanamine (CAS 2516-47-4, 276 mg, 3.88 mmol) and benzonitrile (CAS 100-47-0, 400 mg, 3.88 mmol) in THF (8 ml) was slowly added 1,4-diazabicyclo[2.2.2]octane-trimethylaluminum (1:2) (994 mg, 3.88 mmol). The reaction mixture was heated to 130° C. under microwave condition for 6 h. The reaction was cooled down to 0° C. and slowly quenched with ethyl acetate (40 ml). Saturated Rochelle salt solution was added and the organic layer was separated, dried over magnesium sulfate, filtered and concentrated to obtain 594 mg (88%) of N'-(cyclopropylmethyl)benzenecarboximidamide (EV-AW6298-001) as a colourless oil. LCMS (method D): retention time 0.66 min, M/z=174 (M+1).

1-(Cyclopropylmethyl)-2-phenyl-1H-imidazole-5-carbaldehyde (EV-AW6299-002)—Step 2

A mixture of isopropanol (4 ml), (Z)—N'-(cyclopropylmethyl)benzene-1-carboximidamide (EV-AW6298-001, 594 mg, 3.41 mmol), triethylamine (0.44 ml, 3.14 mmol) and acetic acid (205 µl, 3.58 mmol) was stirred for 5 minutes at room temperature. Bromopropanedial (CAS 2065-75-0, 514 mg, 3.41 mmol) in isopropanol (4 ml) was added dropwise and the reaction mixture was heated for 16 h at 80° C. The reaction mixture was cooled down to room temperature and retreated with further bromopropanedial (154 mg, 1.02 mmol) and stirring at 80° C. was continued for 3 h. The solvent was evaporated, the residue was diluted with water (25 ml) and extracted with ethyl acetate (2×25 ml). The combined organic phases were dried over sodium sulfate, filtered and concentrated. The residue was purified by flash chromatography (10-70% ethyl acetate/heptane) to obtain 173 mg (20%) of 1-(cyclopropylmethyl)-2-phenyl-1H-imidazole-5-carbaldehyde (EV-AW6299-002) as an orange oil. LCMS (method D): retention time 1.08 min, M/z=227 (M+1).

134

I-89

5-{5-[(1R,4R,7R)-7-Amino-2-azabicyclo[2.2.1]heptane-2-carbonyl]-7-methoxy-1-methyl-1H-1,3-benzodiazol-2-yl}-1-{[(1R,3S)-3-methoxy-3-methylcyclobutyl]methyl}-1H-pyrrole-2-carbonitrile, I-89, EV-AY4541-001 (EOA13470261) was synthesised according to the procedures described in Scheme 3 via synthesis of 5-formyl-1-[(3-hydroxy-3-methylcyclobutyl)methyl]-1H-pyrrole-2-carbonitrile (EV-AZ4535-001) as described in Scheme 3.5.

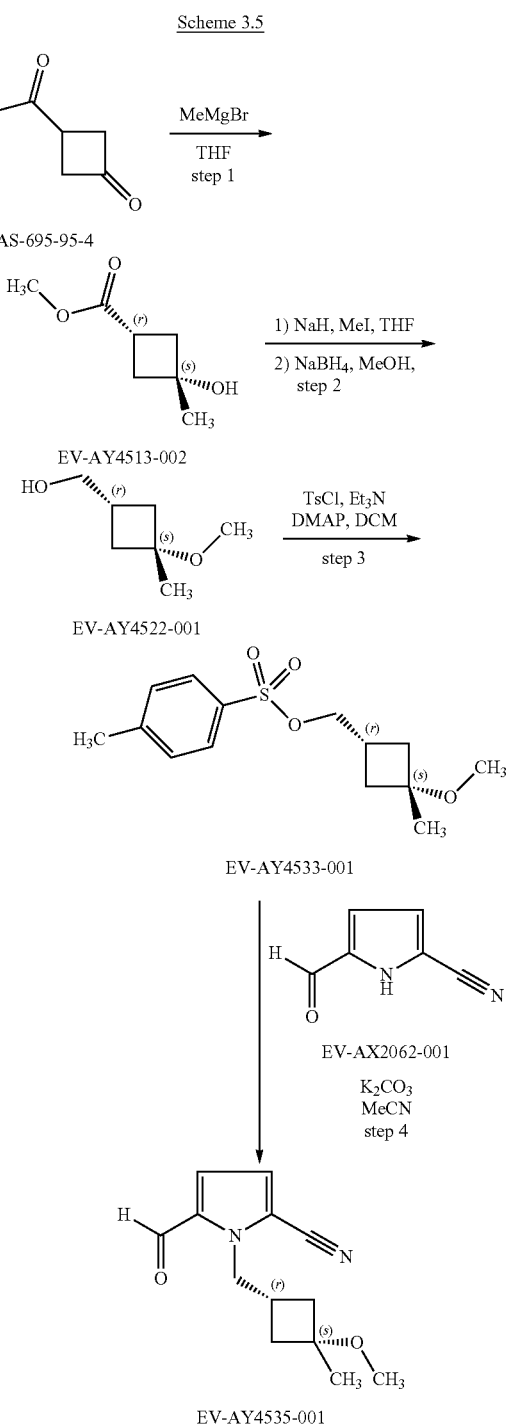

Methyl (1R,3S)-3-hydroxy-3-methylcyclobutane-1-carboxylate (EV-AY4513-002)—Step 1

To a solution of methyl 3-oxocyclobutane-1-carboxylate (CAS 695-95-4, 4.00 g, 31.2 mmol) in THF (100 ml) at −78° C., was added 1M methyl magnesium bromide in THF (35.9 ml, 35.9 mmol). The mixture was stirred at −78° C. for 2 h then allowed to warm to room temperature and stirred for 16 h. The reaction mixture was cooled down to −78° C. and a saturated solution of ammonium chloride (10 ml) was added. The resulting mixture was diluted with water (200 ml) and extracted with ethyl acetate (2×200 ml). The combined organic extracts were dried over sodium sulfate, filtered and concentrated. The residue was purified by column chromatography (0-100% ethyl acetate/heptane) to obtain 2.05 g (46%) of methyl (1R,3S)-3-hydroxy-3-methylcyclobutane-1-carboxylate (EV-AY4513-002) as a colourless oil. 1H NMR (500 MHz, Chloroform-d) δ 3.70-3.68 (m, 3H), 2.74-2.64 (m, 1H), 2.40-2.25 (m, 4H), 1.41-1.36 (m, 3H). No LCMS data. No LCMS data.

(1R,3S)-3-(Hydroxymethyl)-1-methylcyclobutan-1-ol (EV-AY4522-001)—Step 2

To methyl (1R,3S)-3-methoxy-3-methylcyclobutane-1-carboxylate (EV-AY4513-002, 250 mg, 1.73 mmol) and sodium hydride (60%, 73 mg, 1.82 mmol) was added dry DMF (3 ml) at 0° C. and the mixture was stirred at 0° C. for 15 minutes. Methyl iodide (0.22 ml, 3.47 mmol) was added, the mixture was warmed up to room temperature and stirred for 48 h. The reaction mixture was partitioned between ethyl acetate (80 ml) and water (80 ml). The aqueous extract was washed with further ethyl acetate (80 ml), the combined organic extracts were dried over sodium sulfate, filtered and concentrated. The residue was diluted with THF (3 ml) and methanol (0.3 ml) and sodium borohydride (197 mg, 5.20 mmol) was added. The mixture was stirred at room temperature for 16 h, concentrated in vacuo and purified by column chromatography (0-100% ethyl acetate/heptane) to obtain 107 mg (48%) of [(1R,3S)-3-methoxy-3-methylcyclobutyl]methanol (EV-AY4522-001) as a colourless oil. 1H NMR (500 MHz, Chloroform-d) δ 3.63 (d, J=6.2 Hz, 2H), 3.16 (s, 3H), 2.17-2.09 (m, 1H), 2.03-1.97 (m, 2H), 1.89-1.81 (m, 2H), 1.33 (s, 3H). No LCMS data.

[(1R,3S)-3-Methoxy-3-methylcyclobutyl]methyl 4-methylbenzene-1-sulfonate (EV-AY4533-001)—Step 3

To a solution of [(1R,3S)-3-methoxy-3-methylcyclobutyl] methanol (EV-AY4529-001, 305 mg, 1.76 mmol) in DCM (10 ml) with ice cooling were added triethylamine (0.32 ml, 2.28 mmol), DMAP (11 mg, 0.088 mmol) and 4-methylbenzene-1-sulfonyl chloride (352 mg, 1.84 mmol). The reaction mixture was allowed to warm to room temperature and stirred for 4 h. The mixture was partitioned between DCM (30 ml) and water (30 ml). The organic extract was dried over sodium sulfate, filtered and concentrated to obtain 480 mg (96%) of [(1R,3S)-3-methoxy-3-methylcyclobutyl] methyl 4-methylbenzene-1-sulfonate (EV-AY4533-001) as a viscous colourless oil. LCMS (method D): retention time 1.29 min, M/z=307 (M+23).

5-Formyl-1-{[(1R,3S)-3-methoxy-3-methylcyclobutyl]methyl}-1H-pyrrole-2-carbonitrile (EV-AY4535-001)—Step 4

To a solution of 5-formyl-1H-pyrrole-2-carbonitrile (EV-AY4533-001, 100 mg, 0.83 mmol) in acetonitrile (2 ml) was added potassium carbonate (288 mg, 2.08 mmol) followed by [(1R,3S)-3-methoxy-3-methylcyclobutyl]methyl 4-methylbenzene-1-sulfonate (EV-AY4533-001, 272 mg, 0.96 mmol). The mixture was stirred at 60° C. for 16 h, heated at 80° C. and left stirring at this temperature for 6 h. The mixture was poured into water (30 ml) and extracted with ethyl acetate (2×30 ml). The combined organic layers were dried over sodium sulfate, filtered and concentrated. The mixture was then retreated with potassium carbonate (288 mg, 2.08 mmol) and acetonitrile (2 ml) and stirred at 80° C. for 24 h. The mixture was poured into water (30 ml) and extracted with DCM (2×30 ml). The combined organic layers were washed with 2M NaOH (20 ml), dried over sodium sulfate, filtered and concentrated. The residue was purified by column chromatography (0-60% ethyl acetate/heptane) to obtain 68 mg (35%) of 5-formyl-1-{[(1R,3S)-3-methoxy-3-methylcyclobutyl]methyl}-1H-pyrrole-2-carbonitrile (EV-AY4535-001) as an off-white powder. LCMS (method D): retention time 1.29 min, =249 (M+water −1).

I-91

(1R,4R,7R)-2-{2-[6-(cyclopropylmethoxy)pyridin-2-yl]-7-methoxy-1-methyl-1H-1,3-benzodiazole-5-carbonyl}-2-azabicyclo[2.2.1]heptan-7-amine, I-91, EV-AY2043-002 (EOAI3476158) was synthesised according to the procedures described in Scheme 3.6 via synthesis of tert-butyl N-[1R,4R,7R)-2-[7-methoxy-1-methyl-2-(6-oxo-1,6-dihydropyridin-2-yl)-1H-1,3-benzodiazole-5-carbonyl]-2-azabicyclo[2.2.1]heptan-7-yl]carbamate (EV-AY2038-001) as described in Scheme 3.6.

Scheme 3.6

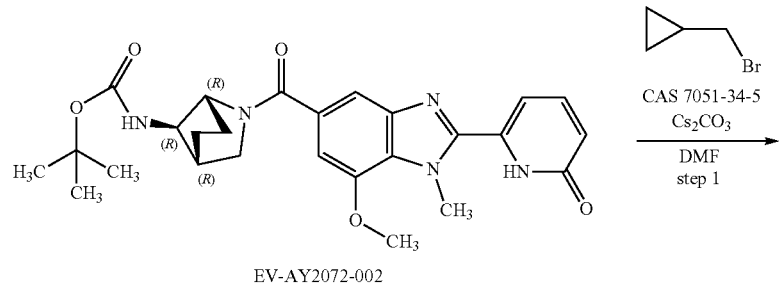

EV-AY2072-002

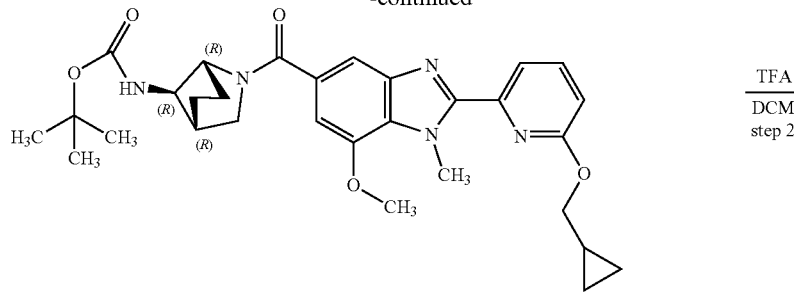

EV-AY2040-001

TFA
DCM
step 2

EV-AY2043-002

Tert-butyl N-[(1R,4R,7R)-2-{2-[6-(cyclopropylmethoxy)pyridin-2-yl]-7-methoxy-1-methyl-1H-1,3-benzodiazole-5-carbonyl}-2-azabicyclo[2.2.1]heptan-7-yl]carbamate(EV-AY2040-001)—Step 1

Tert-butyl N-[(1R,4R,7R)-2-[7-methoxy-1-methyl-2-(6-oxo-1,6-dihydropyridin-2-yl)-1H-1,3-benzodiazole-5-carbonyl]-2-azabicyclo[2.2.1]heptan-7-yl]carbamate (137 mg, 0.25 mmol) was dissolved in dry DMF (2 ml) under an atmosphere of nitrogen and treated with Cs₂CO₃ (98 mg, 0.30 mmol). The resulting mixture was stirred at room temperature for 2-3 minutes, (bromomethyl)cyclopropane (CAS 7051-34-5, 27 µl, 0.27 mmol) was added in one portion and the reaction mixture was stirred at room temperature for 16 h. The mixture was diluted with water (10 ml), saturated ammonium chloride (6 ml) and extracted with ethyl acetate (3×20 ml). The combined organic extracts were dried over sodium sulfate, filtered and concentrated. The residue was purified by column chromatography (0-15% methanol/DCM) to obtain 184 mg of tert-butyl N-[(1R,4R,7R)-2-{2-[6-(cyclopropylmethoxy)pyridin-2-yl]-7-methoxy-1-methyl-1H-1,3-benzodiazole-5-carbonyl}-2-azabicyclo[2.2.1]heptan-7-yl]carbamate (EV-AY2040-001) as a pale yellow glass. LCMS (method D): retention time 1.32 min, M/z=548 (M+1).

Tert-butyl N-[(1R,4R,7R)-2-[7-methoxy-1-methyl-2-(6-oxo-1,6-dihydropyridin-2-yl)-1H-1,3-benzodiazole-5-carbonyl]-2-azabicyclo[2.2.1]heptan-7-yl]carbamate (EV-AY2043-002)—Step 2

Tert-butyl N-[(1R,4R,7R)-2-{2-[1-(cyclopropylmethyl)-6-oxo-1,6-dihydropyridin-2-yl]-7-methoxy-1-methyl-1H-1,3-benzodiazole-5-carbonyl}-2-azabicyclo[2.2.1]heptan-7-yl]carbamate (EV-AY2040-001, 76%, 184 mg, 0.26 mmol) was dissolved in DCM (4 ml) under an atmosphere of nitrogen at room temperature and treated with trifluoroacetic acid (0.6 ml). The mixture was stirred at room temperature for 2 hours. The reaction mixture was concentrated and purified by prep HPLC (acidic method) to obtain 27 mg (23%) of (1R,4R,7R)-2-{2-[6-(cyclopropylmethoxy)pyridin-2-yl]-7-methoxy-1-methyl-1H-1,3-benzodiazole-5-carbonyl}-2-azabicyclo[2.2.1]heptan-7-amine (EV-AY2043-002) as a white glass/foam. LCMS (method A): retention time 2.03 min, M/z=448 (M+1).

I-102

6-{5-[(1R,4R,7R)-7-Amino-2-azabicyclo[2.2.1]heptane-2-carbonyl]-7-methoxy-1-methyl-1H-1,3-benzodiazol-2-yl}-1-(cyclopropylmethyl)-1,2-dihydropyridin-2-one, 1-102, EV-AY2061-002 (EOA13477377) was synthesised according to the procedures described in Scheme 3 via synthesis of 5-formyl-1-[(3-hydroxy-3-methylcyclobutyl)methyl]-1H-pyrrole-2-carbonitrile (EV-AY2050-001) as described in Scheme 3.7.

Scheme 3.7

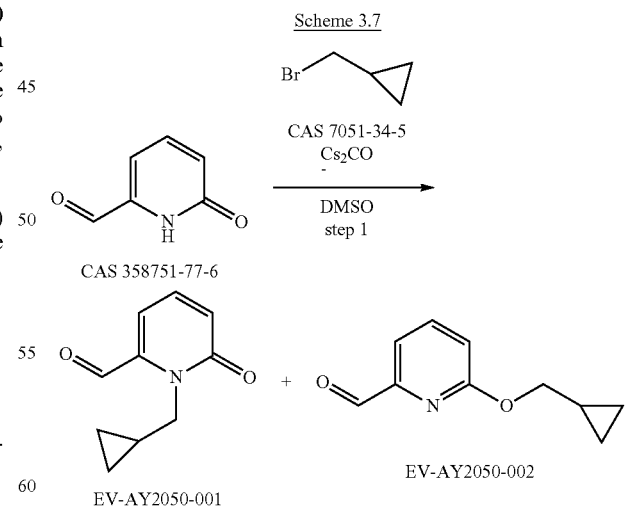

1-(Cyclopropylmethyl)-6-oxo-1,6-dihydropyridine-2-carbaldehyde (EV-AY2050-001)—Step 1

6-Oxo-1,6-dihydropyridine-2-carbaldehyde (CAS 358751-77-6, 294 mg, 2.39 mmol) was dissolved in dry DMSO (10 ml) under an atmosphere of nitrogen and treated with $Cs_2CO_3$ (934 mg, 2.87 mmol) and (bromomethyl)cyclopropane (CAS 7051-34-5, 0.25 ml, 2.63 mmol). The reaction mixture was stirred at room temperature for 16 h, diluted with water (20 ml) and extracted with ethyl acetate (3×20 ml). The combined organic extracts were washed with water, saturated aqueous sodium chloride, dried over sodium sulfate, filtered and concentrated. The residue was purified by column chromatography (10-100% ethyl acetate/heptane) to obtain 0.16 g (38%) of 1-(cyclopropylmethyl)-6-oxo-1,6-dihydropyridine-2-carbaldehyde (EV-AY2050-001) as a dark green gum, LCMS (method D): retention time 0.92 min, M/z=178 (M+1), and 0.21 g of 6-(cyclopropylmethoxy)pyridine-2-carbaldehyde (EV-AY2050-002) as a colourless oil, LCMS (method D): retention time 1.18 min, M/z=178 (M+1).

I-106

(1R,4R,7R)-2-[2-(2-ethyl-5-methyl-1-phenyl-1H-pyrrol-3-yl)-7-methoxy-1-methyl-1H-1,3-benzodiazole-5-carbonyl]-2-azabicyclo[2.2.1]heptan-7-amine, 1-106, EV-AY4657-002 (EOA13478191) was synthesised from the Boc deprotection of tert-butyl N-[(1R,4R,7R)-2-[2-(2-ethyl-5-methyl-1-phenyl-1H-pyrrol-3-yl)-7-methoxy-1-methyl-1H-1,3-benzodiazole-5-carbonyl]-2-azabicyclo[2.2.1]heptan-7-yl]carbamate (EV-AY2064-001) as described in Scheme 3.8.

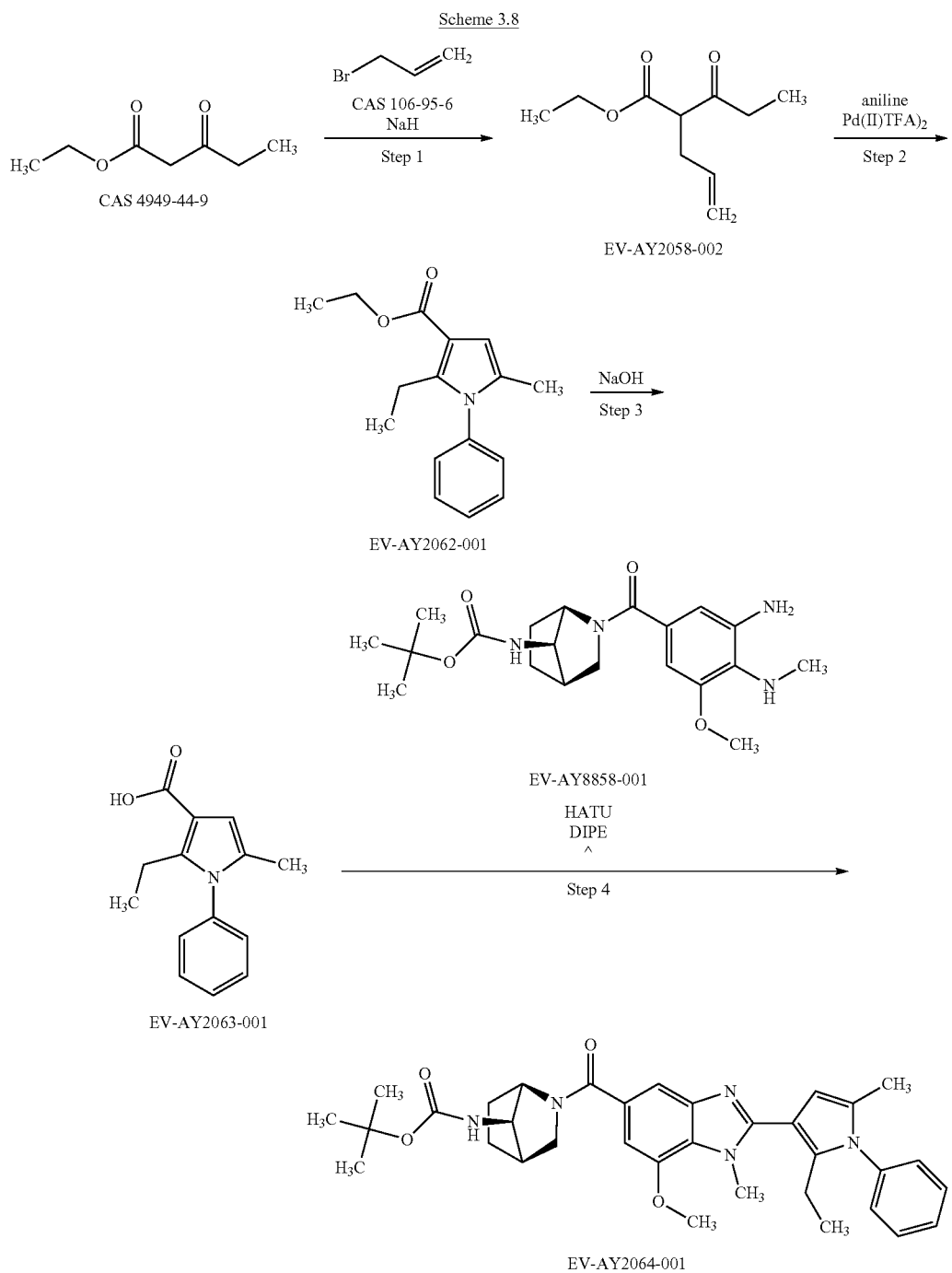

Ethyl 2-propanoylpent-4-enoate (EV-AY2058-002)—Step 1

Ethyl 3-oxopentanoate (CAS 4949-44-4, 500 mg, 3.47 mmol) was dissolved in dry DMF (2.5 ml) under an atmosphere of nitrogen and the resulting mixture was cooled to 0° C. The reaction mixture was treated with sodium hydride (60%, 166 mg, 4.16 mmol) and stirred at 0° C. for 30 minutes then 3-bromoprop-1-ene (CAS 106-95-6, 360 µl, 4.16 mmol) was added dropwise over 10 minutes. The reaction mixture was allowed to warm to room temperature and stirred for 17 h then diluted with water (20 ml) and extracted with TBME (3×25 ml). The combined organics were washed with saturated aqueous sodium chloride (30 ml), dried over sodium sulfate and concentrated in vacuo. The crude product was purified by flash column chromatography (0-5% ethyl acetate/heptane) to obtain 341 mg (49%) of ethyl 2-propanoylpent-4-enoate (EV-AY2058-002) as a colourless oil. LCMS (method D): retention time 1.21 min, mass ion not observed.

Ethyl 2-ethyl-5-methyl-1-phenyl-1H-pyrrole-3-carboxylate (EV-AY2062-001)—Step 2

Ethyl 2-propanoylpent-4-enoate (EV-AY2058-002, 341 mg, 1.68 mmol) was dissolved in dry toluene (3 ml) and aniline (77 µl, 0.84 mmol) and palladium(II) bis(trifluoroacetate) (28 mg, 0.08 mmol) were added. The reaction mixture was stirred at 60° C. for 18 h, cooled down to room temperature, diluted with ethyl acetate (5 ml) and filtered through a pad of Kieselguhr, washing with ethyl acetate (30 ml). The filtrate was concentrated in vacuo and purified by flash column chromatography (0-40% ethyl acetate/heptane) to obtain 313 mg (38%) of ethyl 2-ethyl-5-methyl-1-phenyl-1H-pyrrole-3-carboxylate (EV-AY2062-001) as a pale yellow oil. LCMS (method D): retention time 1.34 min, M/z=258 (M+1).

2-Ethyl-5-methyl-1-phenyl-1H-pyrrole-3-carboxylic acid (EV-AY2063-001)—Step 3

1M aqueous NaOH (0.95 ml) was added to a solution of ethyl 2-ethyl-5-methyl-1-phenyl-1H-pyrrole-3-carboxylate (EV-AY2062-001, 313 mg, 0.63 mmol) in methanol (5 ml) and the resultant mixture was stirred at 50° C. for 2 h. Further 1M NaOH (0.95 ml) was added and the mixture was stirred at 60° C. for 16 h then 80° C. for 20 h. The reaction mixture was allowed to cool to room temperature and concentrated in vacuo. Water (7 ml) was added then 1N HCl until pH 2. The resulting precipitate was filtered off, washed with water (2×3 ml) and dried to obtain 87 mg (58%) of 2-ethyl-5-methyl-1-phenyl-1H-pyrrole-3-carboxylic acid (EV-AY2063-001) as a pale beige solid. LCMS (method D): retention time 0.86 min, M/z=230 (M+1).

Tert-butyl N-[(1R,4R,7R)-2-[2-(2-ethyl-5-methyl-1-phenyl-1H-pyrrol-3-yl)-7-methoxy-1-methyl-1H-1,3-benzodiazole-5-carbonyl]-2-azabicyclo[2.2.1]heptan-7-yl]carbamate (EV-AY2064-001)—Step 4

2-Ethyl-5-methyl-1-phenyl-1H-pyrrole-3-carboxylic acid (EV-AY2063-001, 87 mg, 0.36 mmol) was dissolved in DMF (1 ml) under an atmosphere of nitrogen and treated with HATU (166 mg, 0.44 mmol) and DIPEA (76 µl, 0.44 mmol). The reaction mixture was stirred at room temperature for 15 minutes then tert-butyl N-[(1R,4R,7R)-2-[3-amino-5-methoxy-4-(methylamino)benzoyl]-2-azabicyclo[2.2.1]heptan-7-yl]carbamate (EV-AY8858-001, synthesised according to the procedures described in Scheme 5, 142 mg, 0.36 mmol) was added and the reaction stirred at room temperature for 2.5 h then 50° C. for 2 h. The reaction was left standing at room temperature for 18 h then stirred at 40° C. for 22 h. The reaction mixture was concentrated in vacuo and azeotroped with toluene (5 ml). The crude material was purified by flash column chromatography (50-100% ethyl acetate/heptane) to obtain tert-butyl N-[(1R,4R,7R)-2-[2-(2-ethyl-5-methyl-1-phenyl-1H-pyrrol-3-yl)-7-methoxy-1-methyl-1H-1,3-benzodiazole-5-carbonyl]-2-azabicyclo[2.2.1]heptan-7-yl]carbamate (EV-AY2064-001) as a yellow glassy solid. LCMS (method D): retention time 1.19 min, M/z=584 (M+1).

I-97 and I-98

(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-amine, I-97, EV-AY2056-002 (EOAI3476816) and (1R,4R,7R)—N-benzyl-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-amine, I-98, EV-AY2057-002 (EOAI3476817) were obtained via Boc deprotection of tert-butyl N-[(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2054-002) and tert-butyl N-benzyl-N-[(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2054-003) respectively. These were synthesised according to the procedures described in Scheme 4.

Scheme 4

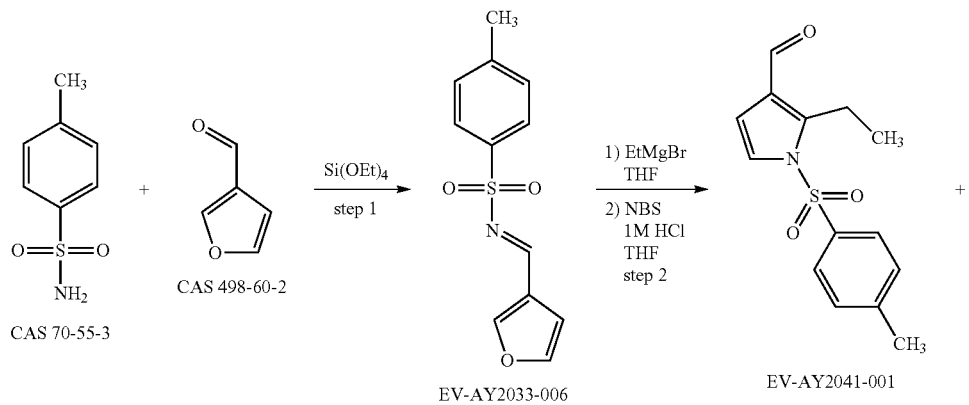

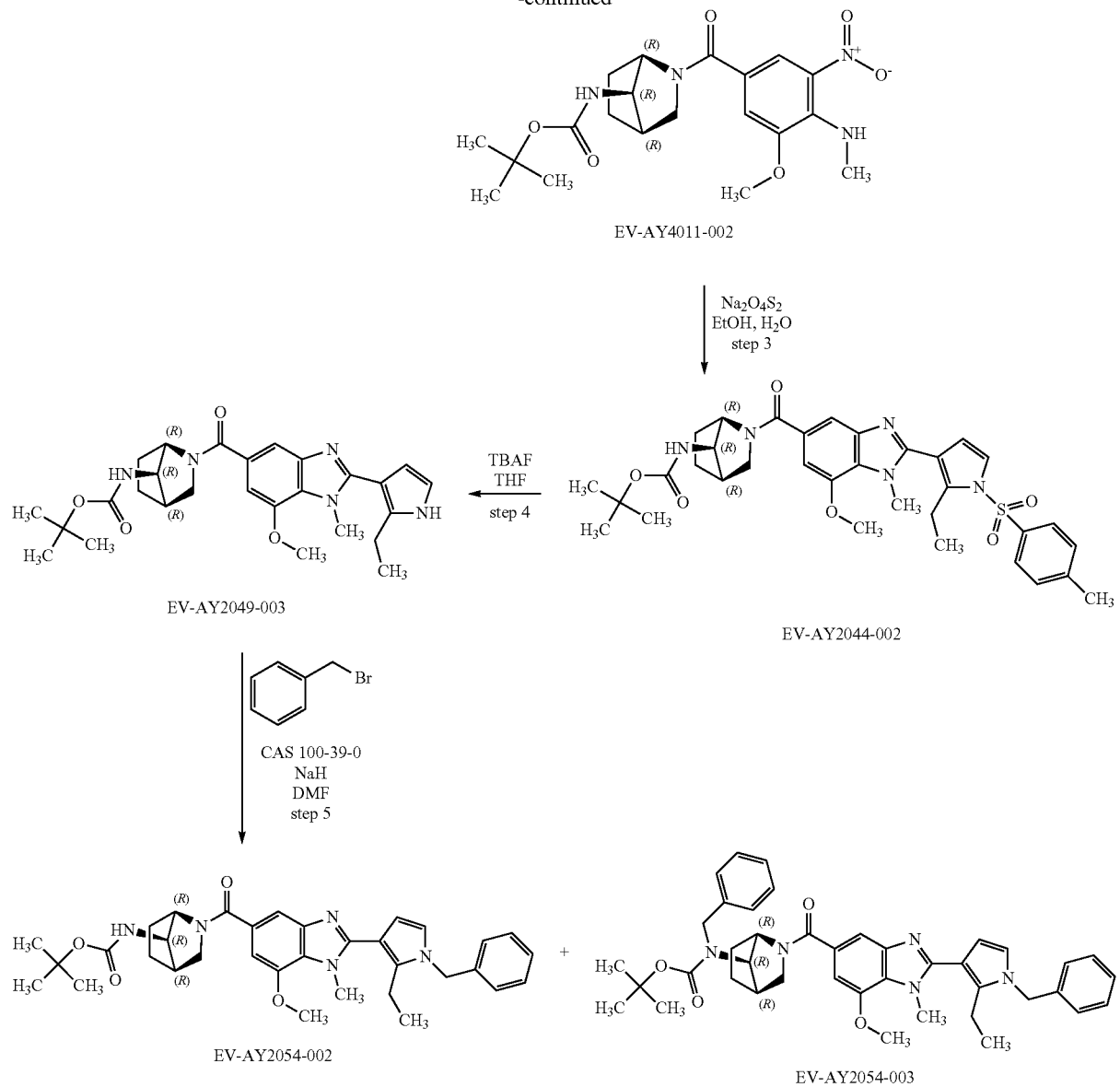

N-[(1E)-furan-3-ylmethylidene]-4-methylbenzene-1-sulfonamide (EV-AY2033-006)—Step 1

4-Methylbenzenesulfonamide (CAS 70-55-3, 1.00 g, 5.84 mmol) and furan-3-carbaldehyde (CAS 498-60-2, 0.49 ml, 5.84 mmol) were suspended in tetraethyl orthosilicate (1.43 ml, 6.42 mmol). The vessel was sealed and heated to 160° C. for 4 h. The reaction was cooled down to room temperature and diluted with diethyl ether (4 ml), stirred and filtered to obtain 0.81 g (52%) of N-[(1E)-furan-3-ylmethylidene]-4-methylbenzene-1-sulfonamide (EV-AY2033-006) as a brown solid. LCMS (method D): retention time 1.12 min, M/z=250 (M+1).

2-Ethyl-1-(4-methylbenzenesulfonyl)-1H-pyrrole-3-carbaldehyde (EV-AY2041-001)—Step 2

3M Bromo(ethyl)magnesium (1.90 ml) was added dropwise over 5 minutes to a stirred solution of N-[(1E)-furan-3-ylmethylidene]-4-methylbenzene-1-sulfonamide (EV-AY2033-006, 604 mg, 2.28 mmol) in dry THF (10 ml) at 0° C. under an atmosphere of nitrogen. The mixture was left stirring at room temperature for 3 h then cooled to 0° C. and treated with 1M HCl in water (5.7 ml). The reaction was diluted with THF (15 ml) and 1-bromopyrrolidine-2,5-dione (405 mg, 2.28 mmol) was added in one portion. The reaction mixture was stirred at room temperature for 16 h, diluted with saturated ammonium chloride (12 ml) and water (5 ml) and extracted with ethyl acetate. The combined organics were washed with saturated aqueous sodium chloride, dried over sodium sulfate, filtered and concentrated. The residue was purified by column chromatography (10-20% ethyl acetate/heptane) to obtain 348 mg (47%) of 2-ethyl-1-(4-methylbenzenesulfonyl)-1H-pyrrole-3-carbaldehyde (EV-AY2041-001) as a colourless oil. LCMS (method D): retention time 1.32 min, M/z=278 (M+1).

2-Ethyl-1-(4-methylbenzenesulfonyl)-1H-pyrrole-3-carbaldehyde (EV-AY2044-002)—Step 3

Tert-butyl N-[(1R,4R,7R)-2-[3-methoxy-4-(methylamino)-5-nitrobenzoyl]-2-azabicyclo[2.2.1]heptan-7-yl]carbamate (EV-AY4011-002 synthesised according to Scheme 5 steps 1-3, 0.78 g, 1.57 mmol) and 2-ethyl-1-(4-methylbenzenesulfonyl)-1H-pyrrole-3-carbaldehyde (EV-AY2041-001, 0.43 g, 1.56 mmol) were dissolved in ethanol (15 ml) and water (7.5 ml). Disodium dithionite (2.45 g, 14.1 mmol) was added in one portion and the reaction mixture was stirred at 90° C. for 4 h. The mixture was cooled to room temperature, diluted with water (15 ml) and extracted with ethyl acetate. The combined organics were washed with saturated aqueous sodium chloride, dried over sodium sulfate, filtered and concentrated in vacuo. The residue was purified by column chromatography (0-5% methanol/DCM) to obtain 0.71 g of tert-butyl N-[(1R,4R,7R)-2-{2-[2-ethyl-1-(4-methylbenzenesulfonyl)-1H-pyrrol-3-yl]-7-methoxy-1-methyl-1H-1,3-benzodiazole-5-carbonyl}-2-azabicyclo[2.2.1]heptan-7-yl]carbamate (EV-AY2044-002) as a white foam. LCMS (method D): retention time 1.32 min, M/z=648.3 (M+1).

Tert-butyl N-[(1R,4R,7R)-2-[2-(2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2049-003)—Step 4

Tert-butyl N-[(1R,4R,7R)-2-{2-[2-ethyl-1-(4-methylbenzenesulfonyl)-1H-pyrrol-3-yl]-7-methoxy-1-methyl-1H-1,3-benzodiazole-5-carbonyl}-2-azabicyclo[2.2.1]heptan-7-yl]carbamate (EV-AY2044-002, 573 mg, 0.8 mmol) was dissolved in dry THF (15 ml) under an atmosphere of nitrogen and treated with 1M N,N,N-tributylbutan-1-aminium fluoride in THF (2.39 ml). The mixture was stirred at room temperature for 16 h then at 40° C. for 5 h. Further 1M N,N,N-tributylbutan-1-aminium fluoride in THF (1.1 ml) was added and stirring at 50° C. was continued for 16 h. The mixture was diluted with saturated ammonium chloride (20 ml) and extracted with ethyl acetate. The combined organics were washed with saturated aqueous sodium chloride, dried over sodium sulfate, filtered and concentrated in vacuo. The residue was purified by column chromatography (0-10% methanol/DCM) followed by purification on SCX-2 cartridge to obtain 313 mg of (77%) of tert-butyl N-[(1R,4R,7R)-2-[2-(2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2049-003) as a pink beige solid. LCMS (method D): retention time 1.03 min, M/z=494 (M+1).

Tert-butyl N-[(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2054-002) and tert-butyl N-benzyl-N-[(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2054-003)—Step 5

Tert-butyl N-[(1R,4R,7R)-2-[2-(2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2049-003, 100 mg, 0.19 mmol) was dissolved in dry DMF (2 ml) under an atmosphere of nitrogen and cooled to 0° C. The reaction mixture was treated with sodium hydride (60%, 11 mg, 0.27 mmol) in one portion and stirred at 0° C. for 15 minutes. The reaction mixture was treated with (bromomethyl)benzene (CAS 100-39-0, 23 µl, 0.19 mmol) and stirred for a further 3 h at room temperature. The mixture was diluted with saturated ammonium chloride (12 ml) and water (3 ml), heptane (8 ml) was added, the mixture was stirred and filtered and the solid was purified by column chromatography (0-5% methanol/ethyl acetate) to obtain 74 mg (57%) of tert-butyl N-[(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2054-002) as a pale yellow glass, LCMS (method D): retention time 1.24 min, M/z=584 (M+1).

21 mg (15.1%) of tert-butyl N-benzyl-N-[(1R,4R,7R)-2-[2-(1-benzyl-2-ethyl-1H-pyrrol-3-yl)-7-methoxy-1-methyl-1H-1,3-benzodiazole-5-carbonyl]-2-azabicyclo[2.2.1]heptan-7-yl]carbamate (EV-AY2054-003) were also isolated as a pale yellow glass. LCMS (method D): retention time 1.37 min, M/z=674 (M+1).

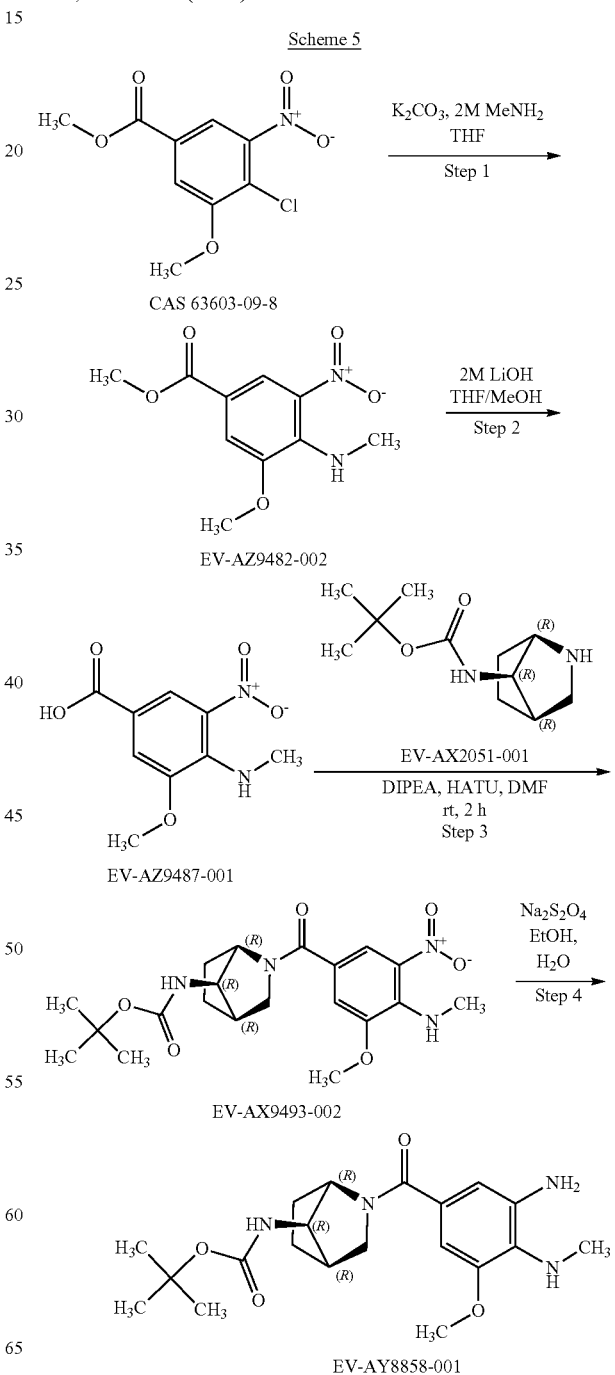

Scheme 5

Methyl 3-methoxy-4-(methylamino)-5-nitrobenzoate (EV-AX9482-002) Step 1

Potassium carbonate (11.3 g, 81.4 mmol) and 2 M MeNH$_2$ in THF (61 ml) were added at room temperature to a stirred solution of methyl 4-chloro-3-methoxy-5-nitrobenzoate (CAS 63603-09-8, 10.0 g, and 40.71 mmol) in THF (180 ml). The resulting mixture was stirred at 60° C. for 24 h and concentrated in vacuo. The residue was re-dissolved in ethyl acetate (500 ml), washed with water (2×250 ml) and saturated aqueous sodium chloride (200 ml). The organic extracts were dried over sodium sulfate and concentrated in vacuo to afford 9.38 g (96%) of methyl 3-methoxy-4-(methylamino)-5-nitrobenzoate (EV-AX9482-001) as an orange powder. LCMS (method D): retention time 1.30 min, M/z=241 (M+1).

3-Methoxy-4-(methylamino)-5-nitrobenzoic acid (EV-AX9487-001)—step 2

2M aqueous LiOH (58.2 ml) was added to a solution of methyl 3-methoxy-4-(methylamino)-5-nitrobenzoate (EV-AX9482-002, 9.32 g, 38.8 mmol) in THF:methanol (4:1) (75 ml) and the resulting mixture was stirred at 50° C. for 5 h. The reaction mixture was concentrated in vacuo, re-dissolved in water (50 ml, and acidified to pH 2 using 2 M aqueous HCl. The precipitate was filtered under vacuum to afford 9.75 g (quantitative) of 3-methoxy-4-(methylamino)-5-nitrobenzoic acid (EV-AX9487-001) as a bright orange powder. LCMS (method D): retention time 1.01 min, M/z=227 (M+1).

Tert-butyl N-[(1R,4R,7R)-2-[3-methoxy-4-(methylamino)-5-nitrobenzoyl]-2-azabicyclo[2.2.1]heptan-7-yl]carbamate (EV-AX9493-002)—Step 3

DIPEA (6.58 ml, 39.79 mmol) and HATU (11.4 g, 29.8 mmol) were added to a solution of 3-methoxy-4-(methylamino)-5-nitrobenzoic acid (EV-AX9487-001, 90%, 5.00 g, 19.9 mmol) in DMF (60 ml) and the resulting mixture was stirred at room temperature for 10 minutes. Tert-butyl N-[(1R,4R,7R)-2-azabicyclo[2.2.1]heptan-7-yl]carbamate (EV-AX2051-001, 4.43 g, 20.89 mmol) (synthesised as in *Adv. Synth. Catal.* 2005, 347, 1242-1246) was added to the reaction mixture and stirring at room temperature was continued for 2 h. The reaction mixture was concentrated in vacuo and the resulting residue was dissolved in ethyl acetate (250 ml), washed with water (2×100 ml) and saturated aqueous sodium chloride (100 ml). The organic extracts were dried over sodium sulfate, concentrated in vacuo and purified by flash column chromatography (0-100% ethyl acetate/heptane) to obtain 6.39 g (76%) of tert-butyl N-[(1R,4R,7R)-2-[3-methoxy-4-(methylamino)-5-nitrobenzoyl]-2-azabicyclo[2.2.1]heptan-7-yl]carbamate (EV-AX9493-002) as a red powder. LCMS (method D): retention time 1.19 min, M/z=421 (M+1).

Tert-butyl N-[(1R,4R,7R)-2-[3-amino-5-methoxy-4-(methylamino)benzoyl]-2-azabicyclo[2.2.1]heptan-7-yl]carbamate (EV-AY8858-001)—Step 4

Na$_2$S$_2$O$_4$ (85%, 14.6 g, 71.4 mmol) was added to a solution of tert-butyl N-[(1R,4R,7R)-2-[3-methoxy-4-(methylamino)-5-nitrobenzoyl]-2-azabicyclo[2.2.1]heptan-7-yl]carbamate (EV-AX9493-002, 3.00 g, 7.14 mmol) in ethanol (20 ml) and water (10 ml) and the resulting mixture was stirred at 90° C. for 3 h. The reaction mixture was diluted with water (50 ml) and the resulting solution was extracted with ethyl acetate (2×100 ml). The combined organic extracts were dried over sodium sulfate and concentrated in vacuo to afford 2.71 g (97%) of tert-butyl N-[(1R,4R,7R)-2-[3-amino-5-methoxy-4-(methylamino)benzoyl]-2-azabicyclo[2.2.1]heptan-7-yl]carbamate (EV-AY8858-001) as an off-white powder. LCMS (method D): retention time 0.82 min, M/z=391 (M+1).

Scheme 6

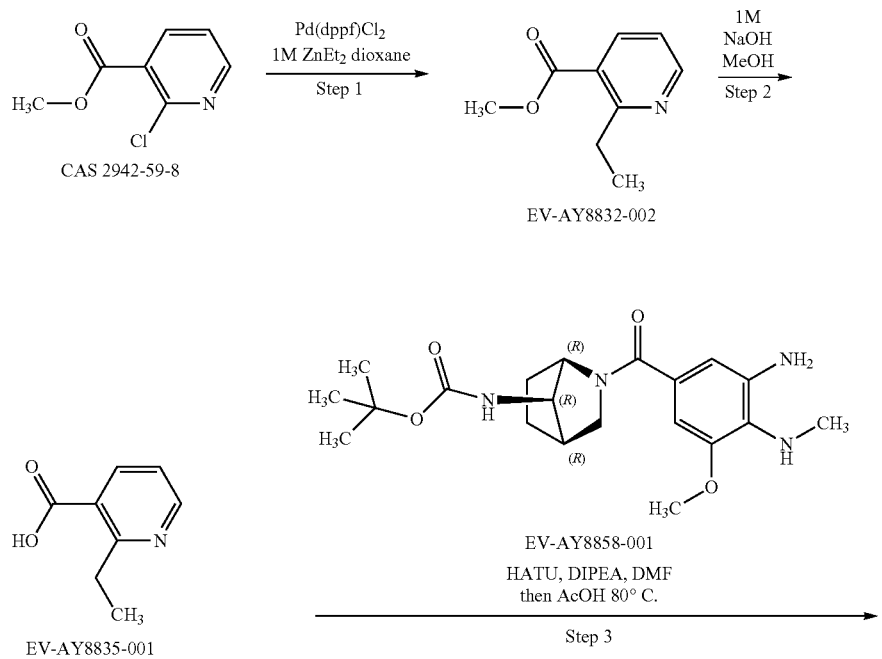

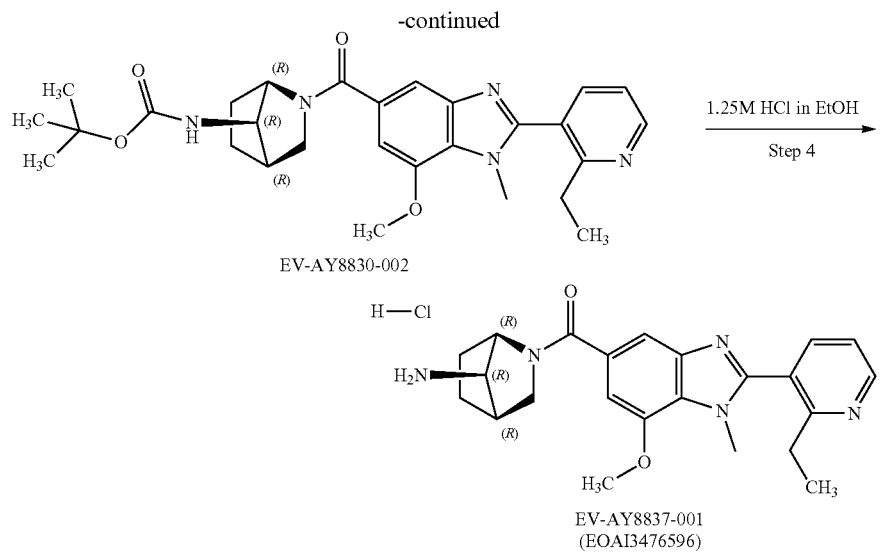

EV-AY8830-002

1.25M HCl in EtOH
Step 4

EV-AY8837-001
(EOAI3476596)

Methyl 2-ethylpyridine-3-carboxylate (EV-AY8832-002)—Step 1

Pd(dppf)Cl$_2$ (299 mg, 0.41 mmol) and 1M diethylzinc in hexane (4.9 ml) were added to a solution of methyl 2-chloropyridine-3-carboxylate (CAS 2942-59-8, 532 μl, 4.08 mmol) in dry dioxane (7 ml) and the resulting mixture was stirred under nitrogen at 60° C. for 2 h. The reaction mixture was diluted with water (20 ml) and extracted with ethyl acetate (3×50 ml). The combined organic extracts were dried over sodium sulfate, concentrated in vacuo and purified by column chromatography (0-100% ethyl acetate/heptane) to afford 647 mg (96%) of methyl 2-ethylpyridine-3-carboxylate (EV-AY8832-002) as a colourless volatile oil. LCMS (method D): retention time 0.79 min, M/z=166 (M+1).

2-Ethylpyridine-3-carboxylic acid (EV-AY8835-001)—Step 2

1M aqueous NaOH (5.51 ml) was added to a solution of methyl 2-ethylpyridine-3-carboxylate (EV-AY8832-002, 607 mg, 3.67 mmol) in methanol (5 ml) and the resulting mixture was stirred at 50° C. for 2 h. The reaction mixture was concentrated in vacuo, the residue was dissolved in water (10 ml) and acidified to pH 3 using 2 M aqueous HCl solution. The solution was extracted with ethyl acetate (2×50 ml), the combined organic extracts were dried over sodium sulfate and concentrated in vacuo to afford 354 mg (64%) of 2-ethylpyridine-3-carboxylic acid (EV-AY8835-001) as an off-white powder. LCMS (method D): retention time 0.22 min, M/z=152 (M+1).

Tert-butyl N-[(1R,4R,7R)-2-[2-(2-ethylpyridin-3-yl)-7-methoxy-1-methyl-1H-1,3-benzodiazole-5-carbonyl]-2-azabicyclo[2.2.1]heptan-7-yl]carbamate (EV-AY8830-002)—Step 3

HATU (224 mg, 0.59 mmol) and DIPEA (103 μl, 0.59 mmol) were added to a solution of 2-ethylpyridine-3-carboxylic acid (EV-AY8835-001, 77 mg, 0.51 mmol) in DMF (3 ml) and the resulting mixture was stirred at room temperature for 10 minutes. Tert-butyl N-[(1R,4R,7R)-2-[3-amino-5-methoxy-4-(methylamino)benzoyl]-2-azabicyclo[2.2.1]heptan-7-yl]carbamate (EV-AY8858-001 synthesised according to Scheme 5, 200 mg, 0.51 mmol) was added and the reaction mixture was stirred at room temperature for 24 h. The reaction mixture was concentrated in vacuo, dissolved in acetic acid (3 ml) and stirred at 80° C. for 4 h. The reaction mixture was concentrated in vacuo and the resulting residue was purified by preparative HPLC (basic method) to afford 153 mg (59%) of tert-butyl N-[(1R,4R,7R)-2-[2-(2-ethylpyridin-3-yl)-7-methoxy-1-methyl-1H-1,3-benzodiazole-5-carbonyl]-2-azabicyclo[2.2.1]heptan-7-yl]carbamate (EV-AY8830-002) as an off-white powder. LCMS (method D): retention time 1.10 min, M/z=506 (M+1).

(1R,4R,7R)-2-[2-(2-Ethylpyridin-3-yl)-7-methoxy-1-methyl-1H-1,3-benzodiazole-5-carbonyl]-2-azabicyclo[2.2.1]heptan-7-amine hydrochloride, I-96 (EV-AY8837-001)—Step 4

1.25M HCl in ethanol (2 ml) was added to a solution of tert-butyl N-[(1R,4R,7R)-2-[2-(2-ethylpyridin-3-yl)-7-methoxy-1-methyl-1H-1,3-benzodiazole-5-carbonyl]-2-azabicyclo[2.2.1]heptan-7-yl]carbamate (EV-AY8830-002, 95 mg, 0.19 mmol) in ethanol (4 ml) and the resulting mixture was stirred at 50° C. for 16 h. The reaction mixture was concentrated in vacuo to afford a white powder. The compound was taken up in methanol (10 ml) and treated with Smopex-105 (CAS 527751-99-1) metal scavenger (95 mg) and stirred at room temperature for 2 h. The fibres were removed by vacuum filtration and the filtrate concentrated in vacuo to afford 83 mg (quantitative) of (1R,4R,7R)-2-[2-(2-Ethylpyridin-3-yl)-7-methoxy-1-methyl-1H-1,3-benzodiazole-5-carbonyl]-2-azabicyclo[2.2.1]heptan-7-amine hydrochloride, I-96 (EV-AY8837-001) as a white powder. LCMS (method H): retention time 2.13 min, M/z=406 (M+1).

Special cases for Scheme 6

I-103

(1R,4R,7R)-2-[2-(2-Ethyl-5-methoxypyridin-3-yl)-7-methoxy-1-methyl-1H-1,3-benzodiazole-5-carbonyl]-2-azabicyclo[2.2.1]heptan-7-amine, I-103, EV-AY8854-001 (EOAI3477379) was synthesised according to the procedures described in Scheme 6 via synthesis of 2-ethyl-5-methoxypyridine-3-carboxylic acid (EV-AY8846-001) as described in Scheme 6.1

Scheme 6.1

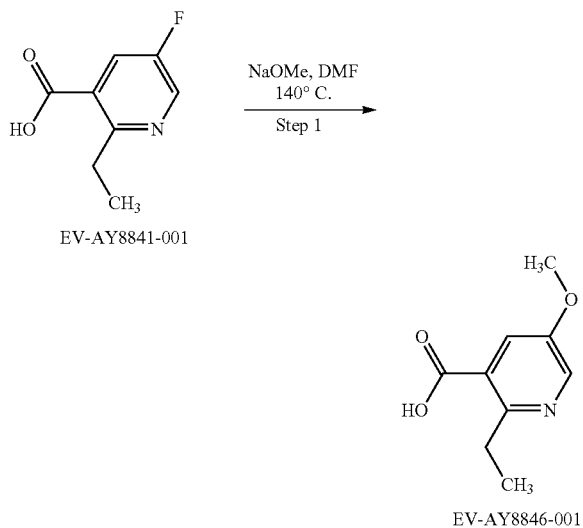

2-Ethyl-5-methoxypyridine-3-carboxylic acid (EV-AY8846-001)—Step 1

NaOMe (199 mg, 3.69 mmol) was added to a solution of EV-AY8841-001 (synthesised according to Scheme 6, step 1 starting from CAS 1214351-19-5, 208 mg, 1.23 mmol) in DMF (3 ml) and the resulting mixture was stirred at 140° C. for 2 h. The reaction mixture was diluted with water (20 ml) and acidified to pH 3 using 5M aqueous HCl solution. The resulting solution was extracted with ethyl acetate (2×100 ml), the combined organic extracts were dried over sodium sulfate and concentrated in vacuo to afford 190 mg (85%) of 2-ethyl-5-methoxypyridine-3-carboxylic acid (EV-AY8846-001) as an off-white powder. LCMS (method D): retention time 0.37 min, M/z=182 (M+1).

I-99 and I-100

(1R,4R,7R)-2-[2-(2-Ethyl-6-methoxypyridin-3-yl)-7-methoxy-1-methyl-1H-1,3-benzodiazole-5-carbonyl]-2-azabicyclo[2.2.1]heptan-7-amine, I-99, EV-AY8850-002 (EOA13477015) and 5-{5-[(1R,4R,7R)-7-amino-2-azabicyclo[2.2.1]heptane-2-carbonyl]-7-methoxy-1-methyl-1H-1,3-benzodiazol-2-yl}-6-ethylpyridin-2-ol, I-100, EV-AY8850-003 (EOA13477016) were synthesised according to the procedures described in Scheme 6 via synthesis of methyl 2-chloro-6-methoxypyridine-3-carboxylate (EV-AY882703 described in Scheme 6.2.

Scheme 6.2

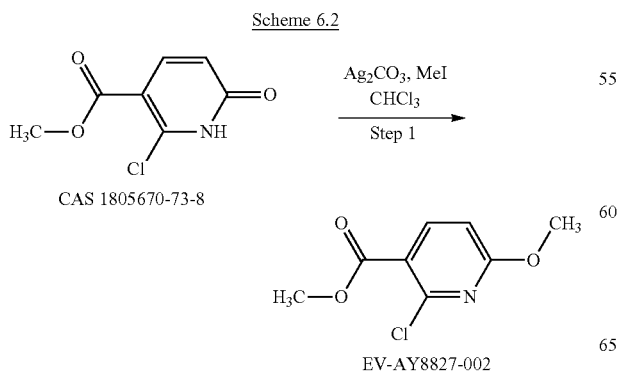

Methyl 2-chloro-6-methoxypyridine-3-carboxylate (EV-AY8827-002)—Step 1

Ag$_2$CO$_3$ (11.0 g, 39.8 mmol) and methyl iodide (3.77 ml, 60.5 mmol) were added to a solution of 2-chloro-6-oxo-1,6-dihydropyridine-3-carboxylic acid (CAS 1805670-73-8, 3.00 g, 17.3 mmol) in chloroform (30 ml) and the resulting mixture was stirred at 50° C. for 3 h. The reaction mixture was filtered under vacuum (washing with chloroform) and the filtrate was concentrated in vacuo. The residue was purified by flash column chromatography (0-100% ethyl acetate/heptane) to afford 2.42 g (69%) of methyl 2-chloro-6-methoxypyridine-3-carboxylate (EV-AY8827-002) as a white powder. LCMS (method D): retention time 1.13 min, M/z=202 (M+1).

I-105

(1R,4R,7R)-2-{2-[2-(Cyclopropylmethyl)pyridin-3-yl]-7-methoxy-1-methyl-1H-1,3-benzodiazole-5-carbonyl}-2-azabicyclo[2.2.1]heptan-7-amine, I-105, EV-AY8871-001 (EOA13478068) was synthesised according to the procedures described in Scheme 6 via synthesis of methyl 2-(cyclopropylmethyl)pyridine-3-carboxylate (EV-AZ9626-002) as described in Scheme 6.3.

Scheme 6.3

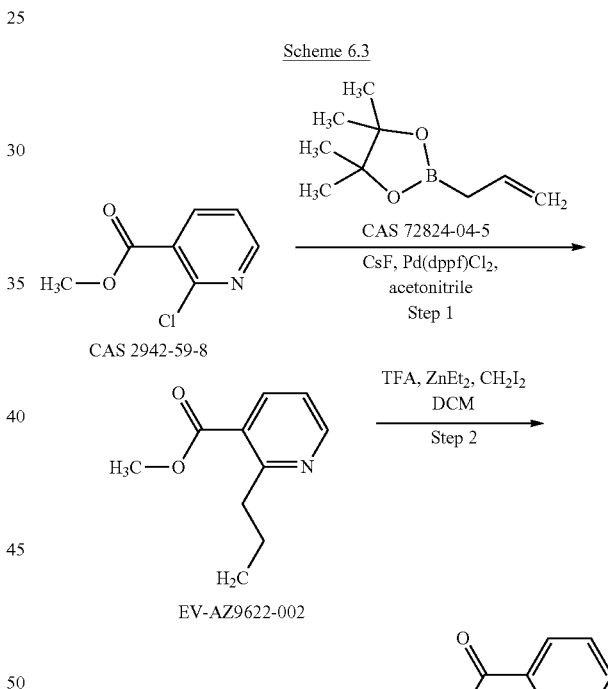

Methyl 2-(prop-2-en-yl)pyridine-3-carboxylate (EV-AZ9622-002)—Step 1

CsF (26.6 g, 174.8 mmol), 4,4,5,5-tetramethyl-2-(prop-2-en-1-yl)-1,3,2-dioxaborolane (CAS 72824-04-5, 22.01 ml, 116.6 mmol) and Pd(dppf)Cl$_2$ (4.26 g, 5.83 mmol) were added to a solution of methyl 2-chloropyridine-3-carboxylate (CAS 2942-59-8, 7.61 ml, 58.3 mmol) in acetonitrile (750 ml) and the resulting mixture was stirred under nitrogen at 70° C. for 1 h. A thick precipitate formed. The reaction mixture was diluted with water (300 ml) and extracted with ethyl acetate (3×500 ml). The combined organic extracts were dried over sodium sulfate, concentrated in vacuo and purified by flash column chromatography (0-80% ethyl acetate/heptane) to obtain 10.31 g (quantitative) of methyl 2-(prop-2-en-1-yl)pyridine-3-carboxylate (EV-AZ9622-002) as a yellow volatile oil. LCMS (method D): retention time 0.88 min, M/z=178 (M+1).

Methyl 2-(cyclopropylmethyl)pyridine-3-carboxylate (EV-AZ9626-002)—Step 2

Trifluoroacetic acid (8.64 ml, 112.9 mmol) in DCM (50 ml) was added dropwise to a solution of 1 M diethylzinc in heptane (112.9 ml) in DCM (150 ml) at 0° C. and the resulting mixture was stirred at 0° C. for 10 minutes. Diiodomethane (9.08 ml, 112.9 mmol) was added to the reaction mixture and stirring at 0° C. was continued for 10 minutes. Methyl 2-(prop-2-en-1-yl)pyridine-3-carboxylate (EV-AZ9622-002, 10 g, 56.4 mmol) in DCM (100 ml) was added dropwise and the resulting mixture was allowed to reach room temperature over a period of 3 h. The reaction was quenched by addition of water (100 ml) and the organic layer was separated. The aqueous mixture was re-extracted with DCM (3×150 ml). The combined organic extracts were dried over sodium sulfate, concentrated in vacuo and purified by flash column chromatography (0-100% ethyl acetate/heptane) to afford 8.26 g (76%) of methyl 2-(cyclopropylmethyl)pyridine-3-carboxylate (EV-AZ9626-002) as a yellow volatile oil. LCMS (method D): retention time 0.88 min, M/z=192 (M+1).

I-117

(1R,4R,7R)-2-{2-[2-(Cyclopropylmethyl)-6-fluoropyridin-3-yl]-7-methoxy-1-methyl-1H-1,3-benzodiazole-5-carbonyl}-2-azabicyclo[2.2.1]heptan-7-amine, 1-117, EV-AZ9647-002 (EOA13694082) was synthesised according to the procedures described in Scheme 6 via synthesis of methyl 2-(cyclopropylmethyl)-6-fluoropyridine-3-carboxylate (EV-AZ9632-002) as described in Scheme 6.4.

Scheme 6.4

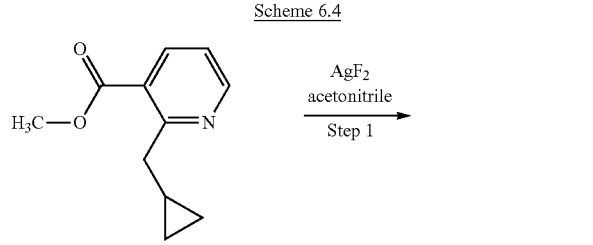

Methyl 2-(cyclopropylmethyl)-6-fluoropyridine-3-carboxylate (EV-AZ9632-002)—Step 1

AgF$_2$ (6.87 g, 47.06 mmol) was added to a solution of methyl 2-(cyclopropylmethyl)pyridine-3-carboxylate (EV-AZ9626-002, synthesised according to Scheme 6.3, 3.00 g, 15.7 mmol) in acetonitrile (25 ml) and the resulting mixture was stirred at room temperature for 16 h. The reaction mixture was filtered under vacuum and the filtrate concentrated in vacuo to afford an orange oil which was purified by flash column chromatography (0-80% ethyl acetate/heptane) to obtain 1.99 g (61%) of methyl 2-(cyclopropylmethyl)-6-fluoropyridine-3-carboxylate (EV-AZ9632-002) as a colourless volatile oil. LCMS (method D): retention time 1.19 min, M/z=210 (M+1).

I-116

(1R,4R,7R)-2-{2-[2-(Cyclopropylmethyl)-6-methoxypyridin-3-yl]-7-methoxy-1-methyl-1H-1,3-benzodiazole-5-carbonyl}-2-azabicyclo[2.2.1]heptan-7-amine, 1-116, EV-AZ9628-002 (EOA13689043) was synthesised according to the procedures described in Scheme 6 via synthesis of 2-(cyclopropylmethyl)-6-methoxypyridine-3-carboxylic acid (EV-AZ9615-002) as described in Scheme 6.5.

Scheme 6.5

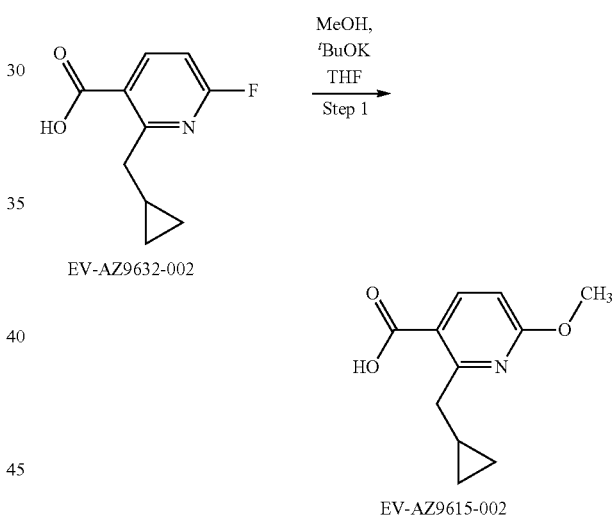

2-(Cyclopropylmethyl)-6-methoxypyridine-3-carboxylic acid (EV-AZ9615-002)—Step 1

Methanol (35 µl, 0.86 mmol) and tBuOK (97 mg, 0.86 mmol) were added to a solution of methyl 2-(cyclopropylmethyl)-6-fluoropyridine-3-carboxylate (EV-AZ9632-00 synthesised according to Scheme 6.4, 150 mg, 0.72 mmol) in THF (2 ml) and the resulting mixture was stirred at room temperature for 2 h. The reaction mixture was diluted with water (20 ml) and acidified to pH 4 using 2M aqueous HCl. The resultant solution was extracted with ethyl acetate (2×50 ml), the combined organic extracts were dried over sodium sulfate and concentrated in vacuo to afford a colourless oil. The residue was dissolved in methanol (5 ml) and 1 M aqueous NaOH (2.15 ml) was added. The mixture was stirred at 60° C. for 3 h, diluted with water (20 ml) and acidified to pH 3 using 2 M aqueous HCl. The resulting solution was extracted with ethyl acetate (2×50 ml), the combined organic extracts were dried over sodium sulfate and concentrated in vacuo to afford 129 mg (82%) of 2-(cyclopropylmethyl)-6-methoxypyridine-3-carboxylic acid (EV-AZ9615-002) as an off-white powder. LCMS (method D): retention time 1.10 min, M/z=208 (M+1).

I-120

(1R,4R,7R)-2-{2-[2-(cyclopropylmethyl)-6-(morpholin-4-yl)pyridin-3-yl]-7-methoxy-1-methyl-1H-1,3-benzodiazole-5-carbonyl}-2-azabicyclo[2.2.1]heptan-7-amine, I-120, EV-AZ9655-001 (EOA13694317) was synthesised according to the procedures described in Scheme 6 via synthesis of methyl 2-[2-(cyclopropylmethyl)-6-(morpholin-4-yl)pyridin-3-yl]-7-methoxy-1-methyl-1H-1,3-benzodiazole-5-carboxylate (EV-AZ9651-002) as described in Scheme 6.6.

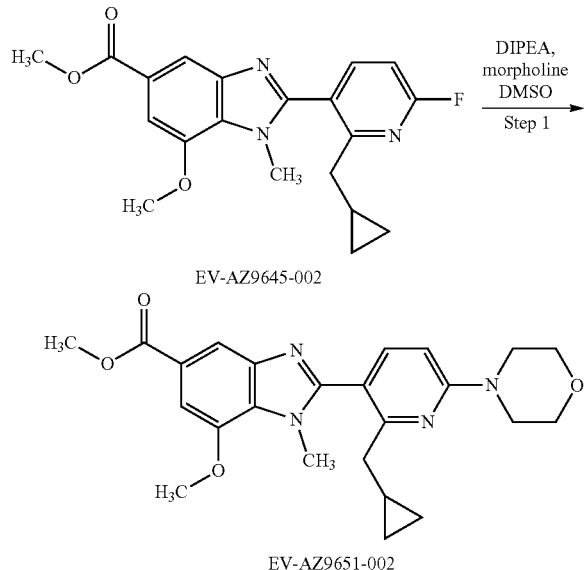

Methyl 2-[2-(cyclopropylmethyl)-6-(morpholin-4-yl)pyridin-3-yl]-7-methoxy-1-methyl-1H-1,3-benzodiazole-5-carboxylate (EV-AZ9651-002)—Step 1

DIPEA (130 µl, 0.73 mmol) and morpholine (63 µl, 0.73 mmol) were added to a stirred solution of methyl 2-[2-(cyclopropylmethyl)-6-fluoropyridin-3-yl]-7-methoxy-1-methyl-1H-1,3-benzodiazole-5-carboxylate (EV-AZ9645-002 synthesised according to Scheme 6.4 and Scheme 1, 90%, 200 mg, 0.49 mmol) in DMSO (2 ml) and the resulting mixture was stirred at 100° C. for 2 h. Acetonitrile (1 ml) was added to the reaction mixture and the resulting solution was purified by prep HPLC (basic method) to afford 161 mg (76%) of methyl 2-[2-(cyclopropylmethyl)-6-(morpholin-4-yl)pyridin-3-yl]-7-methoxy-1-methyl-1H-1,3-benzodiazole-5-carboxylate (EV-AZ9651-002) as an off-white powder. LCMS (method D): retention time 1.15 min, M/z=437 (M+1).

I-121

5-{5-[(1R,4R,7R)-7-Amino-2-azabicyclo[2.2.1]heptane-2-carbonyl]-7-methoxy-1-methyl-1H-1,3-benzodiazol-2-yl}-6-(cyclopropylmethyl)pyridine-2-carbonitrile, I-121, EV-AZ9658-002 (EOA13702812) was synthesised according to the procedures described in Scheme 6 via synthesis of tert-butyl N-[(1R,4R,7R)-2-{2-[6-cyano-2-(cyclopropylmethyl)pyridin-3-yl]-7-methoxy-1-methyl-1H-1,3-benzodiazole-5-carbonyl}-2-azabicyclo[2.2.1]heptan-7-yl]carbamate (EV-AZ9657-002) as described in Scheme 6.7.

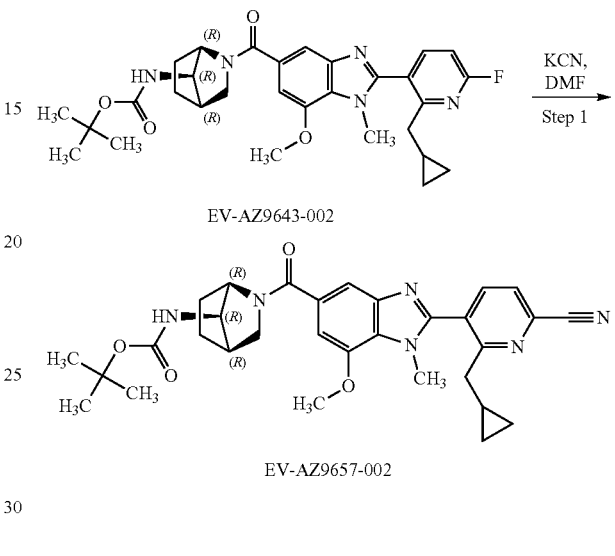

Tert-butyl N-[(1R,4R,7R)-2-{2-[6-cyano-2-(cyclopropylmethyl)pyridin-3-yl]-7-methoxy-1-methyl-1H-1,3-benzodiazole-5-carbonyl}-2-azabicyclo[2.2.1]heptan-7-yl]carbamate (EV-AZ9657-002)—Step 1

KCN (38 mg, 0.58 mmol) was added to a solution of tert-butyl N-[(1R,4R,7R)-2-{2-[2-(cyclopropylmethyl)-6-fluoropyridin-3-yl]-7-methoxy-1-methyl-1H-1,3-benzodiazole-5-carbonyl}-2-azabicyclo[2.2.1]heptan-7-yl]carbamate (EV-AZ9643-002 synthesised according to Scheme 6.5 and Scheme 1, 80 mg, 0.15 mmol) in DMF (2 ml) and the resulting mixture was stirred at 120° C. for 16 h. The reaction mixture was diluted with ethyl acetate (50 ml) and washed with water (2×25 ml). The combined organic extracts were dried over sodium sulfate and concentrated in vacuo to afford a yellow oil. The residue was purified by prep HPLC (basic method) to afford 58 mg (72%) of tert-butyl N-[(1R,4R,7R)-2-{2-[6-cyano-2-(cyclopropylmethyl)pyridin-3-yl]-7-methoxy-1-methyl-1H-1,3-benzodiazole-5-carbonyl}-2-azabicyclo[2.2.1]heptan-7-yl]carbamate (EV-AZ9657-002) as an off-white powder. LCMS (method D): retention time 1.22 min, M/z=557 (M+1).

I-114

2-[(3-{5-[(1R,4R,7R)-7-Amino-2-azabicyclo[2.2.1]heptane-2-carbonyl]-7-methoxy-1-methyl-1H-1,3-benzodiazol-2-yl}pyridin-2-yl)methyl]cyclopropane-1-carboxylic acid, I-114, EV-AZ9624-001 (EOA13669062) was synthesised according to the procedures described in Scheme 6 via synthesis of methyl 2-({2-[(tert-butoxy)carbonyl]cyclopropyl}methyl)pyridine-3-carboxylate (EV-AZ9605-002) described in Scheme 6.8.

Scheme 6.8

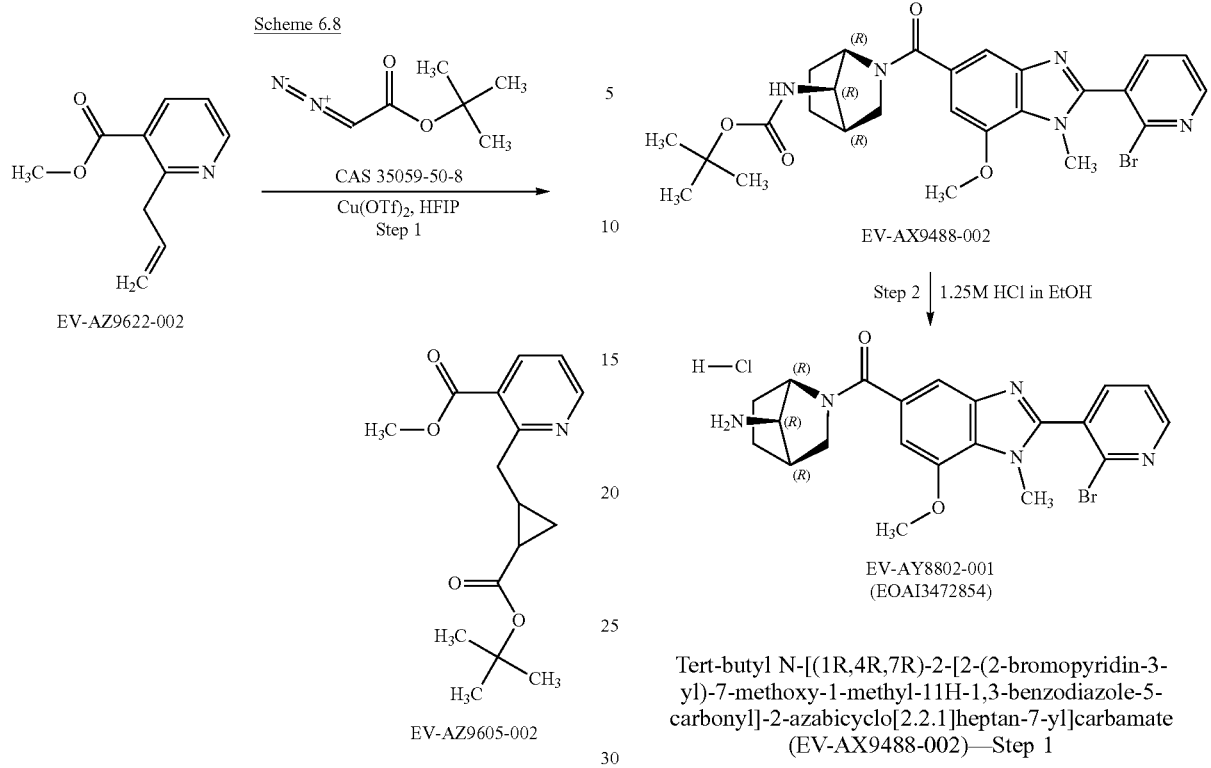

Methyl 2-({2-[(tert-butoxy)carbonyl]cyclopropyl}methyl)pyridine-3-carboxylate (EV-AZ9605-002)—Step 1

Cu(OTf)$_2$ (0.18 g, 0.51 mmol) and tert-butyl diazoacetate (CAS 35059-50-8, 1.95 ml, 12.7 mmol) were added to a solution of methyl 2-(prop-2-en-1-yl)pyridine-3-carboxylate (EV-AZ9622-002 synthesised according to Scheme 6.3, step 1, 90%, 1.00 g, 5.08 mmol) in HfIP (10 ml) at 0° C. and the resulting mixture was stirred at room temperature for 2 h. The reaction mixture was quenched with saturated aqueous ammonium chloride (50 ml) and extracted with DCM (2×100 ml). The combined organic extracts were dried over sodium sulfate, concentrated in vacuo and purified by flash column chromatography (0-80% ethyl acetate/heptane) to afford 1.23 g (81%) of methyl 2-({2-[(tert-butoxy)carbonyl]cyclopropyl}methyl)pyridine-3-carboxylate (EV-AZ9605-002) as a pale yellow oil. LCMS (method D): retention time 1.20 min, M/z=292 (M+1).

Scheme 7

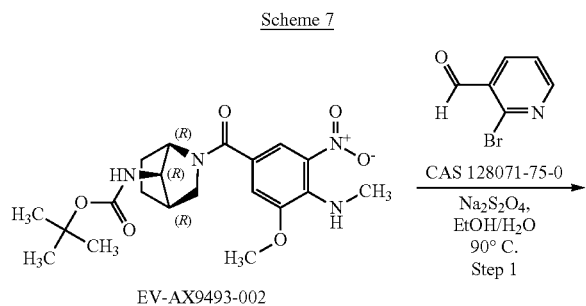

Tert-butyl N-[(1R,4R,7R)-2-[2-(2-bromopyridin-3-yl)-7-methoxy-1-methyl-1lH-1,3-benzodiazole-5-carbonyl]-2-azabicyclo[2.2.1]heptan-7-yl]carbamate (EV-AX9488-002)—Step 1

2-Bromopyridine-3-carbaldehyde (CAS 128071-75-0, 310 mg, 1.67 mmol) and Na$_2$S$_2$O$_4$ (85%, 932 mg, 4.55 mmol) were added to a solution of tert-butyl N-[(1R,4R,7R)-2-[3-methoxy-4-(methylamino)-5-nitrobenzoyl]-2-azabicyclo[2.2.1]heptan-7-yl]carbamate (EV-AX9493-002 synthesised as in Scheme 5, 85%, 750 mg, 1.52 mmol) in ethanol (5 ml) and water (3 ml) and the resulting mixture was stirred at 90° C. for 4 h. The reaction mixture was filtered under vacuum and the filtrate concentrated in vacuo. The resulting residue was purified by prep HPLC (basic method) to obtain 360 mg (43%) of tert-butyl N-[(1R,4R,7R)-2-[2-(2-bromopyridin-3-yl)-7-methoxy-1l-methyl-1H-1,3-benzodiazole-5-carbonyl]-2-azabicyclo[2.2.1]heptan-7-yl]carbamate (EV-AX9488-002) as an off-white powder. LCMS (method D): retention time 1.13 min, M/z=556, 558 (M+1).

(1R,4R,7R)-2-[2-(2-Bromopyridin-3-yl)-7-methoxy-1-methyl-1H-1,3-benzodiazole-5-carbonyl]-2-azabicyclo[2.2.1]heptan-7-amine hydrochloride, I-90, (EV-AY8802-001)—Step 2

1.25M HCl in ethanol (2 ml) was added to a solution of tert-butyl N-[(1R,4R,7R)-2-[2-(2-bromopyridin-3-yl)-7-methoxy-1l-methyl-1H-1,3-benzodiazole-5-carbonyl]-2-azabicyclo[2.2.1]heptan-7-yl]carbamate (EV-AX9488-002, 105 mg, 0.19 mmol) in ethanol (4 ml) and the resulting mixture was stirred at 5° C. for 5 h. The reaction mixture was concentrated in vacuo to afford a white powder. The compound was taken up in methanol (10 ml) and treated with Smopex-105 (CAS 527751-99-1) metal scavenger (105 mg) and stirred at room temperature for 2 h. The fibres were removed by vacuum filtration and the filtrate concentrated in vacuo to afford 93 mg (quantitative) of (1R,4R,7R)-2-[2-(2-bromopyridin-3-yl)-7-methoxy-1-methyl-H-1,3-benzodiazole-5-carbonyl]-2-azabicyclo[2.2.1]heptan-7-amine hydrochloride, I-90, (EV-AY8802-001) as a white powder. LCMS (method H): retention time 2.14 min, M/z=457 (M+1).

The following compounds were synthesized according to the procedures described above:

| Compound# | Mol Wt | LCMS $T_{ret}$ | M/Z(+) | LCMS Method | Salt | Salt Stoichiometry |
|---|---|---|---|---|---|---|
| I-1 | 352.433 | 1.18 min | 353.3 | A | N/A | N/A |
| I-2 | 428.529 | 3.84 min | 429.3 | B | HCl | 1 |
| I-3 | 454.566 | 4.07 min | 455.4 | B | HCl | 1 |
| I-4 | 418.534 | 1.76 min | 419.3 | A | HCl | 1 |
| I-5 | 420.550 | 1.86 min | 421.3 | A | HCl | 1 |
| I-6 | 418.534 | 1.80 min | 419.3 | A | HCl | 1 |
| I-7 | 418.534 | 1.74 min | 419.3 | A | HCl | 1 |
| I-8 | 457.367 | 1.78 min | 459.1 | A | N/A | N/A |
| I-9 | 453.578 | 2.17 min | 454.2 | A | HCl | 1 |
| I-10 | 479.615 | 2.20 min | 480.2 | A | N/A | N/A |
| I-11 | 479.615 | 2.21 min | 480.2 | A | N/A | N/A |
| I-12 | 454.566 | 1.68 min | 455.2 | A | HCl | 1 |
| I-13 | 454.566 | 2.06 min | 455.1 | A | HCl | 1 |
| I-14 | 471.569 | 2.20 min | 472.2 | A | HCl | 1 |
| I-15 | 471.569 | 2.22 min | 472.2 | A | HCl | 1 |
| I-16 | 481.512 | 2.36 min | 482.1 | A | HCl | 1 |
| I-17 | 454.566 | 1.39 min | 455.2 | A | HCl | 1 |
| I-18 | 454.556 | 1.16 min | 455.2 | A | HCl | 1 |
| I-19 | 511.538 | 2.53 min | 512.1 | A | HCl | 1 |
| I-20 | 456.379 | 2.02 min | 456.1 | A | HCl | 1 |
| I-21 | 377.482 | 1.46 min | 378.2 | A | HCl | 1 |
| I-22 | 454.566 | 1.60 min | 455.2 | A | HCl | 1 |
| I-23 | 454.566 | 1.33 min | 455.2 | A | HCl | 1 |
| I-24 | 429.517 | 1.31 min | 430.2 | A | HCl | 1 |
| I-25 | 443.544 | 1.48 min | 444.3 | A | HCl | 1 |
| I-26 | 440.540 | 1.40 min | 441.2 | A | HCl | 1 |
| I-27 | 454.566 | 1.54 min | 455.2 | A | HCl | 1 |
| I-28 | 484.592 | 1.90 min | 485.2 | A | HCl | 1 |
| I-29 | 467.605 | 2.23 min | 468.2 | A | HCl | 1 |
| I-30 | 479.615 | 2.47 min | 480.2 | A | HCl | 1 |
| I-31 | 392.497 | 3.17 min | 393.3 | B | HCl | 1 |
| I-32 | 481.631 | 2.48 min | 482.3 | A | HCl | 1 |
| I-33 | 454.566 | 2.37 min | 455.2 | A | HCl | 1 |
| I-34 | 442.556 | 1.68 min | 443.3 | A | Formic acid | 1 |
| I-35 | 378.470 | 3.19 min | 379.3 | B | HCl | 1 |
| I-36 | 468.593 | 1.23 min | 469.2 | A | HCl | 1 |
| I-37 | 497.631 | 2.43 min | 498.2 | A | HCl | 1 |
| I-38 | 485.595 | 2.29 min | 486.2 | A | HCl | 1 |
| I-39 | 468.593 | 2.43 min | 469.2 | A | HCl | 1 |
| I-40 | 489.012 | 1.71 min | 489.2 | A | HCl | 1 |
| I-41 | 468.593 | 1.34 min | 469.2 | A | HCl | 1 |
| I-42 | 482.619 | 1.40 min | 483.3 | A | HCl | 1 |
| I-43 | 616.751 | 2.79 min | 617.3 | A | HCl | 1 |
| I-44 | 480.604 | 1.42 min | 481.2 | A | HCl | 1 |
| I-45 | 468.593 | 1.45 min | 469.3 | A | HCl | 1 |
| I-46 | 484.592 | 1.49 min | 485.3 | A | HCl | 1 |
| I-47 | 383.51 | 1.32 min | 384.2 | A | HCl | 1 |
| I-48 | 526.629 | 2.30 min | 527.2 | A | HCl | 1 |
| I-49 | 393.482 | 1.17 min | 394.3 | A | HCl | 1 |
| I-50 | 446.544 | 2.21 min | 447.3 | A | HCl | 1 |
| I-51 | 491.608 | 3.46 min | 492.3 | H | HCl | 1 |
| I-52 | 498.619 | 2.04 min | 499.3 | A | N/A | N/A |
| I-53 | 478.586 | 1.70 min | 479.4 | A | HCl | 1 |
| I-54 | 514.618 | 1.90 min | 515.3 | A | HCl | 1 |
| I-55 | 468.550 | 2.19 min | 469.2 | A | HCl | 1 |
| I-56 | 486.565 | 1.62 min | 487.2 | A | HCl | 1 |
| I-57 | 429.514 | 1.74 min | 430.2 | A | HCl | 1 |
| I-58 | 458.555 | 1.44 min | 459.2 | A | HCl | 1 |
| I-59 | 400.476 | 2.04 min | 401.2 | A | HCl | 1 |
| I-60 | 496.603 | 1.78 min | 497.3 | A | HCl | 2 |
| I-61 | 510.630 | 1.99 min | 511.3 | A | HCl | 2 |
| I-62 | 432.518 | 2.96 min | 433.3 | H | HCl | 1 |
| I-63 | 476.571 | 1.85 min | 477.3 | A | HCl | 1 |
| I-64 | 485.581 | 1.68 min | 486.2 | A | HCl | 1 |
| I-65 | 496.603 | 1.47 min | 497.3 | A | HCl | 1 |
| I-66 | 497.591 | 1.64 min | 198.3 | A | HCl | 1 |
| I-67 | 498.619 | 1.60 min | 499.3 | A | HCl | 1 |
| I-68 | 498.619 | 1.60 min | 499.3 | A | HCl | 1 |
| I-69 | 446.545 | 2.09 min | 447.2 | A | HCl | 1 |
| I-70 | 444.529 | 2.01 min | 445.3 | A | HCl | 1 |
| I-71 | 500.595 | 1.17 min | 501.3 | A | HCl | 1 |
| I-72 | 488.585 | 1.20 min | 489.3 | A | HCl | 1 |
| I-73 | 542.672 | 2.27 min | 543.2 | A | HCl | 1 |
| I-74 | 480.561 | 3.01 min | 481.3 | H | HCl | 1 |
| I-75 | 494.588 | 2.27 min | 495.2 | A | HCl | 1 |
| I-76 | 502.608 | 2.00 min | 503.2 | A | HCl | 1 |
| I-77 | 495.576 | 2.44 min | 496.2 | C | HCl | 2 |
| I-78 | 530.636 | 2.28 min | 531.3 | A | HCl | 1 |
| I-79 | 484.553 | 1.71 min | 485.4 | A | N/A | N/A |
| I-80 | 481.549 | 1.49 min | 482.2 | A | HCl | 1 |
| I-81 | 430.502 | 1.73 min | 431.3 | A | HCl | 1 |
| I-82 | 472.463 | 1.99 min | 473.2 | A | HCl | 1 |
| I-83 | 486.490 | 2.15 min | 487.2 | A | HCl | 1 |
| I-84 | 508.614 | 2.39 min | 509.3 | A | HCl | 1 |
| I-85 | 508.614 | 2.37 min | 509.3 | A | HCl | 1 |
| I-86 | 510.630 | 1.63 min | 511.3 | A | HCl | 1 |
| I-87 | 484.568 | 1.51 min | 485.3 | A | HCl | 1 |
| I-88 | 407.466 | 1.71 min | 408.3 | A | N/A | N/A |
| I-89 | 502.608 | 2.08 min | 503.3 | A | HCl | 1 |
| I-90 | 456.336 | 2.14 min | 457.2 | H | HCl | 1 |
| I-91 | 447.530 | 2.03 min | 448.3 | A | N/A | N/A |
| I-92 | 547.668 | 2.17 min | 548.3 | A | N/A | N/A |
| I-93 | 506.598 | 2.31 min | 507.4 | A | N/A | N/A |
| I-94 | 535.639 | 2.14 min | 536.4 | A | N/A | N/A |
| I-95 | 535.639 | 2.12 min | 536.4 | A | N/A | N/A |
| I-96 | 405.493 | 2.14 min | 406.3 | H | HCl | 1 |
| I-97 | 483.605 | 3.36 min | 484.4 | H | N/A | N/A |
| I-98 | 573.727 | 4.26 min | 574.5 | H | N/A | N/A |
| I-99 | 435.519 | 1.63 min | 436.3 | C | N/A | N/A |
| I-100 | 421.492 | 1.75 min | 422.3 | H | N/A | N/A |
| I-101 | 423.483 | 2.36 min | 424.3 | H | HCl | 1 |
| I-102 | 447.530 | 2.08 min | 448.4 | H | N/A | N/A |
| I-103 | 435.519 | 1.35 min | 436.3 | A | HCl | 1 |
| I-104 | 419.519 | 1.35 min | 420.4 | A | HCl | 1 |
| I-105 | 431.530 | 1.31 min | 432.2 | A | HCl | 1 |
| I-106 | 483.605 | 1.76 min | 484.4 | A | N/A | N/A |
| I-107 | 422.480 | 1.99 min | 423.3 | H | HCl | 1 |
| I-108 | 445.557 | 2.51 min | 446.4 | H | HCl | 1 |
| I-109 | 448.561 | 1.03 min | 449.4 | A | Trifluoroacetic acid | 1 |
| I-110 | 445.557 | 1.48 min | 446.4 | C | HCl | 1 |
| I-111 | 526.426 | 2.44 min | 528.3 | H | N/A | N/A |
| I-112 | 461.556 | 2.28 min | 462.4 | H | N/A | N/A |
| I-113 | 478.587 | 2.12 min | 479.2 | C | N/A | N/A |
| I-114 | 475.540 | 1.13 min / 1.21 min | 476.4 | H | HCl | 1 |
| I-115 | 445.557 | 1.21 min | 446.3 | A | HCl | 1 |
| I-116 | 461.556 | 1.79 min | 462.2 | A | N/A | N/A |
| I-117 | 449.521 | 1.71 min | 450.3 | A | N/A | N/A |
| I-118 | 405.493 | 1.15 min | 406.3 | A | N/A | N/A |
| I-119 | 405.493 | 1.17 min | 406.2 | A | HCl | 1 |
| I-120 | 516.635 | 1.70 min | 517.3 | A | HCl | 1 |
| I-121 | 456.540 | 1.82 min | 457.3 | A | N/A | N/A |
| I-122 | 405.493 | 1.45 min | 406.2 | A | N/A | N/A |

Biological Assays

Compounds of the present invention were assayed as inhibitors of PAD4 using the assay protocol described below.

Compounds were solubilised in 100% DMSO to achieve 100 mM final compound concentration. Compound stock solutions were stored at RT. A series of dilutions were prepared in DMSO and mixed 8 times with 20 μL mixing volume. Final assay conditions were as follows:

Reaction volume: 20 μl

Assay buffer (as aforementioned): 100 mM Tris-HCl (pH 7.6), 2 mM DTT, 1 mM $CaCl_2$)

Final concentrations:
 –100 nM hPAD4 enzyme
 –50 μM (8-fold sub-$K_m$) substrate peptide
 –0.5% DMSO Total incubation time: 65 mins at 37° C.

Stop solution: 40 μl 5% TCA in ACN 0.25 μL of compound solution was added to 10 μL of 200 nM PAD4 in assay buffer (100 mM Tris-HCl pH 7.6, 2 mM DTT). After 5 mins, 10 μL of 100 μM of substrate in buffer (100 mM Tris-HCl pH 7.6, 2 mM DTT, 2 mM CaCl2)) was added and the reaction incubated for 60 mins at 37° C. The enzymatic reaction was quenched by addition of 40 μl of 5% TCA in ACN (1.7% TCA final concentration) stop solution. Arginine containing substrate and citrulline containing product (+1 Da mass shift) were subjected to solid phase extraction on Agilent RapidFire (RF) 300 system and detected on a coupled, triple quadrupole Agilent 6460 QQQ mass spectrometry (MS) device under application of multiple reaction monitoring (MRM) for quantitation.

Table 2, below, shows the activity of selected compounds of this invention in the PAD4 assays described above. The compound numbers correspond to the compound numbers in Table 1. Compounds having an activity designated as "A" provided an $IC_{50}$ 1 M; compounds having an activity designated as "B" provided an $IC_{50}$ of 1.0-5.0 μM; compounds having an activity designated as "C" provided an $IC_{50}$ of 5.0-10.0 μM; and compounds having an activity designated as "D" provided an $IC_{50}$ of ≥10.0 μM. The term pIC50=−log(IC50). Compounds having an activity designated as "E" provided a pIC50<4; compounds having an activity designated as "F" provided a pIC50 of 4.0-5.0; compounds having an activity designated as "G" provided a pIC50 of 5.0-6.0; and compounds having an activity designated as "H" provided a pIC50>6. "NA" stands for "not assayed."

TABLE 2

PAD4 Activity

| Compound # | hPAD4 AR $IC_{50}$ μM | hPAD4 AR $pIC_{50}$ μM | hPAD4 RFMS $IC_{50}$ μM | hPAD4 RFMS $pIC_{50}$ | mPAD4 RFMS $IC_{50}$ μM | mPAD4 RFMS $pIC_{50}$ |
|---|---|---|---|---|---|---|
| I-1 | NA | NA | D | F | NA | NA |
| I-2 | NA | NA | D | F | NA | NA |
| I-3 | NA | NA | D | F | NA | NA |
| I-4 | NA | NA | D | F | NA | NA |
| I-5 | NA | NA | D | F | NA | NA |
| I-6 | NA | NA | D | F | NA | NA |
| I-7 | NA | NA | D | E | NA | NA |
| I-8 | NA | NA | D | F | NA | NA |
| I-9 | NA | NA | A | H | C | G |
| I-10 | NA | NA | D | F | NA | NA |
| I-11 | NA | NA | B | G | D | F |
| I-12 | NA | NA | B | G | D | F |
| I-13 | NA | NA | D | E | NA | NA |
| I-14 | NA | NA | D | F | NA | NA |
| I-15 | NA | NA | D | F | NA | NA |
| I-16 | NA | NA | C | G | NA | NA |
| I-17 | NA | NA | C | G | D | F |
| I-18 | NA | NA | B | G | D | F |
| I-19 | NA | NA | C | G | B | G |
| I-20 | NA | NA | A | H | C | G |
| I-21 | NA | NA | C | G | D | F |
| I-22 | NA | NA | D | E | NA | NA |
| I-23 | NA | NA | C | G | D | F |
| I-24 | NA | NA | D | F | NA | NA |
| I-25 | NA | NA | D | F | NA | NA |
| I-26 | NA | NA | D | F | NA | NA |
| I-27 | NA | NA | D | F | NA | NA |
| I-28 | NA | NA | A | H | B | G |
| I-29 | NA | NA | B | G | D | F |
| I-30 | NA | NA | A | H | B | G |
| I-31 | NA | NA | D | E | NA | NA |
| I-32 | NA | NA | B | G | C | G |
| I-33 | NA | NA | C | G | NA | NA |
| I-34 | NA | NA | D | F | NA | NA |
| I-35 | NA | NA | D | F | D | E |
| I-36 | NA | NA | D | E | D | E |
| I-37 | NA | NA | A | H | B | G |
| I-38 | NA | NA | B | G | B | G |
| I-39 | NA | NA | B | G | B | G |
| I-40 | NA | NA | C | G | D | F |
| I-41 | NA | NA | C | G | D | F |
| I-42 | NA | NA | D | F | D | F |
| I-43 | B | G | A | H | A | H |
| I-44 | NA | NA | D | F | D | E |
| I-45 | NA | NA | B | G | D | F |
| I-46 | A | H | A | H | C | G |
| I-47 | NA | NA | D | F | D | E |
| I-48 | NA | NA | B | G | A | H |
| I-49 | NA | NA | D | F | D | F |
| I-50 | NA | NA | B | G | B | G |
| I-51 | D | E | D | E | D | E |
| I-52 | D | E/F | D | E | D | E |
| I-53 | NA | NA | D | F | D | F |
| I-54 | NA | NA | D | F | D | F |
| I-55 | NA | NA | C | G | B | G |
| I-56 | NA | NA | D | F | D | F |
| I-57 | NA | NA | D | F | D | F |
| I-58 | NA | NA | D | E | D | E |
| I-59 | NA | NA | D | F | NA | NA |
| I-60 | D | E/F | D | F | D | F |
| I-61 | D | F | D | F | D | F |
| I-62 | A | H | B | G | B | G |
| I-63 | B | G | D | F | D | F |
| I-64 | A | H | B | G | NA | NA |
| I-65 | A | H | A | H | NA | NA |
| I-66 | NA | NA | B | G | B | G |
| I-67 | NA | NA | B | G | C | G |
| I-68 | NA | NA | B | G | B | G |
| I-69 | A | H | A | H | B | G |
| I-70 | A | H | A | H | B | G |
| I-71 | A | H | B | G | B | G |
| I-72 | NA | NA | B | G | C | G |
| I-73 | A | H | B | G | B | G |
| I-74 | B | G | B | G | C | G |
| I-75 | B | G | B | G | D | F |
| I-76 | B | G | C | G | D | F |
| I-77 | C | G | D | F | D | F |
| I-78 | A | H | B | G | B | G |
| I-79 | B | G | B | G | D | F |
| I-80 | B | G | C | G | D | F |
| I-81 | A | H | NA | NA | NA | NA |
| I-82 | A | H | NA | NA | NA | NA |
| I-83 | B | G | NA | NA | NA | NA |
| I-84 | A | H | NA | NA | NA | NA |
| I-85 | A | H | NA | NA | NA | NA |
| I-86 | A | H | NA | NA | NA | NA |
| I-87 | A | H | NA | NA | NA | NA |
| I-88 | D | F | NA | NA | NA | NA |
| I-89 | A | H | NA | NA | NA | NA |
| I-90 | C/D | F/G | NA | NA | NA | NA |
| I-91 | C/D | F/G | NA | NA | NA | NA |
| I-92 | A | H | NA | NA | NA | NA |
| I-93 | C | G | NA | NA | NA | NA |
| I-94 | C/D | F/G | NA | NA | NA | NA |
| I-95 | C/D | F/G | NA | NA | NA | NA |
| I-96 | B | G | NA | NA | NA | NA |
| I-97 | B | G | NA | NA | NA | NA |
| I-98 | C/D | F/G | NA | NA | NA | NA |
| I-99 | B | G | NA | NA | NA | NA |
| I-101 | C/D | F/G | NA | NA | NA | NA |
| I-102 | A | H | NA | NA | NA | NA |
| I-103 | C/D | F/G | NA | NA | NA | NA |
| I-104 | C/D | F/G | NA | NA | NA | NA |
| I-105 | A | H | NA | NA | NA | NA |
| I-106 | B | G | NA | NA | NA | NA |
| I-107 | C/D | F/G | NA | NA | NA | NA |
| I-108 | A | H | NA | NA | NA | NA |
| I-109 | B | G | NA | NA | NA | NA |
| I-111 | A | H | NA | NA | NA | NA |
| I-112 | A | H | NA | NA | NA | NA |
| I-113 | B | G | NA | NA | NA | NA |

TABLE 2-continued

| | PAD4 Activity | | | | | |
|---|---|---|---|---|---|---|
| Compound # | hPAD4 AR IC$_{50}$ μM | hPAD4 AR pIC$_{50}$ μM | hPAD4 RFMS IC$_{50}$ μM | hPAD4 RFMS pIC$_{50}$ | mPAD4 RFMS IC$_{50}$ μM | mPAD4 RFMS pIC$_{50}$ |
| I-114 | C/D | F/G | NA | NA | NA | NA |
| I-115 | A | H | NA | NA | NA | NA |
| I-117 | A | H | NA | NA | NA | NA |
| I-118 | B | G | NA | NA | NA | NA |

We claim:

1. A compound of formula I':

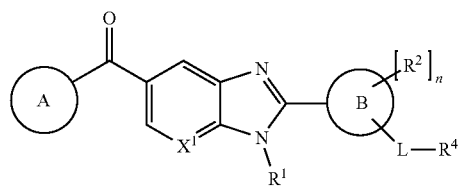

or a pharmaceutically acceptable salt thereof, wherein:
Ring A is

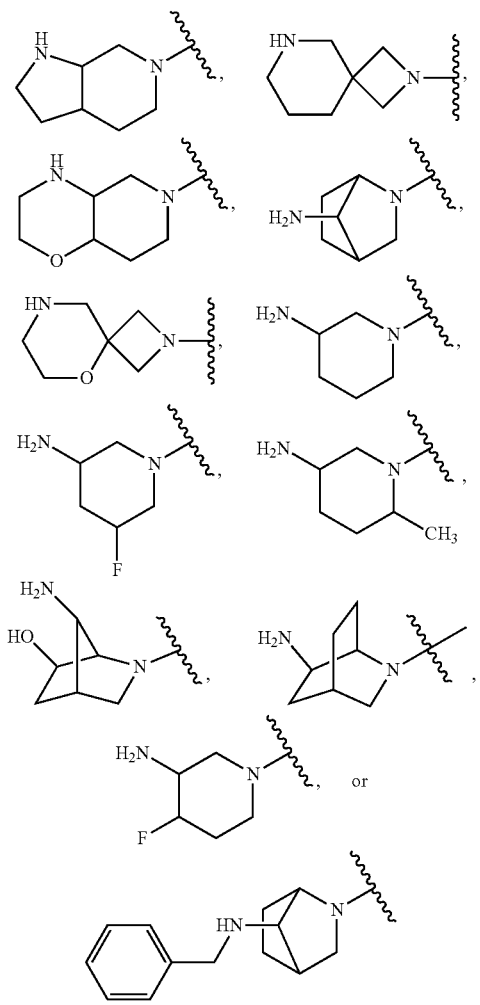

wherein Ring A is optionally substituted with 1-4 groups selected from fluorine, —CN, —OR, or C$_{1-6}$ aliphatic optionally substituted with 1-3 fluorine atoms;

Ring B is a 6-membered heteroaryl ring having 1-3 heteroatoms independently selected from nitrogen, oxygen, or sulfur;

R$^1$ is hydrogen, -Cy, or C$_{1-6}$ aliphatic optionally substituted with -Cy and optionally further substituted with 1-4 groups selected from fluorine, —CN, or —OR;

each -Cy is independently a 6-membered aryl ring containing 0-2 nitrogen atoms, or a 4-7 membered saturated monocyclic ring having 0-2 heteroatoms independently selected from nitrogen, oxygen, or sulphur, wherein -Cy is optionally substituted with 1-4 groups selected from fluorine, —CN, or —OR;

R$^2$ is hydrogen, —CN, —OR, -Cy, or C$_{1-10}$ aliphatic optionally substituted with -Cy and optionally further substituted with 1-5 groups selected from fluorine, —CN, or —OR; or:

two R$^2$ groups on the same carbon are optionally taken together to form =O;

n is 1, 2, or 3;

X$^1$ is N or C(R$^3$);

R$^3$ is —R, halogen, or —OR;

each R is independently hydrogen or C$_{1-6}$ aliphatic optionally substituted with 1-3 fluorine atoms;

L is selected from a covalent bond or a C$_{1-6}$ membered straight or branched, saturated or unsaturated hydrocarbon chain wherein one methylene unit of L is optionally replaced by —S(O)$_2$— or —C(O)N(R$^y$)-, wherein R$^y$ is R or —CH$_2$phenyl; and R$^4$ is halogen, R, phenyl, or a 5-6-membered heteroaryl ring having 1-3 heteroatoms independently selected from nitrogen, oxygen, or sulphur, wherein R$^4$ is optionally substituted with 1-4 groups independently selected from halogen, —CN, —OR, —C(O)OH, or C$_{1-6}$ aliphatic optionally substituted with 1-3 fluorine atoms.

2. The compound according to claim 1, wherein said compound is of formula I'-a:

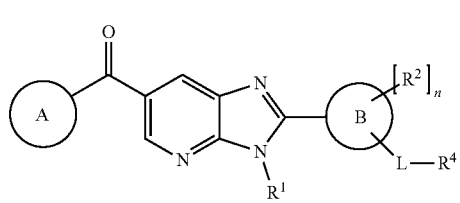

or a pharmaceutically acceptable salt thereof.

3. The compound according to claim 1, wherein said compound is of formula I'-b:

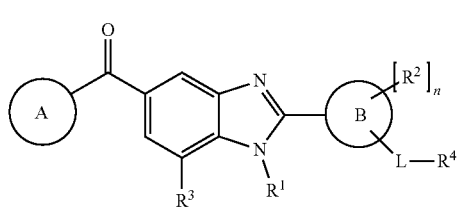

or a pharmaceutically acceptable salt thereof.

4. The compound according to claim 3, wherein Ring A is

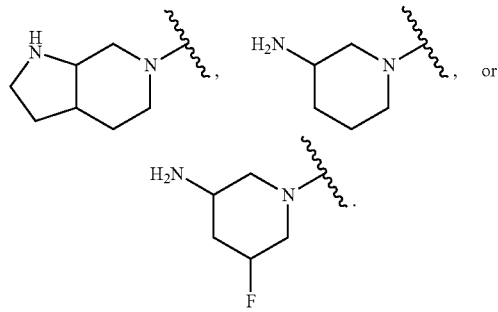

5. The compound according to claim 4, wherein Ring A is

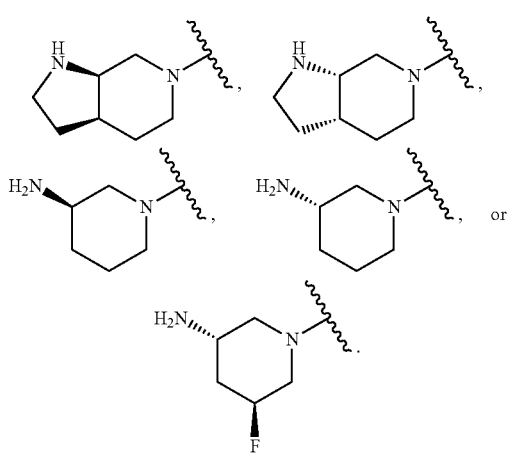

6. The compound according to claim 3, wherein Ring B is a 6-membered heteroaryl ring having 1-2 nitrogens.

7. The compound according to claim 6, wherein Ring B is pyridyl.

8. The compound according to claim 3, wherein $R^4$ is phenyl or pyridyl.

9. The compound according to claim 1, wherein said compound is selected from

I-49

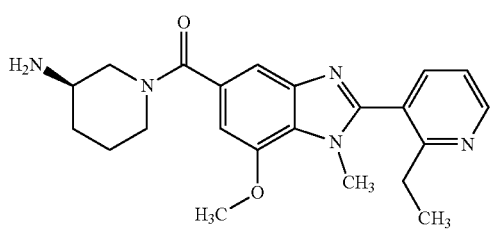

I-88

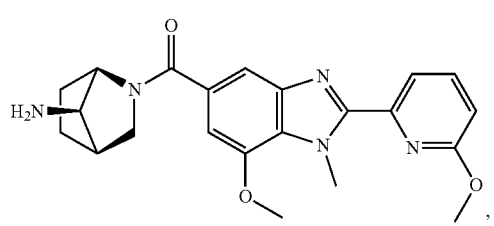

-continued

I-90

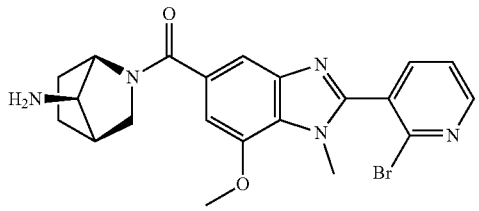

I-91

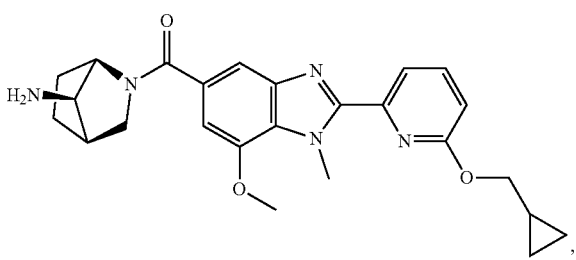

I-96

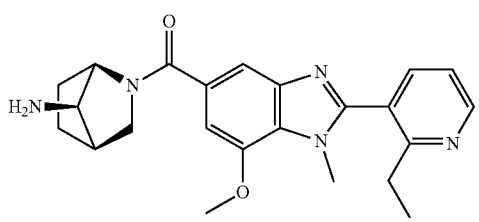

I-99

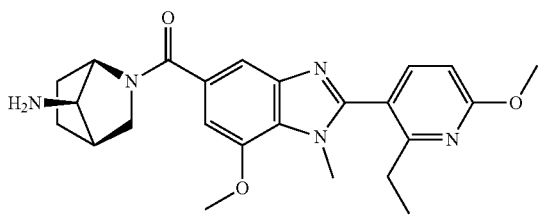

I-100

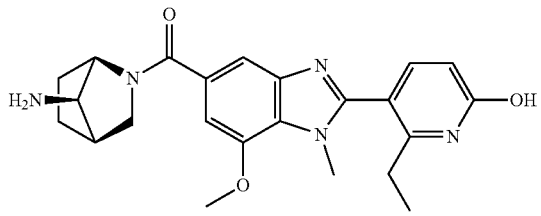

I-101

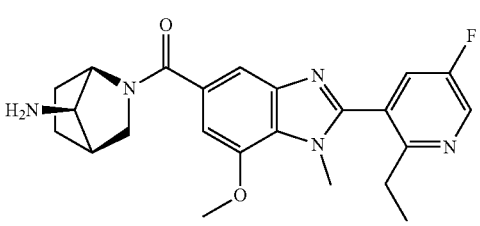

-continued
I-102
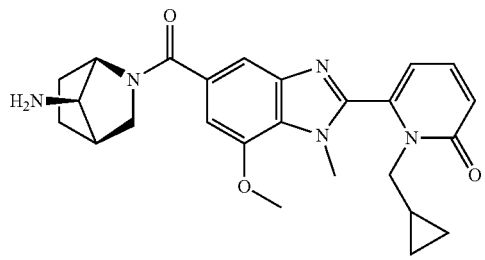
I-103
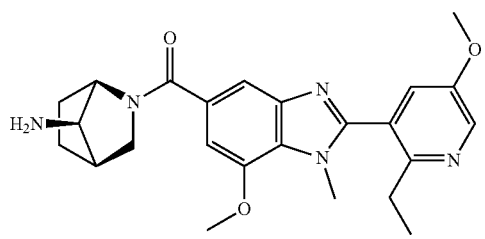
I-104
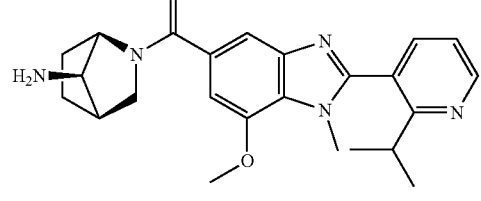
I-105
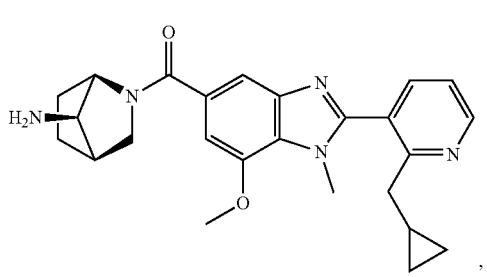
I-107
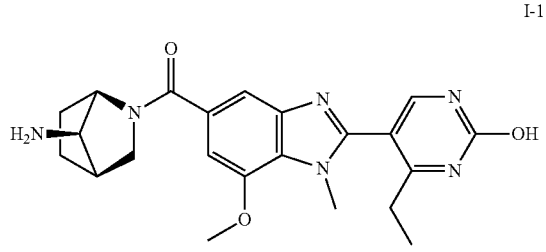
I-108
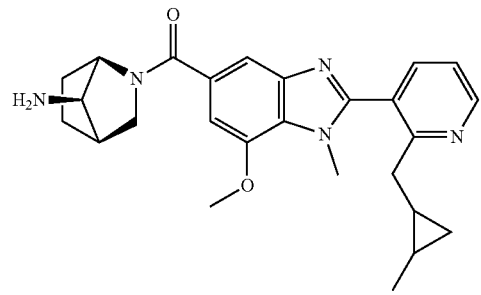
-continued
I-110
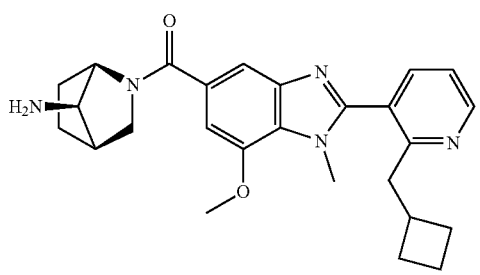
I-111
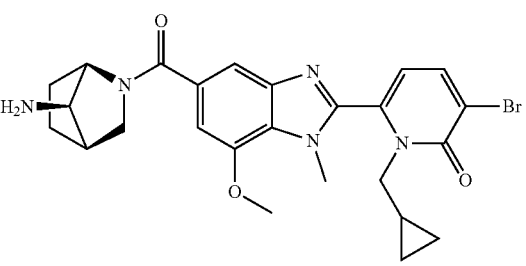
I-112
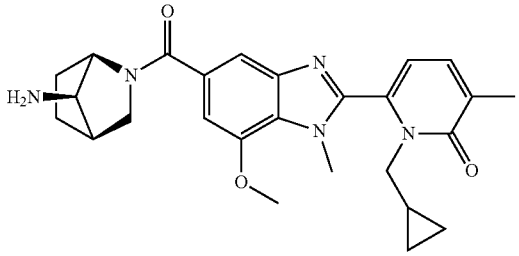
I-114
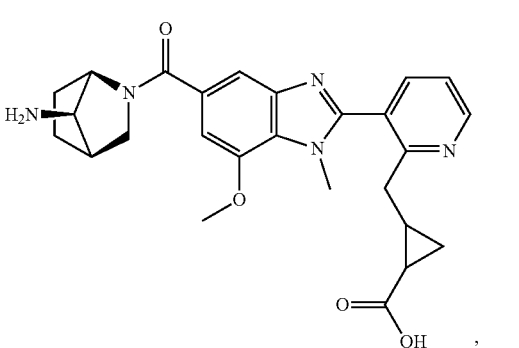
I-115
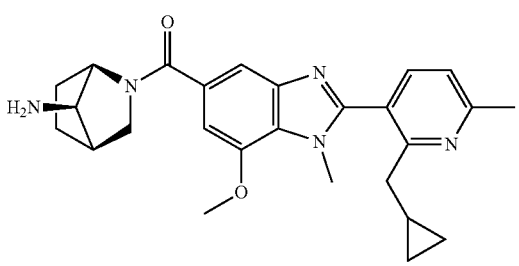

-continued

I-116

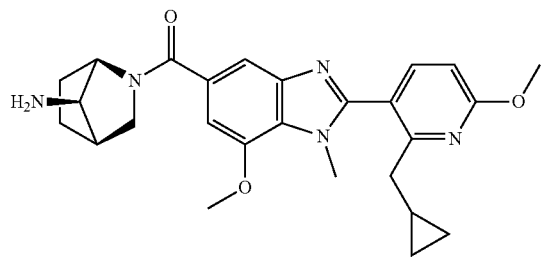

I-117

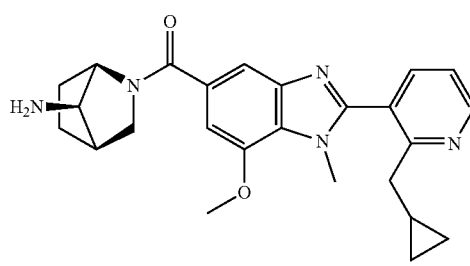

I-118

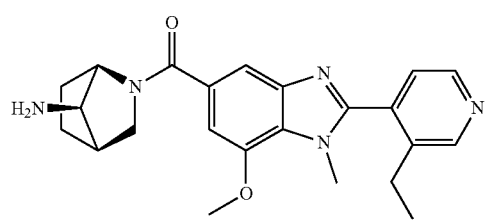

I-119

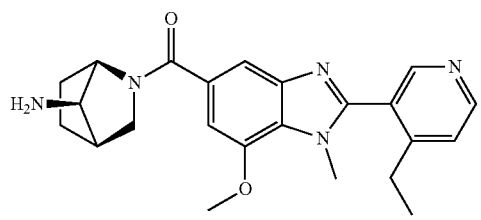

-continued

I-120

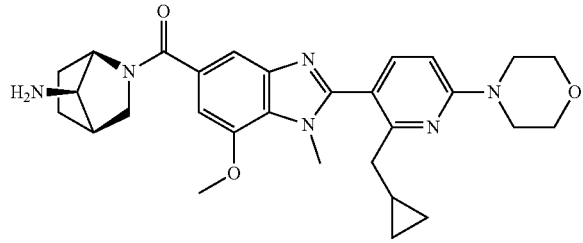

I-121

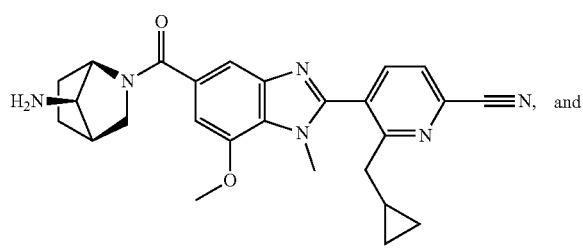

I-122

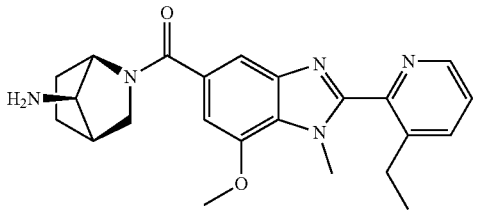

10. A pharmaceutically acceptable composition comprising the compound according to claim 1, and a pharmaceutically acceptable carrier, adjuvant, or vehicle.

11. The composition according to claim 10, in combination with an additional therapeutic agent.

12. A method of inhibiting PAD4 in a subject or in a biological sample comprising the step of contacting the PAD4 with a compound according to claim 1.

13. A method for treating rheumatoid arthritis and cancer in a subject in need thereof comprising the step of administering to said subject the composition according to claim 10.

14. The method according to claim 13, wherein said subject is a human subject.

15. The method according to claim 13, wherein said subject is a veterinary subject.

* * * * *